(12) United States Patent
Blackaby et al.

(10) Patent No.: US 9,044,463 B2
(45) Date of Patent: Jun. 2, 2015

(54) FSH RECEPTOR ANTAGONISTS

(75) Inventors: Wesley Peter Blackaby, Saffron Walden (GB); Martin De Kort, Oss (NL); Mark Enthoven, Oss (NL); Paul Stuart Hinchliffe, Saffron Walden (GB); Cristian Bernard Matthijs Poulie, Oss (NL); Cornelis Marius Timmers, Oss (NL); Saskia Verkaik, Oss (NL)

(73) Assignee: Merck Sharp & Dohme B.V., BN Haarlem (NL)

( * ) Notice: Subject to any disclaimer, the term of this patent is extended or adjusted under 35 U.S.C. 154(b) by 0 days.

(21) Appl. No.: 14/346,124

(22) PCT Filed: Sep. 14, 2012

(86) PCT No.: PCT/EP2012/068127
§ 371 (c)(1),
(2), (4) Date: May 5, 2014

(87) PCT Pub. No.: WO2013/041461
PCT Pub. Date: Mar. 28, 2013

(65) Prior Publication Data
US 2014/0256725 A1    Sep. 11, 2014

Related U.S. Application Data

(60) Provisional application No. 61/537,626, filed on Sep. 22, 2011.

(30) Foreign Application Priority Data

Sep. 22, 2011   (EP) ..................................... 11182305

(51) Int. Cl.
| C07D 209/18 | (2006.01) |
| A61K 31/4045 | (2006.01) |
| C07D 405/14 | (2006.01) |
| C07D 401/12 | (2006.01) |
| C07D 405/12 | (2006.01) |
| C07D 409/12 | (2006.01) |
| C07D 409/14 | (2006.01) |
| C07D 493/04 | (2006.01) |
| C07D 209/14 | (2006.01) |
| A61K 31/4439 | (2006.01) |
| A61K 31/5377 | (2006.01) |

(52) U.S. Cl.
CPC .......... *A61K 31/4045* (2013.01); *C07D 209/18* (2013.01); *C07D 405/14* (2013.01); *C07D 401/12* (2013.01); *C07D 405/12* (2013.01); *C07D 409/12* (2013.01); *C07D 409/14* (2013.01); *C07D 493/04* (2013.01); *C07D 209/14* (2013.01); *A61K 31/4439* (2013.01); *A61K 31/5377* (2013.01)

(58) Field of Classification Search
CPC .......................... C07D 209/18; A61K 31/4045
USPC ............................................ 548/494; 514/419
See application file for complete search history.

(56) References Cited

FOREIGN PATENT DOCUMENTS

| WO | WO2007017289 A2 | 2/2007 |
| WO | WO2008071455 A1 | 6/2008 |

OTHER PUBLICATIONS

International Search Report for PCT/EP2012/068127 (Sep. 14, 2012), mailed on Nov. 21, 2012; 2 pages.

*Primary Examiner* — Robert Havlin
(74) *Attorney, Agent, or Firm* — Kenrick L. Vidale; Catherine D. Fitch

(57) ABSTRACT

The invention relates to FSH receptor antagonist according to general formula I or a pharmaceutically acceptable salt thereof and to a pharmaceutical composition containing the same. The compounds can be used for the treatment and prevention of endometriosis, for the treatment and prevention of pre-menopausal and peri-menopausal hormone-dependent breast cancer, for contraception, and for the treatment of uterine fibroids and other menstrual-related disorders.

Formula I

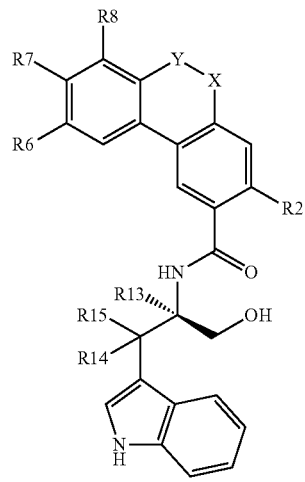

12 Claims, 1 Drawing Sheet

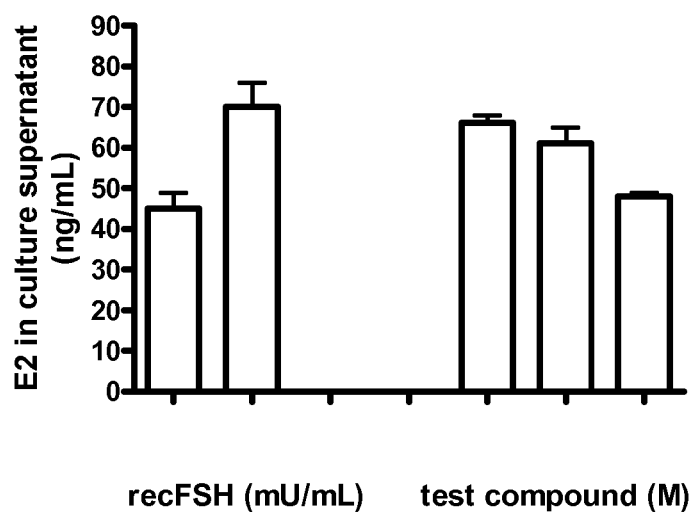
Estradiol (E2) concentration (in ng/mL) in culture supernatant of human granulosa cells, after 48 h incubation with recFSH or with test compound of example 58 in combination with 250 mU/ml recFSH in culture medium with IBMX, followed by 2 h incubation with 10 µM testosterone in culture medium without IBMX (n = 3; mean ± s.e.m.).

FSH RECEPTOR ANTAGONISTS

The invention relates to a compound having FSH receptor modulatory activity, to a pharmaceutical composition containing the same, as well as the use of said compound for FSH receptor mediated diseases.

Gonadotropins are important in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example is released from the anterior pituitary under the influence of gonadotropin-releasing hormone and estrogens and plays a pivotal role in the stimulation of follicle development and maturation. FSH is the major hormone regulating secretion of follicular estrogens, whereas LH (luteinizing hormone) stimulates the production of follicular testosterone and induces ovulation (Sharp, R. M. Clin Endocrinol. 33:787-807, 1990; Dorrington and Armstrong, Recent Prog. Horm. Res. 35:301-342, 1979).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading e.g. to the activation of adenylate cyclase.

The FSH receptor (FSHR) is a highly specific target in the ovarian follicle growth process and is exclusively expressed in the ovary. Blocking this receptor or inhibiting the signaling which is normally induced after FSH-mediated receptor activation will disturb follicle development and thus production of estrogens, ovulation and fertility. Low molecular weight FSH receptor antagonists, henceforth termed FSHR antagonists, could therefore form the basis for medical therapies that are in need of diminished production of estrogens and/or induction of anovulation.

Low molecular weight FSH receptor antagonists have been disclosed in International Applications WO 2008071455, WO 200807145 and WO 2008117175 and in van Straten, N. C. R. and Timmers, C. M. Annual Reports in Medicinal Chemistry 44:171-188, 2009 and van Straten, N. C. R. et al J. Med. Chem. 48:1697-1700, 2005.

Preventing or reversing endometriosis is an important goal in the field of women's health care. Endometriosis is a painful gynecological condition that is characterized by the presence of endometrial tissue in sites outside of the uterine cavity. The prevalence rate is approximately 10% but this may be an underestimate because of the need to perform a laparoscopic procedure to determine the presence of disease. The disease affects women of reproductive age, the most common symptoms being painful menstruation (dysmenorrhoea), pain during intercourse (dyspareunia), painful bowel movement (dyschezia), chronic pelvic pain, heavy periods (menorrhagia), and infertility. If left untreated or inadequately treated endometriosis can either progress or spontaneously regress. In a significant number of women endometriosis is a chronic progressive disease manifesting itself as intractable pain, worsening quality of life, and infertility.

The etiology is unclear which also hampers an understanding of the symptomatic implications of the disease. Endometriosis produces an array of symptoms of varying severity with lack of correlation between stage of disease, disease load and degree of pain thereby causing confusion with clinical classification and delay in diagnosis. Known treatment options are drug therapy and conservative surgery.

Drug therapy is with analgesics, hormonal contraceptives which contain both estrogen and progestagen (Combined Oral Contraceptive (COC)) or progestagen only (Progestagen-Only Contraceptive (POC)), gonadotropin releasing hormone (GnRH) agonists, or other hormones e.g. danazol. Oral contraceptive regimens with combined use of an estrogen and a progestagen (COC) are widely used as first-line therapy in suspected or diagnosed endometriosis, owing to their property to provide cycle control, reduce menstrual flow and eradicate dysmenorrhoea, the most common symptom especially in early-stage disease. However, no single product offers sufficient efficacy in combination with a tolerable level of side effects. COCs may treat some of the symptoms well, but do not effectively suppress the progress of endometriosis and do not effectively treat chronic pelvic pain.

COCs produce initial decidualization of the endometrium by creating a state of pseudocyesis and later atrophy and thinning of the endometrium, thereby providing cycle control, reduction in menstrual flow and reduction of dysmenorrhoea. COCs may treat therefore menstruation-related symptoms but they do not completely suppress the growth of endometriotic lesions and associated chronic pelvic pain.

The mechanism of action of progestagens is initial decidualization of endometrium, followed by atrophy as a result of a direct suppressive effect on estrogen receptors in the endometrium. There is evidence that progestagens suppress matrix metalloproteinases at the molecular level thereby inhibiting the growth of ectopic endometrium. Medroxyprogesterone acetate is the most widely used progestagen for the treatment of endometriosis. Although available for oral administration, medroxyprogesterone acetate is usually administered as a depot formulation every 3 months. The side effects of POCs are multiple, the most common being breakthrough bleeding, nausea, fluid retention and breast tenderness.

GnRH agonists and GnRH antagonists down-regulate the Hypothalamus-Pituitary-Ovary axis by downregulation of the GnRH receptor and GnRH receptor-mediated signalling, resulting in a hypo-estrogenic menopausal state, endometrial atrophy, and amenorrhoea. Although very effective in reducing circulating levels of estrogens, multiple side effects related to menopausal symptoms as well as osteoporosis limit duration of treatment with GnRH agonists to 6 months.

Known drug treatments and/or conservative surgery offer temporary relief only and relapse rates can be as high as 50% with a major impact on fertility and quality of life. Moreover, a significant number of women aged 40-44 years require hysterectomy and bilateral salpingo-oophorectomy.

There is thus a strong need for early therapeutic intervention that improves on the above-mentioned shortcomings of available treatment options. The need is in particular for early therapeutic intervention that suppresses progression of disease and/or improves the side-effect profile (i.e. unscheduled bleeding, bone loss and menopausal symptoms) and improves fertility outcomes.

The present invention therefore relates to FSHR antagonists as a means for the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding.

The present invention provides compounds having the general Formula I or a pharmaceutically acceptable salt thereof.

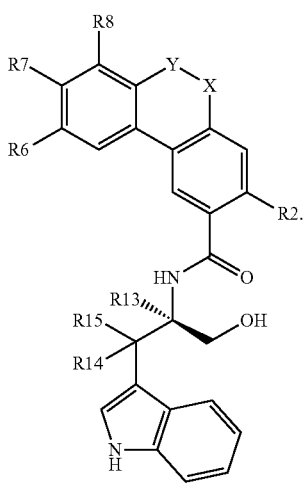

Formula I

In this Formula X, Y, R2, R6, R7, R8, R13, R14 and R15 have the following definitions: Y—X is CH$_2$—CH$_2$, —C(O)O— or —CH$_2$O—.

R2 is phenyl, (1-6C)alkyl, (2-8C)-heteroaryl, benzoyl, (2-8C)heteroarylcarbonyl, (1-8C)alkoxy, (3-6C)cycloalkyl, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or R2 is (2-6C)alkenyl, (2-6C)alkynyl, (1-6C)alkylcarbonyl, (2-6C)alkenylcarbonyl, (2-6C)alkynylcarbonyl, (3-6C)cycloalkylcarbonyl, (3-6C)alkenoxy, (3-6C)cycloalkyl(1-4C)alkoxy, phenyl(1-4C)alkoxy or (2-8C)heteroaryl(1-4C)alkoxy.

R6 is hydroxy, halogen, cyano or H, or

R6 is (1-6C)alkyl, (2-6C)alkenyl, (2-6C)alkynyl, (1-4C)alkoxy, (3-6C)alkenoxy, (3-6C)cycloalkyl(1-4C)alkoxy, (3-6C)cycloalkoxy, (3-6C)heterocycloalkyl(1-4C)alkoxy, the alkyl or alkoxy moieties of which may optionally be substituted with one or more substituents selected from R10, or R6 together with R7 is —O—(CH$_2$)$_n$—O— in which n is 1-3 and in which the CH$_2$ moiety may optionally be substituted by one or more (1-3C)alkyl substituents.

R6 may also be joined with R7 to form a (3-6C)cycloalkyl ring.

R7 is hydroxy, H, or

R7 is (1-6C)alkyl, (2-6C)alkenyl, (2-6C)alkynyl, (1-4C)alkoxy, (3-6C)alkenoxy, (3-6C)cycloalkyl, (3-6C)cycloalkyl(1-4C)alkoxy, (3-6C)cycloalkoxy, (3-6C)heterocycloalkyl(1-4C)alkoxy, (3-6C)heterocycloalkoxy, (2-6C)heterocycloalkylcarbonyl, (di)[1-4C]alkylaminocarbonyl or (2-6C)heterocycloalkyl, the alkyl, alkoxy or (hetero)cycloalkyl moieties of which may optionally be substituted with one or more substituents selected from R11, or R7 is (2-8C)heteroaryl, phenyl, phenyl(1-4C)alkoxy, (2-8C)heteroaryl(1-4C)alkoxy, the phenyl or heteroaryl moieties of which may optionally be substituted with one or more substituents selected from R11, or R7 together with R6 is —O—(CH$_2$)$_n$—O— in which n is 1-3 and in which the CH$_2$ moiety may optionally be substituted by one or more (1-3C)alkyl substituents.

R7 may also be joined with R6 in a (3-6C)cycloalkyl ring.

R8 is H or (1-4C)alkoxy.

R10 is hydroxy, amino, halogen, cyano, nitro, trifluoromethyl, (1-4C)alkoxy, (1-4C)alkyl, aminocarbonyl or (di)[1-4C]alkylamino.

R11 is hydroxy, amino, halogen, cyano, nitro, trifluoromethyl, (1-4C)alkoxy, (di)[1-4C]alkyl]amino or (1-4C)alkyl.

R12 is hydroxy, amino, halogen, cyano, nitro, trifluoromethyl, (1-4C)alkoxy, (1-4C)alkyl, aminocarbonyl or (di)[1-4C]alkylamino.

R13 is H or (1-3C)alkyl.

R14 and R15 are independently H or (1-3C)alkyl.

Alternatively, R14 and R15 may be joined in a (3-6C)cycloalkyl ring.

The compounds according to the present invention have FSH modulatory activity and dose titration with such FSHR antagonists give rise to diminished follicle development (no ovulation) and reduction of circulating levels of estrogens with still sufficient estrogen production left to avoid adverse effects on e.g. bone mass.

Without intending to be bound by theory, the compounds according to the present invention are able to provide optimal control over circulating levels of estrogens by the fact that the compounds are allosteric FSHR antagonists and will therefore be less sensitive to an increase in circulating levels of FSH due to a loss of feedback inhibition by decreased levels of circulating estrogens. Moreover, dose titration of the FSHR antagonist would allow for a second level of control over FSHR signalling and thus over the balance between efficacy (decrease in estrogens) and side effects (minimal level of residual estrogens).

In contrast to GnRHR (ant)agonist treatment regimens, the higher tolerability of FSHR antagonists enables treatment for periods exceeding 6 months.

The term (1-3C)alkyl as used in the definition means a branched or unbranched alkyl group having 1-3 carbon atoms, being methyl, ethyl, propyl and isopropyl.

The term (1-4C)alkyl means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (1-4C)alkoxy means an alkoxy group having 1-4 carbon atoms, the alkyl moiety having to the same meaning as previously defined. (1-3C)Alkoxy groups are preferred.

The term (1-8C)alkoxy means an alkoxy group having 1-8 carbon atoms, the alkyl moiety having the same meaning as previously defined. (1-4C)Alkoxy groups are preferred, (1-3C)alkoxy groups being the most preferred.

The term (1-6C)alkylcarbonyl means an alkylcarbonyl group, the alkyl group of which contains 1-6 carbon atoms with the same meaning as previously defined.

The term (2-6C)alkenyl means a branched or unbranched alkenyl group having 2-6 carbon atoms, such as ethenyl, 2-butenyl, and n-pentenyl.

The term (2-6C)alkenylcarbonyl means an alkenylcarbonyl group, the alkenyl group of which contains 2-6 carbon atoms with the same meaning as previously defined.

The term (3-6C)alkenoxy means an alkenoxy group, the alkenyl group of which contains 3-6 carbon atoms with the same meaning as previously defined.

The term (2-6C)alkynyl means a branched or unbranched alkynyl group having 2-6 carbon atoms, such as ethynyl, propynyl and n-pentynyl.

The term (2-6C)alkynylcarbonyl means an alkynylcarbonyl group, the alkynyl group of which contains 2-6 carbon atoms with the same meaning as previously defined.

The term (3-6C)cycloalkyl means a cycloalkyl group having 3-6 carbon atoms, such as cyclopropyl, cyclobutyl, cyclopentyl and cyclohexyl.

The term (3-6C)cycloalkylcarbonyl means a cycloalkylcarbonyl group, the cycloalkyl group of which contains 3-6 carbon atoms with the same meaning as previously defined.

The term (3-6C)cycloalkoxy means a cycloalkoxy group having 3-6 carbon atoms, such as cyclopropoxy, cyclobutoxy and cyclopentoxy.

The term (3-6C)cycloalkyl(1-4C)alkoxy means a cycloalkylalkoxy group, the cycloalkyl group of which contains 3-6 carbon atoms with the same meaning as previously defined and the alkoxy group of which contains 1-4 carbon atoms with the same meaning as previously defined.

The term (2-6C)heterocycloalkyl means a heterocycloalkyl group having 2-6 carbon atoms, preferably 3-5 carbon atoms, including 1-3 heteroatoms selected from N, O and/or S, which may be attached via a nitrogen if feasible, or a carbon atom. Preferred heteroatoms are N or O.

Preferred number of heteroatoms is one or two. Most preferred are piperidin-1-yl, morpholin-4-yl, pyrrolidin-1-yl and piperazin-1-yl.

The term (3-6C)heterocycloalkyl means a heterocycloalkyl group having 3-6 carbon atoms, preferably 3-5 carbon atoms, including 1-3 heteroatoms selected from N, O and/or S, which may be attached via a nitrogen if feasible, or a carbon atom. Preferred heteroatoms are N or O.

Preferred number of heteroatoms is one or two. Most preferred are piperidin-1-yl, morpholin-4-yl, pyrrolidin-1-yl and piperazin-1-yl.

The term (3-6C)heterocycloalkyl(1-4C)alkoxy means a heterocycloalkylalkoxy group, the heterocycloalkyl group of which of which contains 3-5 C atoms including 1-3 heteroatoms with the same meaning as previously defined and the alkoxy group of which contains 1-4 carbon atoms with the same meaning as previously defined.

The term (3-6C)heterocycloalkoxy means a heterocycloalkoxy group, the heterocycloalkyl group of which of which contains 3-5 C atoms including 1-3 heteroatoms with the same meaning as previously defined.

The term (2-8C)heteroaryl means an aromatic group having 2-8 carbon atoms and 1-4 heteroatoms selected from N, O and S, like imidazolyl, thiadiazolyl, pyridinyl, thienyl, oxazolyl, imidazolyl, pyrazolyl, furyl or indolyl. Preferred number of heteroatoms is one or two. Preferred heteroaryl groups are thienyl, oxazolyl, imidazolyl, pyrazolyl, pyrimidinyl, pyrazinyl, furyl and pyridinyl. Most preferred are thienyl, furyl and pyridinyl. The (2-8C)heteroaryl group may be attached via a carbon atom or a nitrogen, if feasible.

The term (di)[(1-4C)alkyl]amino as used herein means an amino group, monosubstituted or disubstituted with alkyl group(s), each containing 1-4 carbon atoms and having the same meaning as previously defined.

The term (di)[(1-4C)alkyl]aminocarbonyl means a (di) alkylaminocarbonyl group, the alkyl group(s) of which each contain(s) 1-4 carbon atoms with the same meaning as previously defined.

The term phenyl(1-4C)alkoxy means a phenylalkoxy group, the alkoxy group of which contains 1-4 carbon atoms with the same meaning as previously defined.

The term (2-8C)heteroaryl(1-4C)alkoxy means a heteroarylalkoxy group, the heteroaryl group of which contains 2-8 carbon atoms with the same meaning as previously defined and the alkoxy group of which contains 1-4 carbon atoms with the same meaning as previously defined.

The term (2-8C)heteroarylcarbonyl means a heteroarylcarbonyl group, the heteroaryl group of which contains 2-8 carbon atoms with the same meaning as previously defined.

The term (2-6C)heterocycloalkylcarbonyl means a heterocycloalkylcarbonyl group, the heterocycloalkyl group of which contains 2-6 carbon atoms with the same meaning as previously defined.

The term halogen means fluorine, chlorine, bromine or iodine.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one aspect the invention relates to compounds according to Formula I wherein R2 is phenyl, (1-6C)alkyl, (2-8C)-heteroaryl, (1-8C)alkoxy, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or wherein R2 is (2-6C)alkenyl, (3-6C)alkenoxy, (3-6C)cycloalkyl(1-4C)alkoxy, phenyl(1-4C)alkoxy or (2-8C)heteroaryl(1-4C)alkoxy.

In another aspect the invention relates to compounds according to Formula I wherein R13, R14 and R15 is H.

In yet another aspect the invention relates to compounds according to Formula I wherein wherein n, if R6 is combined with R7 is 1.

In yet another aspect the invention relates to compounds according to Formula I wherein R2 is phenyl, (1-6C)alkyl, (2-8C)-heteroaryl, (1-8C)alkoxy, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or wherein R2 is (2-6C)alkenyl, (3-6C)alkenoxy, (3-6C)cycloalkyl(1-4C)alkoxy or phenyl(1-4C)alkoxy.

In yet another aspect the invention relates to compounds according to Formula I wherein R6 is is hydroxy, halogen, cyano or H, or (1-6C)alkyl, (2-6C)alkenyl, (2-6C)alkynyl, (1-4C)alkoxy, (3-6C)alkenoxy, (3-6C)cycloalkyl(1-4C) alkoxy, the alkyl or alkoxy moieties of which may optionally be substituted with one or more substituents selected from R10, or R6 together with R7 is —O—(CH$_2$)$_n$—O— in which n is 1-3 and in which the CH$_2$ moiety may optionally be substituted by one or more (1-3C)alkyl substituents.

R6 may also be joined with R7 to form a (3-6C)cycloalkyl ring.

In yet another aspect the invention relates to compounds according to Formula I wherein R7 is hydroxy, H, or R7 is (1-6C)alkyl, (2-6C)alkenyl, (2-6C)alkynyl, (1-4C) alkoxy, (3-6C)alkenoxy, (3-6C)cycloalkyl, (3-6C)cycloalkyl (1-4C)alkoxy, (2-6C)heterocycloalkylcarbonyl, (di)[1-4C] alkylaminocarbonyl or (2-6C)heterocycloalkyl, the alkyl, alkoxy or (hetero)cycloalkyl moieties of which may optionally be substituted with one or more substituents selected from R11, or R7 is (2-8C)heteroaryl, phenyl, phenyl(1-4C)alkoxy, (2-8C)heteroaryl(1-4C)alkoxy, the phenyl or heteroaryl moieties of which may optionally be substituted with one or more substituents selected from R11, or R7 together with R6 is —O—(CH$_2$)$_n$—O— in which n is 1-3 and in which the CH$_2$ moiety may optionally be substituted by one or more (1-3C)alkyl substituents.

R7 may also be joined with R6 in a (3-6C)cycloalkyl ring.

In another aspect the invention relates to compounds according to Formula I wherein R6 is hydroxy, H, halogen, cyano, or wherein R6 is (1-4C)alkoxy, (3-6C)alkenoxy, the alkyl or alkoxy moieties of which may optionally be substituted with one or more substituents selected from R10.

In addition, R6 together with R7 may also be —O—(CH$_2$)—O— in which the CH$_2$ moiety may optionally be substituted by one or more (1-3C)alkyl substituents.

Alternatively R7 is hydroxy, or R7 is (1-4C)alkoxy, (3-6C) alkenoxy, (3-6C)cycloalkyl(1-4C)alkoxy, (2-6C)heterocycloalkylcarbonyl, (di)[1-4C]alkylaminocarbonyl or (2-6C) heterocycloalkyl, the alkyl, alkoxy or (hetero)cycloalkyl moieties of which may optionally be substituted with one or more substituents selected from R11. R7 can also be (2-8C) heteroaryl, or R7 together with R6 is —O—(CH$_2$)—O— in which the CH$_2$ moiety may optionally be substituted by one or more (1-3C)alkyl substituents.

The invention also relates to compounds according to Formula I wherein R6 and R7 are independently (1-4C)alkoxy or (3-6C)alkenoxy, or R6 together with R7 is —O—CH$_2$—O—.

The invention also relates to compounds according to Formula I wherein the optional substituent R10 in R6 is hydroxy, halogen, cyano, (1-4C)alkoxy, (1-4C)alkyl, aminocarbonyl or (di)[1-4C]alkylamino.

The invention also relates to compounds according to Formula I wherein the optional substituent R11 in R7 hydroxy, (1-4C)alkoxy, (di)[1-4C]alkyl]amino or (1-4C)alkyl.

The invention also relates to compounds according to Formula I wherein the optional substituent R12 in R2 hydroxy, amino, halogen, (1-4C)alkoxy, (1-4C)alkyl, aminocarbonyl or (di)[1-4C]alkylamino.

In yet another aspect the invention resides in the compounds according to Formula I selected described in examples 1-57.

The invention also relates to those compounds wherein all specifications for X, Y, R2, R6, R7, R8, R13, R14 and R15 in the various aspects of the invention as described hereabove occur in any combination within the definition of the compound according to Formula I.

In another aspect the invention relates to compounds of Formula I which have a pIC50 of 5 or higher. In yet another aspect the invention relates to compounds according to Formula I with a pIC50 of more than 7.

The skilled artisan will recognize that desirable IC50 values are dependent on the compound tested. For example, a compound with an IC50 value which is less than $10^{-5}$ M is generally considered a candidate for drug selection. Preferably, this value is lower than $10^{-7}$ M. However, a compound which has a higher IC50 value, but is selective for the particular receptor, may be even a better candidate.

In vitro assays to determine receptor binding or the biological activity of gonadotropin receptor agonists and antagonists are well-known. In general, cells expressing the receptor are incubated with the compound to be tested and the binding or stimulation or inhibition of a functional response is determined. To measure a functional response, isolated DNA encoding the FSH receptor gene, preferably the human receptor, is expressed in a suitable host cell-line. Such a host cell-line might be the Chinese Hamster Ovary cell-line, but other cell-lines can also be used. Preferably, the host cells are of mammalian origin (Jia et al (1991) Mol Endocrinol 5, 759-776).

Methods to construct FSH receptor-expressing cell lines are well-known in the art (e.g., Sambrook et al., Molecular Cloning: A Laboratory Manual, Cold Spring Harbor Laboratory Press, latest edition). Heterogolous expression of the receptor is obtained by transfection and expression of the DNA encoding the desired protein. Techniques for site-directed mutagenesis, ligation of additional sequences, PCR, and construction of suitable expression systems are also well-known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well-known, expression systems are available, which are compatible with a wide variety of hosts, including prokaryotic hosts such as bacteria and eukaryotic hosts such as yeast, plant cells, insect cells, avian cells, mammalian cells, and the like.

Cells expressing the receptor are then incubated with the test compound to determine binding, or stimulation or inhibition of a functional response. Alternatively, isolated cell membranes containing the expressed receptor may be used to measure binding of compound.

For measurement of binding, radioactively- or fluorescently-labeled compounds may be used. Alternatively, competition binding assays may be performed. FSH receptor antagonistic compounds can also be identified in screening assays that involve the determination of receptor-mediated cAMP accumulation. Such methods involve the expression of the FSH receptor in a host cell-line and incubation of the cells with a concentration range of the test compound in the presence of a fixed, submaximally effective, FSH concentration (i.e., a FSH concentration that induces approximately 80% of the maximal cAMP accumulation by FSH in the absence of test compound). The amount of cAMP is then measured. From the concentration-effect curves, the IC50 value and the percentage of inhibition of FSH-induced cAMP accumulation can be determined for each of the compounds. As agonist, human recombinant FSH can be used.

In addition to the direct measurement of cAMP levels in the FSH receptor-expressing cell-line, cell-lines may be transfected with a second cDNA that encodes a reporter gene, of which the expression is dependent on the intracellular concentration of cAMP. Such reporter genes might be cAMP-inducible or be constructed in such a way that they are connected to novel cAMP responsive elements. In general, reporter gene expression might be controlled by any response element reacting to changing levels of intracellular cAMP. Suitable reporter genes are e.g. the genes encoding beta-galactosidase, alkaline phosphatase, firefly luciferase and green fluorescence protein. The principles of such transactivation assays are well-known in the art and are described for example in Stratowa et al (1995) Curr Opin Biotechnol 6, 574. Changes in intracellular cAMP levels may also be determined in live-cell cAMP biosensor assays, like the GloSensor™ cAMP assay, which uses a genetically encoded biosensor with a cAMP binding domain fused to a mutant form of luciferase, or the ACT One™ cAMP assay, which utilizes a cAMP-gated ion channel as a biosensor. Antagonistic compounds may also be identified in assays that are based on receptor-induced recruitment of beta-arrestin to the agonist-occupied receptor (e.g., Transfluor® assay, PathHunter® and Tango™ beta-arrestin assays) or receptor internalization assays (e.g., PathHunter® endocytosis assays). Label-free assays may also be applicable to screen for FSH receptor antagonists. These assays are based on receptor-induced dynamic mass redistribution of intracellular content or receptor-induced changes in cell morphology or adhesion (Van Koppen (2010) Drug Discovery tb 7, 69).

The compounds of Formula I can form salts which are also within the scope of this invention. Reference to a compound of Formula I herein is understood to include reference to salts thereof, unless otherwise indicated.

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers.

The chiral centers of the present invention can have the S or R configuration as defined by the IUPAC 1974 Recommendations.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press and Jana S. et al, Current Med. Chem. 17, 3874-3908, 2010. The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The present disclosure describes the preparation of low molecular weight compounds that show selective modulatory activity on the FSH receptor. The compounds of the invention can be used as (partial) antagonists of the FSH receptor.

The present invention therefore relates to FSHR antagonists as a means for the treatment and/or prevention of endometriosis, for the treatment and/or prevention of pre-menopausal and peri-menopausal hormone-dependent breast cancer, for contraception, and for the treatment of uterine fibroids and other menstrual-related disorders, such as dysfunctional uterine bleeding.

Thus, the compounds according to the invention can be used in therapy.

A further aspect of the invention resides in the use of compounds according to the invention or a pharmaceutically acceptable salt thereof for the treatment of FSH receptor-mediated diseases.

Another aspect of the invention resides in the use of compounds or a pharmaceutically acceptable salt thereof having the general formula I for the treatment of diseases wherein FSHR mediated signaling plays a role, in particular those diseases wherein signaling can be inhibited by antagonizing the FSHR. These include, but are not limited to, the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding.

In a further embodiment of the invention, a compound according to the invention is used to treat endometriosis by providing improved control over circulating levels of estrogens by dose titration thereby allowing optimal control over the balance between efficacy and side effects. Moreover, the selective on-target interaction with the FSHR will not impede LHR mediated signalling and associated production of testosterone. With the improvement in tolerability, a compound according to the present invention can also provide a simple effective treatment, preferably by the oral route of administration, in an early stage of the disease in a patient population familiar with contraceptive methods. Oral treatment is available by administration of a compound according to the invention in a pharmaceutical formulation. During treatment with a compound according to the invention, regular bleeding can be partially or completely avoided (inducing amenorrhoea). This is particularly useful in the treatment of endometriosis since it diminishes or prevents retrograde menstruation and thereby minimizes recurrence of disease.

A compound according to the invention can also be used for contraception. A compound according to the invention has therapeutic and contraceptive effect while inducing a mostly atrophic or inactive endometrium. This treatment thereby avoids endometrial proliferation or hyperplasia. Compounds according to the invention are also useful for treatment of other menstrual-related conditions such as fibroids and dysfunctional uterine bleeding. Furthermore, in view of the property of the compounds, according to the invention, to diminish circulating levels of estrogens, a compound according to the invention is also very useful for treatment of estrogen receptor positive breast cancer, either alone or in combination with an estrogen receptor antagonists such as tamoxifen or a selective estrogen receptor downregulator such as fulvestrant, in pre-menopausal and perimenopausal women.

Appropriate methods to prepare the compounds of the present invention are outlined below.

Here we describe compounds of general formula I, in which X—Y, R2, R6-R8 and R10-R15 have the same meaning as previously defined. The R-group numbering for R2, and R6-R8 refers to the position of the substituents relative to the scaffold, based on the 9,10-dihydrophenantrene numbering, as indicated below.

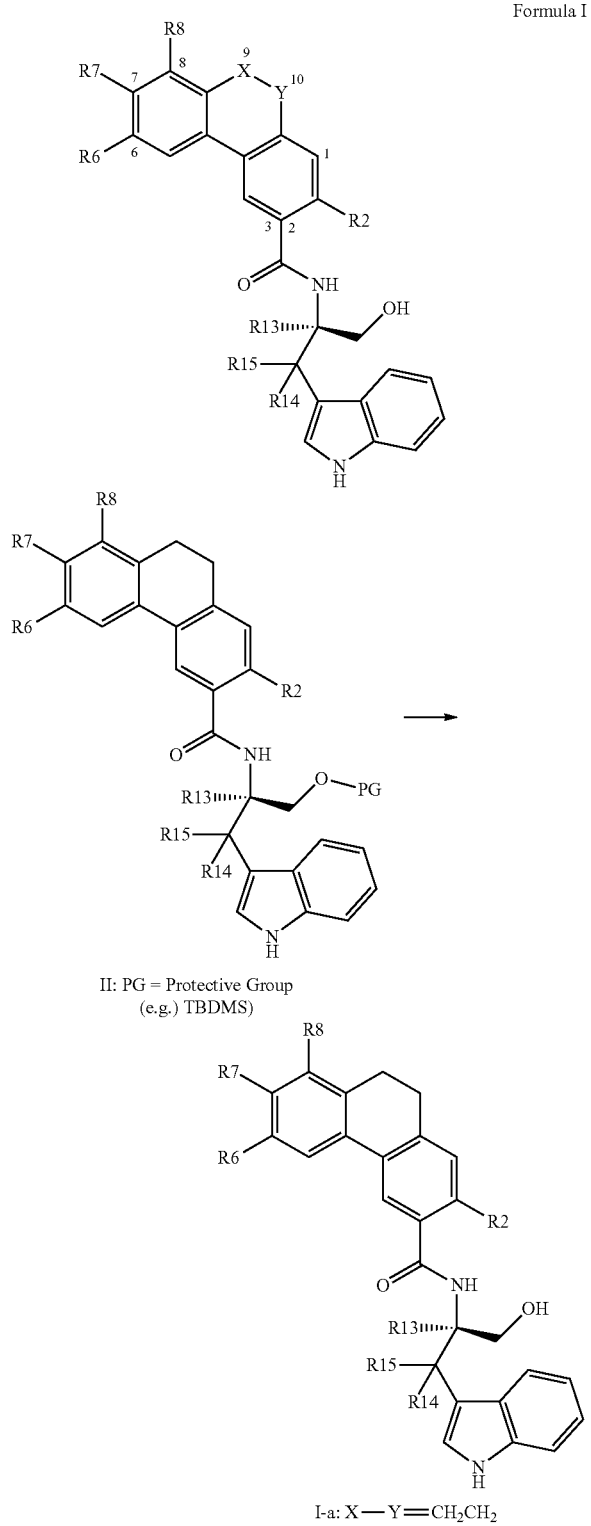

I-a: X—Y═CH₂CH₂

9,10-Dihydrophenantrene-3-carboxamides of general formula I-a, in which X—Y═CH₂CH₂, are accessible by deprotection of derivatives of general formula II, with PG=Protective Group. In most cases, protection of the primary hydroxyl function with silyl ethers such as the tert-butyl dimethylsilyl (TBDMS) group is compatible with the reaction conditions (vide infra), but also other hydroxyl-protecting groups may be envisioned, such as (substituted) trityl or benzyl ethers. The TBDMS group may easily be removed by treatment of compounds II with fluoride ion (e.g tetra-n-butyl ammonium fluoride), but unmasking of the protected hydroxyl functionality (with any hydroxyl-protecting group) to arrive at compounds I-a is considered part of the standard synthetic repertoire of those skilled in the art. Related protective group manipulations are described in: T. W. Greene et al., *Greene's protective groups in organic synthesis*, 4th Ed., John Wiley & Sons, Hoboken, N.J., 2007.

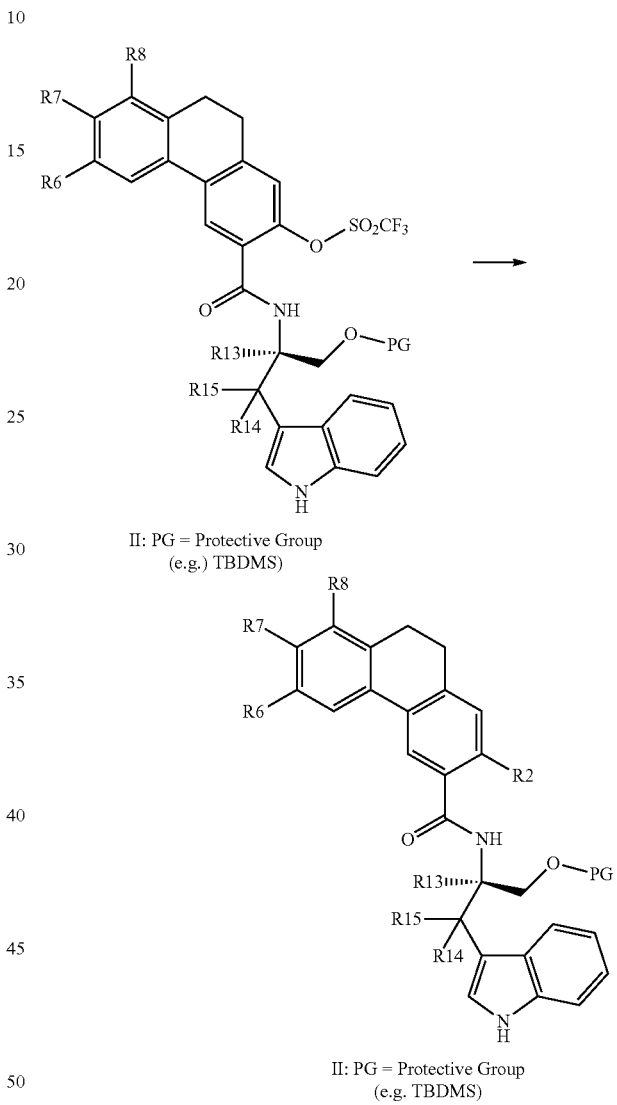

Introduction of the required substituents R2 in compounds of general formula II may be accomplished by organometal-catalyzed transformations, e.g. using organopalladium catalysts, based on 2-triflates of general formula III. Effective methodologies to introduce substituents R2 comprise the well known Suzuki, Stille and Sonogashira coupling reactions. Compounds of general formula II, in which R2 contains a ketone functionality (e.g. R2=(hetero)arylcarbonyl) are accessible by generation of an anion at C-2 of the 9,10-dihydrophenantrene-3-carboxamide scaffold starting from triflates of general formula III by transmetallation (at low temperature) with strong non-nucleophilic bases such as LDA or LiHMDS in an aprotic solvent such as THF, followed by quenching with the appropriate (commercially available) acyl chloride (R2-Cl).

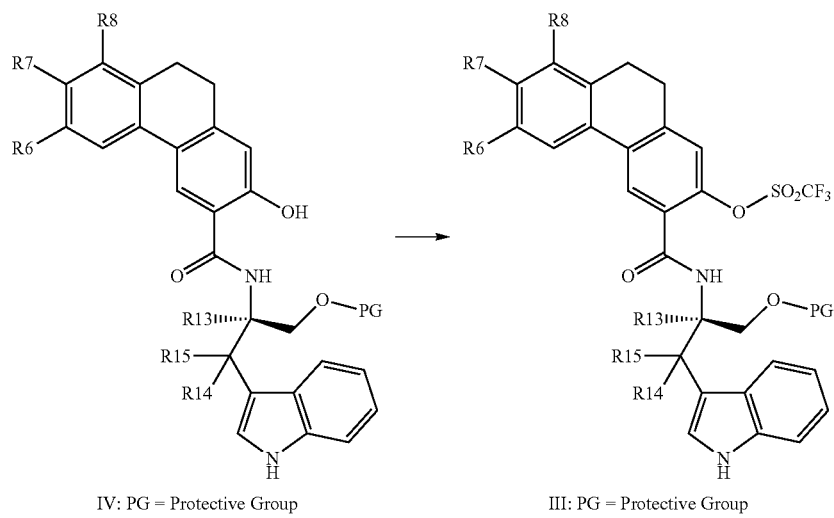

IV: PG = Protective Group
(e.g. TBDMS)

III: PG = Protective Group
(e.g. TBDMS)

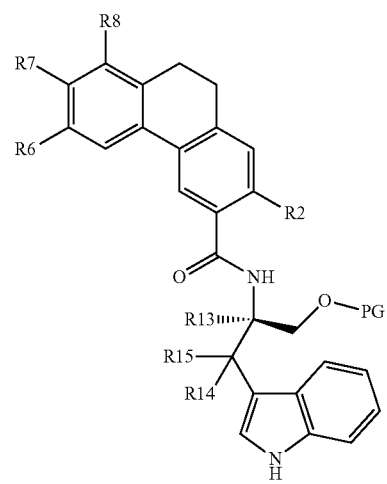

II-a: PG = Protective Group
(e.g. TBDMS)
R2 = (cyclo)alkoxy

2-O-Triflates of general formula III are accessible by standard triflation of the phenolic substituent in derivatives of general structure IV. In a typical reaction procedure, phenols of general formula IV are dissolved in an aprotic solvent such as dichloromethane or THF and treated with triflic anhydride in the presence of a suitable base, such as triethyl amine. In a similar fashion, derivatives of general formula II-a can be prepared, in which R2=(cyclo)alkoxy. Standard alkylation using (cyclo)alkyl halides and an appropriate base, such as potassium carbonate, sodium hydride or triethyl amine in an aprotic solvent at room temperature or elevated temperature provides the desired 2-O-alkylated derivatives II-a.

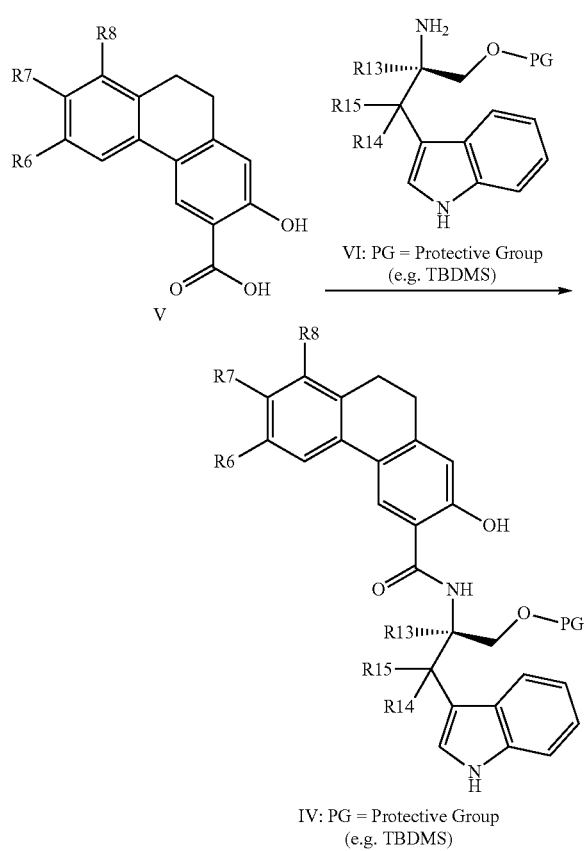

IV: PG = Protective Group
(e.g. TBDMS)

3-Carboxamides of general structure IV may be prepared by condensation of carboxylates of general structure V with protected tryptophanol derivatives of general formula VI using methods well known to those skilled in the art. For example, reaction of V with VI may be effected in an aprotic solvent such as THF or dichloromethane in the presence of a (commercially available) peptide coupling agent, like DCC, TBTU, HATU, EEDC, etc. and a suitable base, such as DiPEA. In turn, the required carboxylates V may be obtained from the corresponding methyl esters of general formula VII by standard saponification. Thus, treatment of methyl esters VII with NaOH in EtOH or dioxane/water mixtures at elevated or room temperature provides carboxylates V.

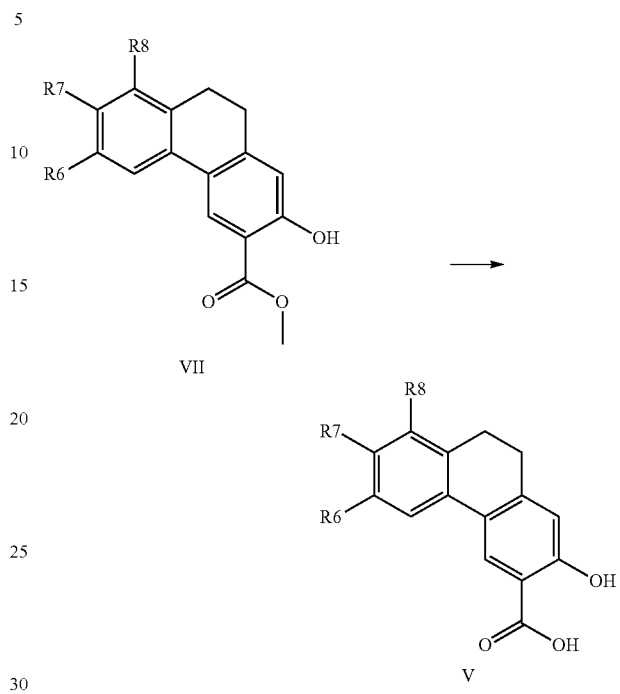

In an alternative fashion, introduction of the required R2 substituent on the 9,10-dihydrophenantrene-3-carboxyl scaffold, as described above (e.g. III→II or IV→II-a) may also be accomplished in the (methyl) ester stage. Thus, conversion of phenolic esters VII by direct O-alkylation as described above for the conversion of IV→III-a provides functionalized esters IX (R2=(cyclo)alkoxy). Accordingly, O-triflation as described for the conversion of IV→III, followed by organometal-catalyzed transformations, e.g. using organopalladium catalysts, such as Suzuki, Stille and Sonogashira coupling protocols (vide supra), gives access to functionalized esters IX.

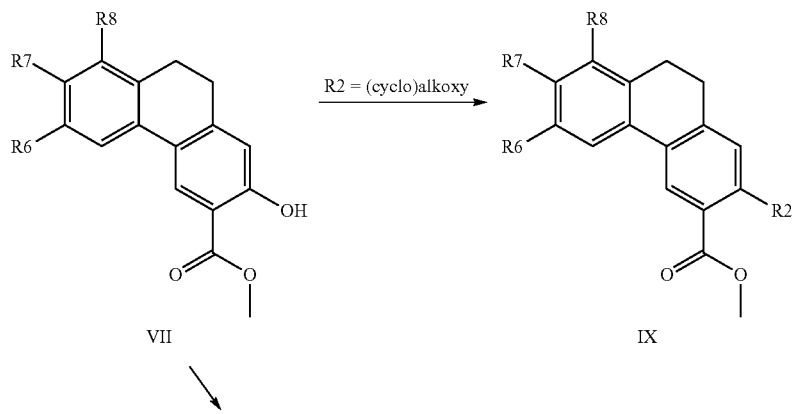

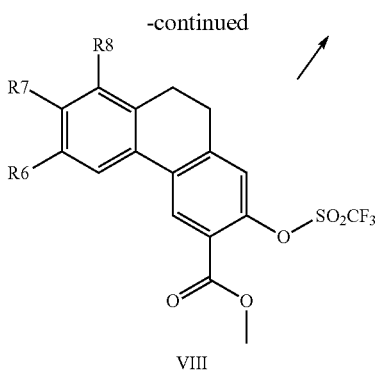

VIII

Based on the synthetic strategy outlined above for the preparation of compounds I-a from derivatives of general formula VII, also esters IX may be converted to end products of general formula I-a. The reaction steps for this route are identical or very similar to those described above (VII→I-a). However, the requisite substituent R2 is now introduced at an earlier stage in the protocol and is carried unchanged through the synthetic process.

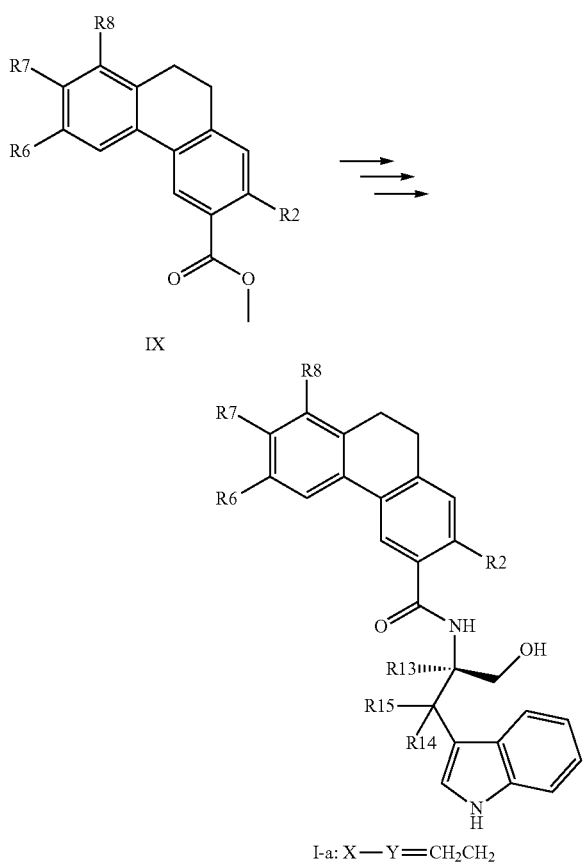

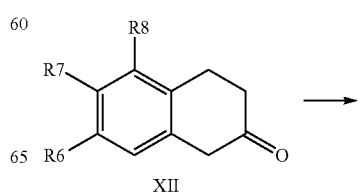

I-a: X—Y=CH$_2$CH$_2$

Construction of the 9,10-dihydrophenantrene-3-carboxyl scaffold in VII may be effected using a Lewis-acid catalyzed cyclocondensation reaction, starting from silyl enol ethers X and bis-silylated methyl acetoacetate XI. Typically, silyl enol ethers of general formula X are dissolved in trimethyl orthoformate at low temperature (−78° C.), upon which TiCl$_4$ is added as the Lewis acid catalyst. Related conversions are described in T. H. Chan et al., *J. Am. Chem. Soc.* 102, 3534-3538 (1980).

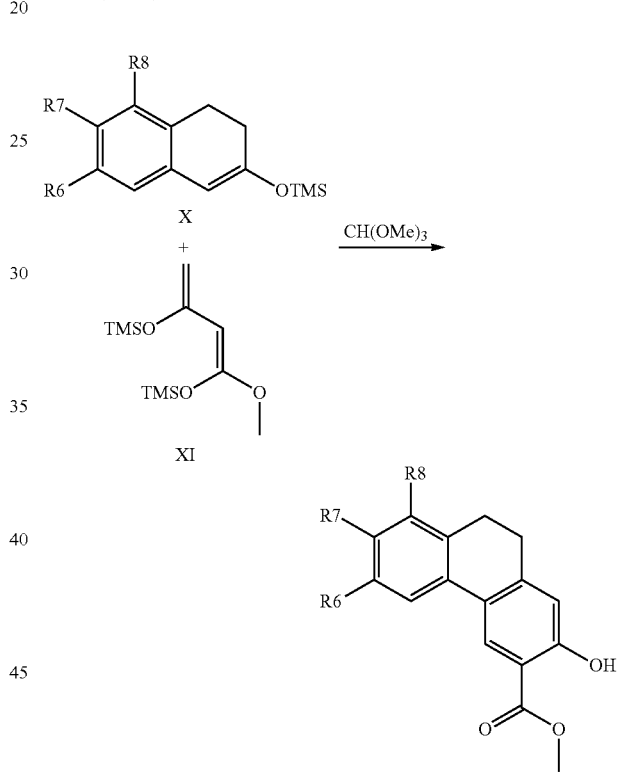

The required silyl enol ethers X and XI can be prepared from their respective beta-tetralone precursors of general formula XII or commercially available, partially silylated analog XIII by deprotonation with a strong base, such as LiHMDS or n-BuLi/TMEDA in an aprotic solvent such as THF and subsequent quenching with TMS-Cl

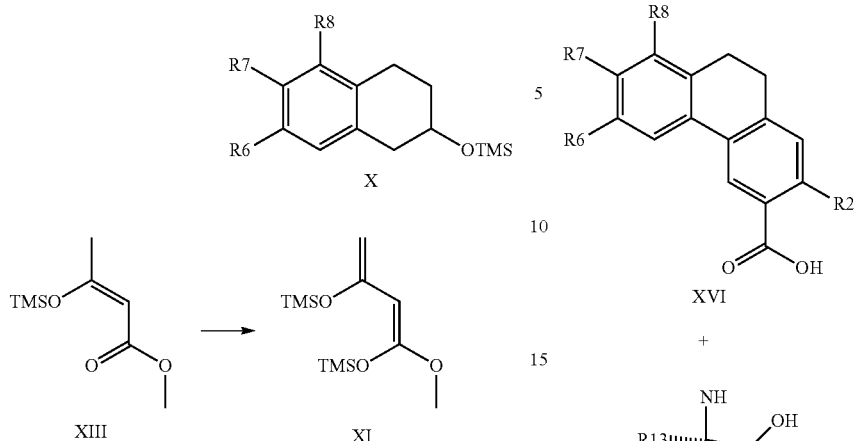

Beta-tetralones of general structure XII are either commercially available, or may be prepared from their aryl acetic acid precursors of general formula XV. A general method to arrive at ketones XII is treatment of the acids XV with oxalyl chloride and subsequent reaction of the resulting acyl chlorides with ethene in the presence of a strong Lewis acid such as AlCl$_3$ and quenching with NaHSO$_3$ to give beta-tetralone precursors XIV. Ensuing sulphurous acid elimination in the presence of a suitable base, such as K$_2$CO$_3$, then gives access to ketones XII.

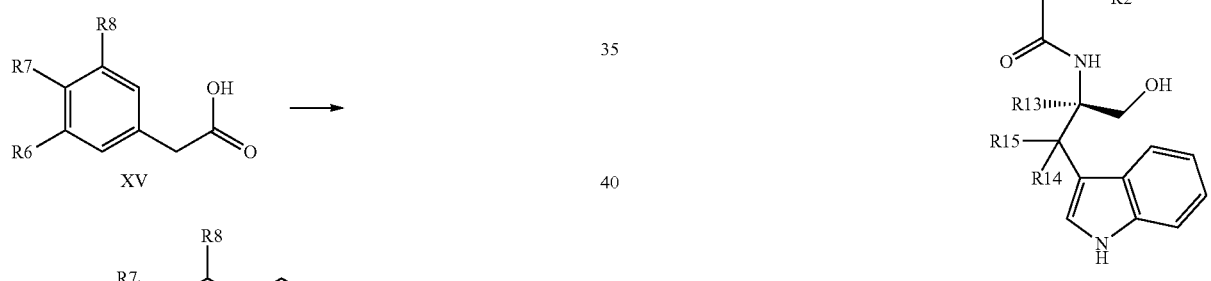

6-H-Benzo[c]chromene derivatives of general formula I-b, in which X—Y=CH$_2$—O, may be prepared from carboxylates XVI and tryptophanol derivatives XVII by standard peptide coupling protocols. For example, reaction of XVI with XVII may be effected in an aprotic solvent such as THF or dichloromethane in the presence of a (commercially available) peptide coupling agent, like DCC, TBTU, HATU, EEDC, etc. and a suitable base, such as DiPEA. Such conversions are regarded to be familiar to those of skill in the art.

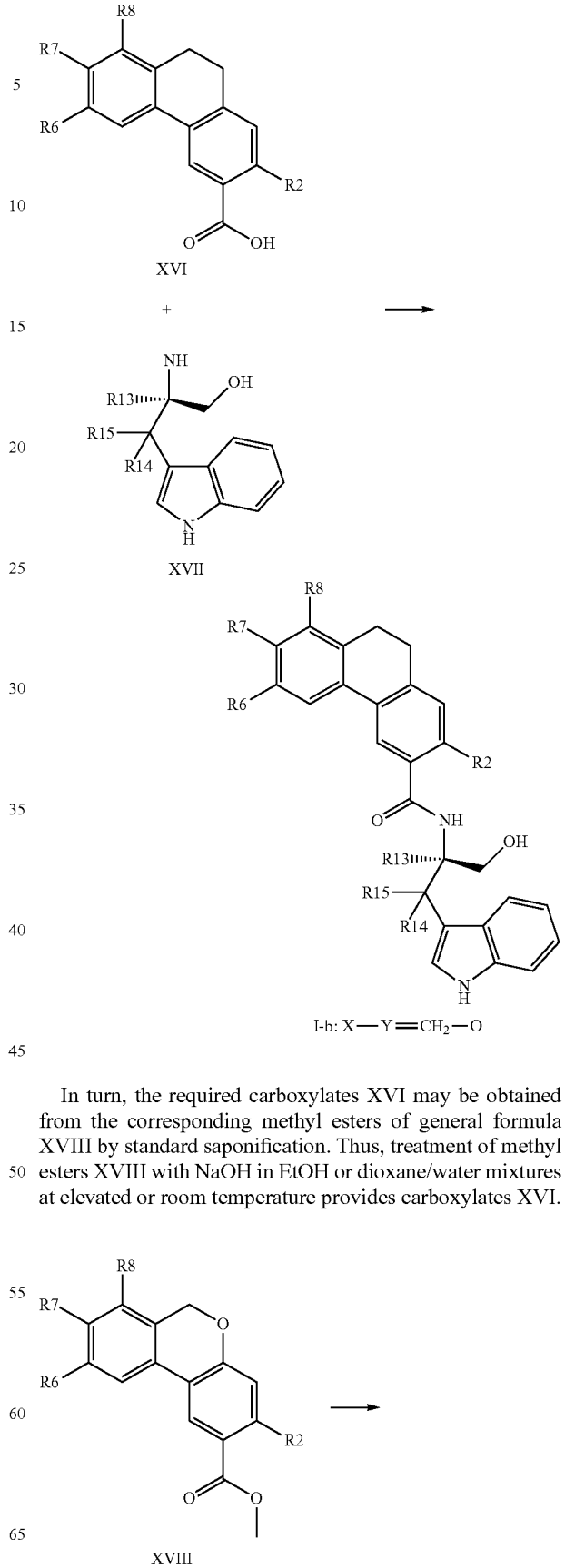

In turn, the required carboxylates XVI may be obtained from the corresponding methyl esters of general formula XVIII by standard saponification. Thus, treatment of methyl esters XVIII with NaOH in EtOH or dioxane/water mixtures at elevated or room temperature provides carboxylates XVI.

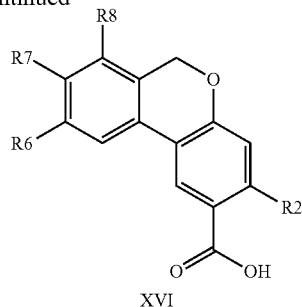

XVI

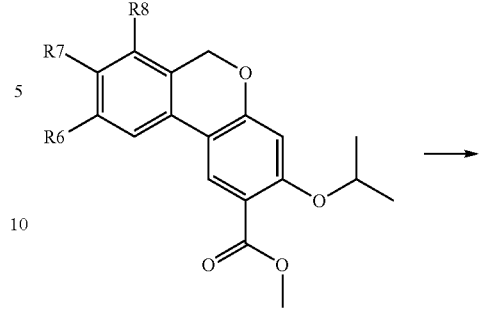

XVIII-a: R2 = isopropoxy

XX

Depending on the nature of substituent R2, introduction of this vector to the central scaffold may be effectuated at the (methyl)ester stage. To this end, R2 may be introduced using various methods described above for the preparation of compounds of general formula IX. Accordingly, conversion of phenolic esters XX by direct O-alkylation as described above for the conversion of VII→IX provides functionalized esters XVIII (R2=(cyclo)alkoxy). In a similar fashion, O-triflation of phenolic derivatives XX as described for the conversion of VII-VIII, gives access to triflates XIX. Ensuing organometal-catalyzed transformations, e.g. using organopalladium catalysts, such as Suzuki, Stille and Sonogashira coupling protocols (vide supra), yields functionalized esters of general formula XVIII.

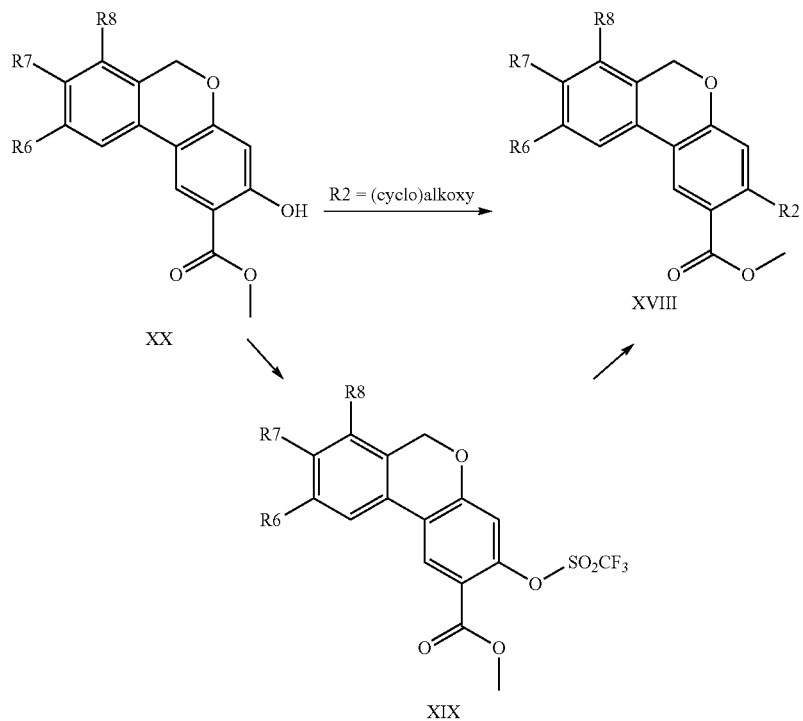

Phenolic esters of general structure XX may easily be obtained by dealkylation of isopropoxy-precursors of general formula XVIII-a, in which R2=isopropoxy. Such conversions are well known to those skilled in the art and may be realized by treatment of XVIII-a with suitable Lewis acids, such as $AlCl_3$, in an aprotic solvent, such as dichloromethane. Related orthogonal protective group manipulations are described in: T. W. Greene et al., *Greene's protective groups in organic synthesis*, 4th Ed., John Wiley & Sons, Hoboken, N.J., 2007.

The requisite 6-H-benzo[c]chromene scaffold may be constructed from benzylic ethers of general structure XXI via a Heck-type intramolecular biaryl coupling reaction. Thus, cyclization of bromides XXI using a palladium(II) catalyst such as $Pd(OAc)_2$ in a suitable solvent such as THF gives rise to the tricyclic system present in structures of general formula XVIII. It is important to note that the regioselectivity of the ring-closure reaction is largely governed by the spatial orientation and steric bulk of the ring-substituent R2. Related intramolecular biaryl coupling reactions have been described in: K. C. Majumdar et al., *Synthesis* 9, 793-800 (2009).

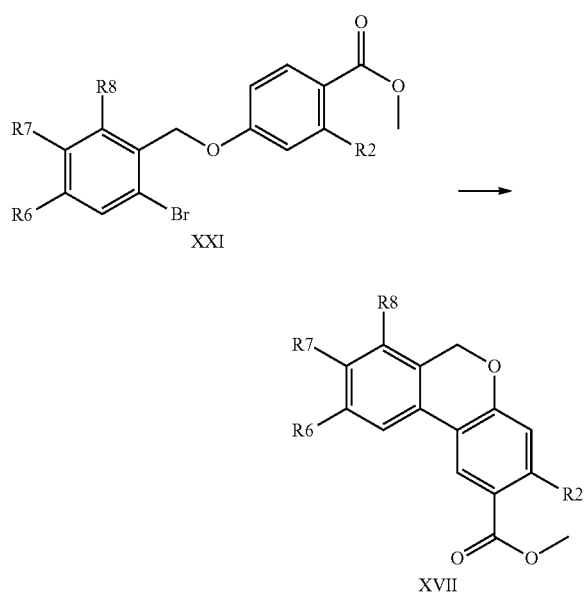

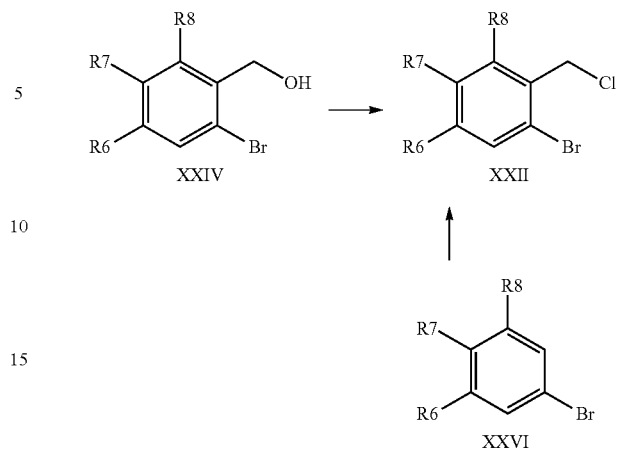

The benzylic ethers XXI are accessible by O-alkylation of phenols of general formula XXIII with suitable benzyl chlorides XXII. In a typical experiment, deprotonation of phenols XXIII is effected with NaH in DMF, leading to efficient reaction with benzyl chlorides XXII.

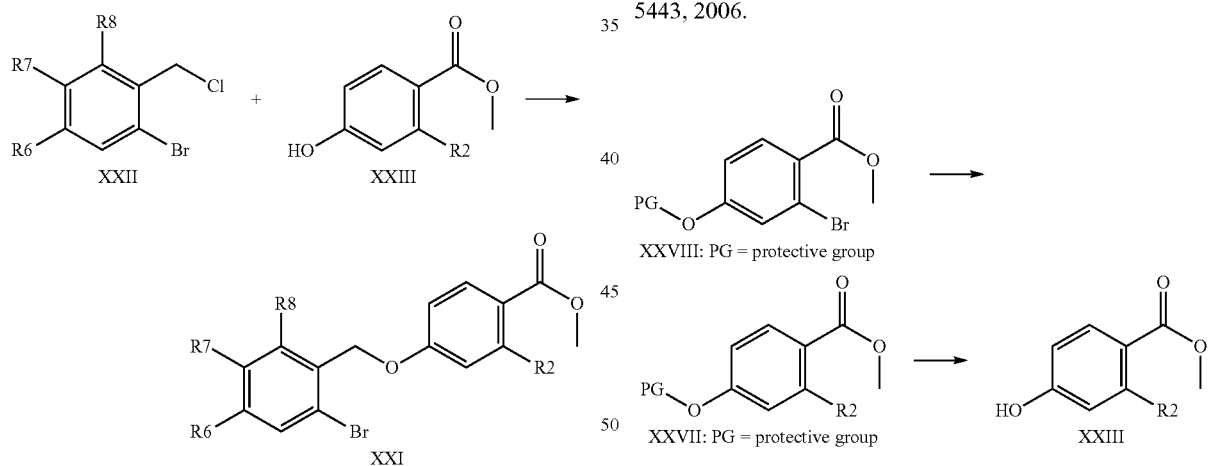

Depending on the substituents R6-R8, benzyl chlorides XXII may be commercially available, or may be accessible by an elementary sequence of reaction steps, known to those of skill in the art and well documented in literature.

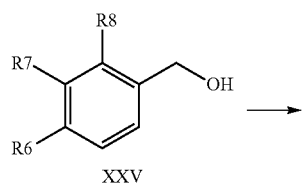

For example, benzyl alcohols XXV may undergo ortho-bromination after treatment with bromine in acetic acid (concomitant O-acetylation may occur, the acetyl group may later be removed by saponification), providing bromides XXIV. Subsequent chlorination of the benzylic hydroxyl group in XXIV is easily effected by treatment with thionyl chloride in DMF. Alternatively, depending on the commercial availability of requisite aromatic precursors, bromides XXVI may be equipped with a chloromethyl substituent using standard chloromethylation conditions, such as formaldehyde and hydrochloric acid at elevated temperature in a suitable solvent such as water. Related chloromethylation reactions have been reported in: J. M. Heemstra et al., *Organic Letters* 8, 5441-5443, 2006.

Phenolic derivatives XXIII are, depending on the nature of R2, either commercially available, or may be prepared by standard functional group transformations, well known to those skilled in the art. Thus, functionalization of commercially available methyl 2-bromo-4-hydroxybenzoate with an appropriate hydroxyl-protecting group, such as the tert-butyldimethylsilyl (TBDMS) ether (vide supra), yields esters XXVIII. Subsequent introduction of R2 using organometal-catalyzed transformations, e.g. using organopalladium catalysts, such as Suzuki, Stille and Sonogashira coupling protocols (vide supra), yields functionalized esters of general formula XXVII. Finally, unmasking of the hydroxyl-protecting group in XXVII using conditions reported above gives access to the required phenolic esters XXIII.

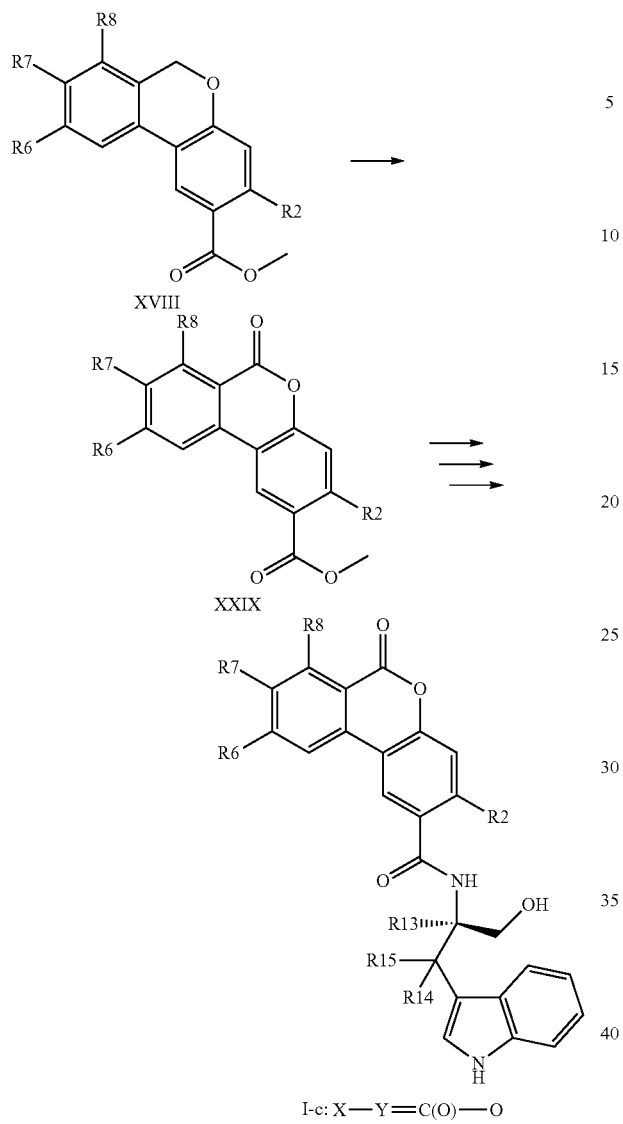

I-c: X—Y=C(O)—O

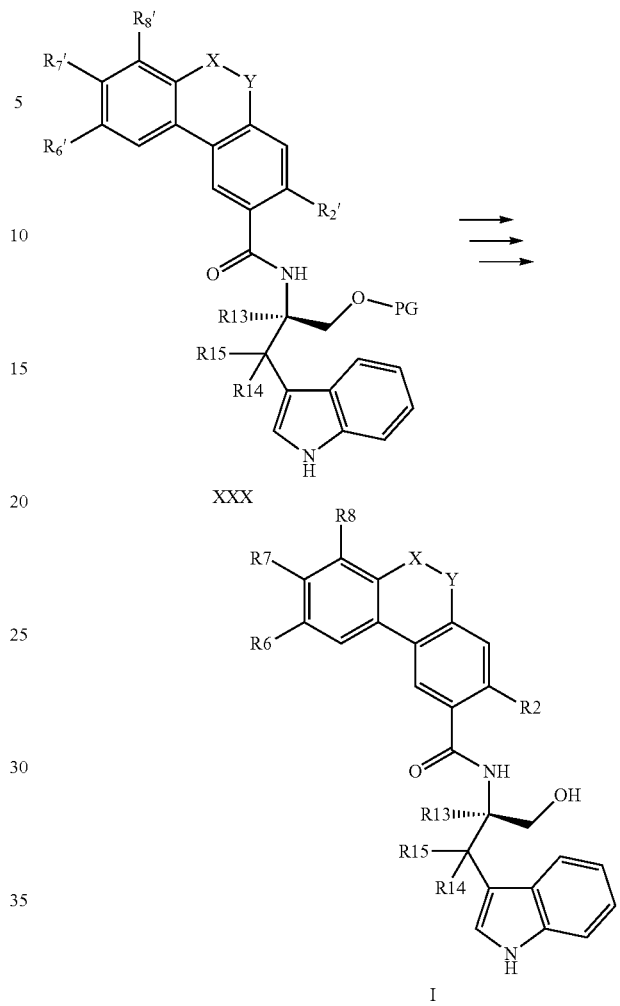

Compounds of general formula I-c, in which X—Y=C(O)—O are accessible from previously mentioned methyl esters of general formula XVIII by oxidation of the benzylic position. In a typical experiment, esters XVIII are dissolved in a suitable solvent mixture, such as acetonitrile/water and treated with an appropriate oxidant, such as 4-acetamido-2,2,6,6-tetramethyl-1-oxopiperidinium tetrafluoroborate, to afford lactones of general formula XXIX. Related conversions have been reported in: J A. Teske, *Organic Letters* 10, 2195-2198, 2008.

The lactones XXIX may be further processed using the synthetic sequences delineated above (e.g. IX→I-a or XVIII→I-b) to provide target compounds of general formula I-c. It is of importance to note that the lactone ring in XXIX is not susceptible to hydrolysis if the above described conditions for the saponification of the methyl ester are used.

Those skilled in the art will appreciate that the above delineated transformations to arrive at compounds of general formula I are identical in case of longer alkyl (e.g. ethyl, propyl, butyl, etc.) esters instead of methyl esters and selection of the synthons will be guided by the (commercial) availability of the appropriately functionalized reagents.

For the synthesis of compounds of general formula I the overall approach indicated above was employed, making use of tailor-made functionalized intermediates. This means that, depending on the required substituents R2 and R6-R8 (where R-numbering refers to the atom numeration in the scaffold), either the required substituents are brought in place at the beginning of the synthesis (i.e. R2=R2', R6=R6', etc.), or are introduced at any stage judged to be convenient in the course of the synthesis of the products of general formula I. In that case suitable alternative functionalities are introduced first, indicated as R2', R6'-R8' in structures of general formula XXX, which allow for the conversion into the desired R2 and R6-R8 in one or more additional manipulations (i.e. conversion of XXX to I as indicated above), with R2 and R6-R8 having the same meaning as previously defined. It is important to notice that such conversions in most cases are not compatible with a free hydroxyl functionality, therefore the presence of a suitable hydroxyl-protecting group, as indicated in XXX, is deemed necessary. Appropriate hydroxyl-protecting groups comprise silyl-ethers, such as tert-butyl-dimethylsilyl groups (TBDMS groups), which are introduced using standard conditions (i.e. treatment with TBDMS-Cl using an appropriate base, such as pyridine or DiPEA in an aprotic solvent such as dichloromethane or THF) well known to those of skill in the art. Such silyl ethers may be deprotected by acid or fluoride ion (tert-butyl ammonium fluoride, TBAF) treatment at any stage considered to be convenient in the synthetic sequence leading to target derivatives of general formula I. An overview of suitable protective group manipulations may be found in: T. W. Greene et al., *Greene's protective groups in organic synthesis*, 4th Ed., John Wiley & Sons, Hoboken, N.J., 2007.

Similarly, manipulation of substituents in an earlier stage of the synthetic protocol towards compound of general formula I, might be performed on esters of general formula XXXI, in which R2' and R6'-R8' may be converted to R2 and R6-R8, as described above to provide derivatives of general formula IX (X—Y=CH$_2$CH$_2$), XVIII (X—Y=CH$_2$—O) or XXIX (X—Y=C(O)—O).

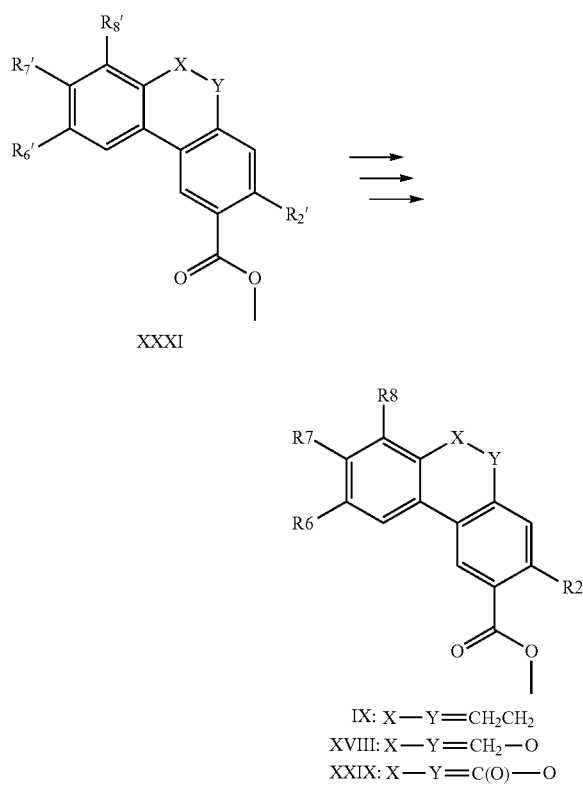

Generally, in order to manipulate substituents at the C2, and C6-C8 positions of the target scaffolds, halogen atoms like bromine, iodine or triflates can be used. Triflates, in turn, may be present in the initial precursors as alkoxy groups, which, after dealkylation using e.g. BBr$_3$, and subsequent triflation using e.g. triflic anhydride, provide the requisite tool compounds for further manipulation. Aromatic halides or triflates can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles. These approaches are especially useful for connecting heterocyclic structures to specific positions of the scaffold, e.g. by coupling of tailor-made heterocyclic structures (like boronates or stannanes).

Substituents on the aromatic ring (R6-R8) can often be introduced already in the monocyclic precursors (e.g. XV, XXV or XXVI), carrying them unchanged throughout the further synthetic process.

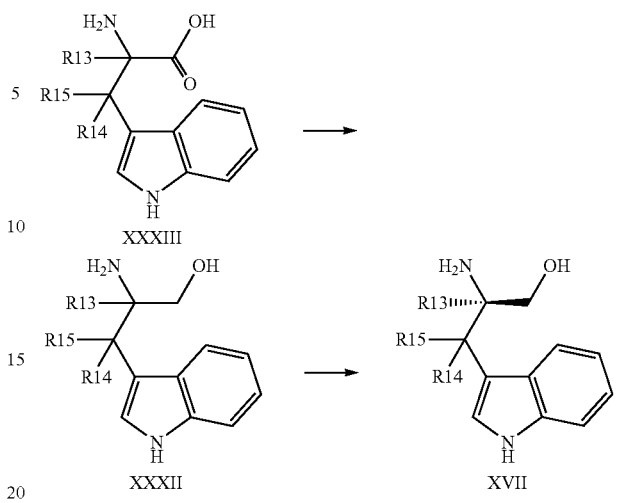

Tryptophanol derivatives of general structure XVII are either commercially available, or may be prepared in a sequence of reaction steps from commercially available 3-cyanomethyl indole XXXIX. Optically pure tryptophanols VII may be prepared from their corresponding diastereomeric mixtures XXXII using chiral separation technologies such as HPLC with chiral columns, well known to those of skill in the art. The tryptophanols XXXII are accessible from their corresponding amino acid precursors XXXIII using reducing agents such as borane complexes or LiAlH$_4$. In turn, amino acids XXXIII can be obtained from their N-butoxycarbonyl (Boc)-protected precursors XXXIV by treatment with strong acids such as trifluoroacetic acid or HCl. The required amino acid framework in derivatives XXXIV is obtained after basic hydrolysis of hydantoins XXXV. Typical conditions for this conversion are Ba(OH)$_2$ under elevated pressure and at increased temperature. The hydantoin moiety in XXXV can be introduced by treating aldehydes or ketones XXXVI with ammonium carbonate in the presence of potassium cyanide.

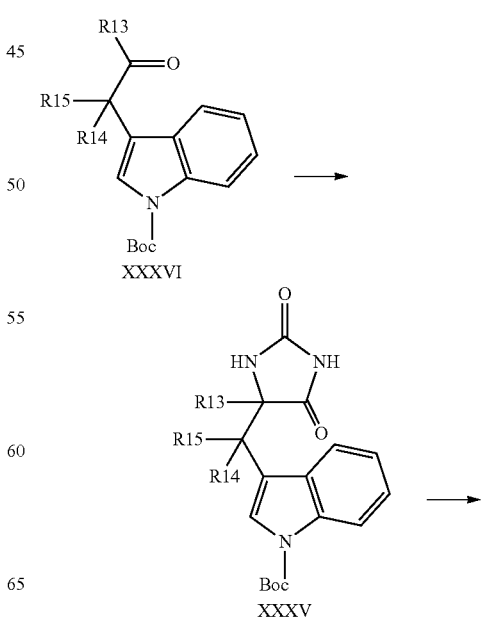

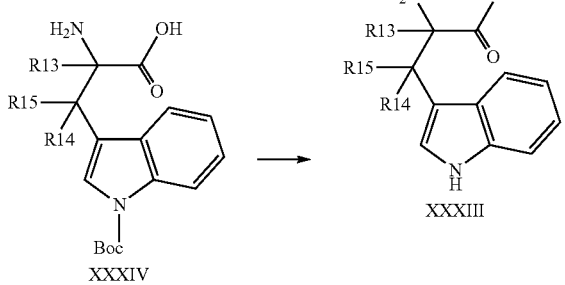

Aldehydes XXXVI-a, in which R13=H may be obtained by partial reduction of cyanides XXXVII using DIBAL-H in toluene at low temperature (−50° C.). Ketones XXXVI-b are accessible from aldehydes XXXVI-a via a two-step procedure, well know to those skilled in the art. Thus, reaction of XXXVI-a with commercially available alkylmagnesium or alkyllithium reagents in the presence of copper salts (or, alternatively, with alkyl cuprates), followed by oxidation of the secondary alcohol moiety (using a variety of oxidation protocols such as Swern-type oxidation or Dess-Martin periodinane), gives access to XXXVI-b.

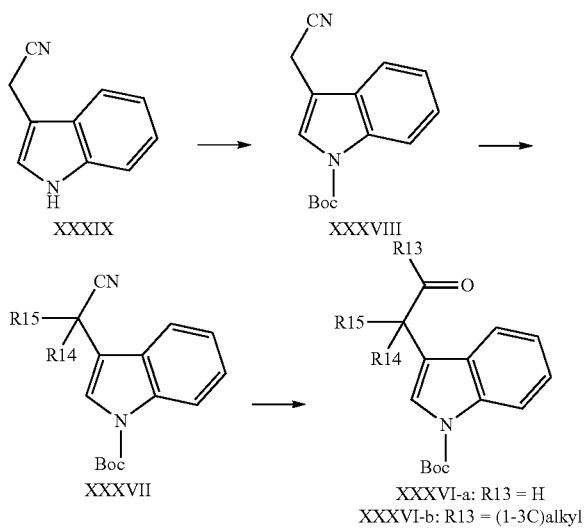

Cyanides XXXVII, in turn, may be prepared by single or double alkylation of cyanomethyl derivatives XXXVIII. In a typical procedure, a strong base such as NaH or LDA is used in an inert solvent such as diethyl ether with alkyl halides as alkyl donors. When alkyl dihalides such as 1,2-dichloroethane or 1,4-dibromobutane are used, R14 and R15 together form a cycloalkyl ring. XXXVIII is accessible by Boc-protection of commercially available XXXIX using methods well documented in literature. Typically, tert-butoxycarbonyl anhydride ($Boc_2O$) is used in an appropriate solvent such as dichloromethane in the presence of a suitable base such as triethyl amine (in combination with 4-dimethylamino pyridine, DMAP) to functionalize XXXIX with a Boc protective group, as described in: *Tetrahedron* 65, 9015-9020 (2009).

The compounds of the invention inhibit FSH receptor activity. All compounds of the invention have a pIC50 of 5 or higher. Preferred are compounds with a pIC50 of more than 7.

The invention is illustrated by the following examples.

EXAMPLES

General comments

The following abbreviations are used in the examples: DCM=dichloromethane, DMF=N,N-dimethylformamide, HCl=hydrogen chloride, $NaHCO_3$=sodium bicarbonate, $MgSO_4$=magnesium sulphate, THF=tetrahydrofuran, LiHMDS=Lithium bis(trimethylsilyl)amide, $Na_2SO_4$=sodium sulphate, DME=dimethoxyethane, LC-MS=liquid chromatography-mass spectrometry, HPLC=high-performance liquid chromatography, $CH_3CN$=acetonitrile, MeCN=acetonitrile, LDA=Lithium diisopropylamide, TMSCl=Trimethylsilyl chloride, Pd/C=palladium on carbon, HATU=2-(1H-7-Azabenzotriazol-1-yl)-1,1,3,3-tetramethyl uronium hexafluorophosphate, TLC=thin layer chromatography, OTBDMS=tert-butyldimethylsilylether, $CHCl_3$=chloroform, DMSO=dimethylsulfoxide The names of the final products described in the examples were generated using the convert name to structure tool in ChemDraw version 9.01.

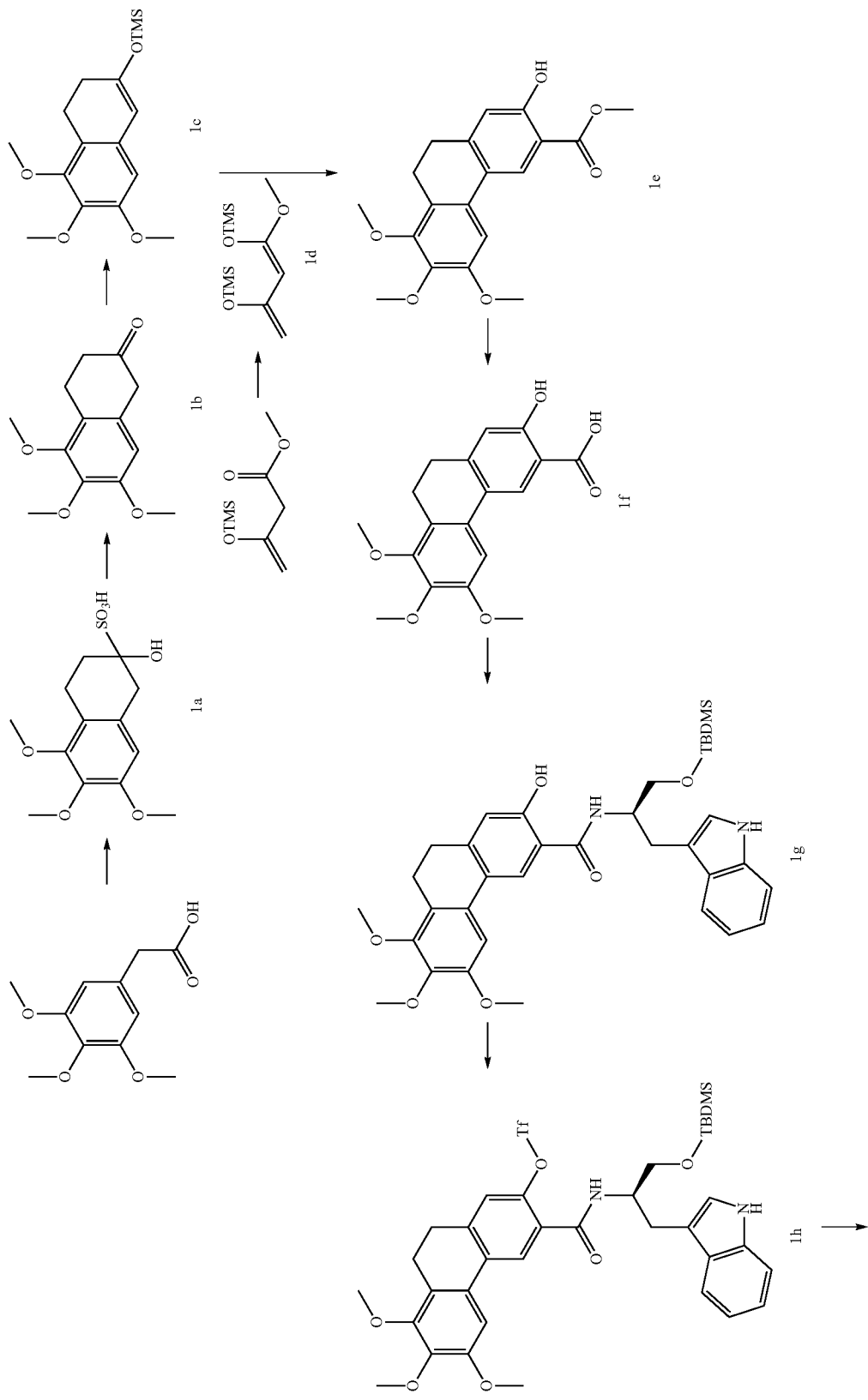

-continued
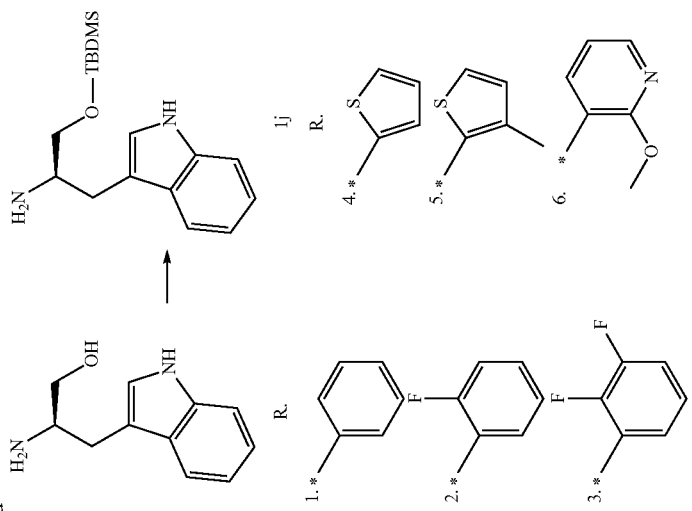
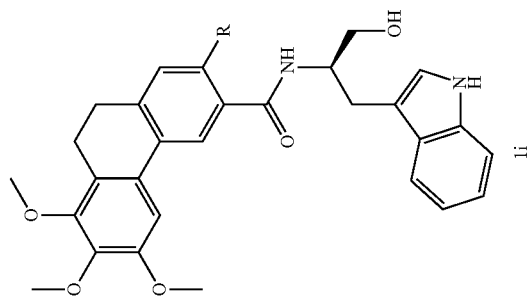

Example 1

(R)—N-(1-hydroxy-3-(1H-indol-3-yl)propan-2-yl)-6,7,8-trimethoxy-2-phenyl-9,10-dihydrophenanthrene-3-carboxamide

(a). 2-hydroxy-5,6,7-trimethoxy-1,2,3,4-tetrahydronaphthalene-2-sulfonic acid Oxalyl chloride (14.7 g) was added over 10 minutes to a solution of 3,4,5-trimethoxyphenylacetic acid (23.8 g) in DCM (400 ml) and DMF (5 drops). The mixture was stirred at ambient temperature for 18 hours. The solvents were removed under vacuum to give an orange oil which was redissolved in DCM (100 ml) and then added to a solution of aluminium chloride (43.3 g) in DCM (1.0 L) at 5° C. The mixture was stirred at 5° C. for 10 minutes before ethylene gas was gently bubbled through the mixture for 1 hour. The crude reaction mixture was poured on to ice/water and stirred vigorously for 20 minutes. The organic phase was separated and washed with a aqueous 2N HCl solution, saturated aqueous $NaHCO_3$ solution and brine, dried ($MgSO_4$) and filtered. The solvents were removed under vacuum to give a dark oil that was redissolved in ethyl acetate (60 ml). Sodium bisulfite (28.6 g) in water (60 ml) was added to the mixture, stirring for 18 hours. A precipitate was removed by filtration, washed with ethyl acetate and dried under vacuum.

Yield: 8.26 g $^1$H NMR δ (ppm) (DMSO-$d_6$): 9.92 (1H, s), 6.50 (1H, s), 4.75 (1H, s), 3.80-3.67 (9H, m), 3.15 (1H, d, J=17.11 Hz), 2.78-2.62 (2H, m), 2.09-2.01 (1H, m), 1.87-1.76 (1H, m), 1.31 (1H, s).

(b). 5,6,7-trimethoxy-3,4-dihydronaphthalen-2(1H)-one

A solution of 1N aqueous sodium bicarbonate solution (100 ml) was added to a solution of intermediate 1a (10.0 g) in ethyl acetate (300 ml) and stirred vigorously for 3 hours at room temperature. The organic phase was separated, dried over magnesium sulphate, filtered and then concentrated under vacuum.

Yield: 6.35 g $^1$H NMR δ (ppm) (CHCl$_3$-d): 6.46 (1H, s), 3.91-3.82 (9H, m), 3.62-3.40 (2H, m), 3.05 (2H, t, J=6.71 Hz), 2.55-2.48 (2H, m).

(c). trimethyl(5,6,7-trimethoxy-1,2,3,4-tetrahydronaphthalen-2-yloxy)silane n-Butyllithium (2.5 M solution in hexanes, 12.8 ml) was added dropwise to a 0° C. solution of diisopropylamine (3.20 g) in THF (105 ml) before cooling to −78° C. Intermediate 1b (4.95 g) was added to the solution of LDA at −78° C. The reaction mixture was stirred at this temperature for 2 hours. Chlorotrimethylsilane (3.46 g) was added to the reaction mixture at −78° C. and stirred for another 30 minutes before being allowed to warm to ambient temperature over 1 hour. The solvents were removed under vacuum to give a dark brown oil which was dissolved in iso-hexane The mixture was filtered through celite and the filter cake was washed through with iso-hexane. The combined filtrates were concentrated to dryness.

Yield: 6.13 g $^1$H NMR δ (ppm) (CHCl$_3$-d): 6.35-6.27 (1H, m), 5.63 (1H, s), 3.87-3.83 (9H, m), 2.88 (2H, t, J=8.36 Hz), 2.35-2.30 (2H, m), 0.30 (9H, t, J=3.40 Hz).

(d). (Z)-4-methoxy-2,2,8,8-tetramethyl-6-methylene-3,7-dioxa-2,8-disilanon-4-ene LiHMDS (45.3 ml, 1.0 M in THF) was added over 5 minutes to a −78° C. solution of methyl 3-(O-trimethylsilyl)buten-2-oate (6.09 g) in THF (61 ml). The orange solution was stirred at −78° C. for 1 hour then chlorotrimethylsilane (7.05 g) was added and the reaction mixture was stirred for a further 30 minutes. The reaction mixture was allowed to warm to ambient temperature over 1 hour before the solvents were removed under vacuum. The residue was triturated with iso-hexane and the liquors were filtered through celite and concentrated to dryness.

Yield: 11.79 g $^1$H NMR δ (ppm) (CHCl$_3$-d): 4.30 (1H, s), 3.97 (1H, d, J=1.38 Hz), 3.76 (1H, d, J=1.35 Hz), 3.38 (3H, s), 0.12-0.02 (9H, m), 0.04 (9H, s

(e). methyl 2-hydroxy-6,7,8-trimethoxy-9,10-dihydrophenanthrene-3-carboxylate Trimethylorthoformate (2.11 g) was dissolved in DCM (65 ml) and cooled to −78° C. Titanium tetrachloride (3.78 g) was added and the yellow mixture was stirred for 5 minutes at −78° C. before the addition of a −78° C. solution of intermediate 1c (6.13 g) in DCM (65 ml). The dark mixture was stirred at −78° C. for 2 hours, at which time a further aliquot of titanium tetrachloride (3.78 g) was added, followed by 1d (9.84 g). The dark mixture was stirred at −78° C. for 40 minutes then allowed to warm to room temperature over 1 hour. The reaction mixture was poured into a solution of saturated aqueous sodium bicarbonate and water, stirred for 10 minutes and filtered through celite. The filter pad was washed well with DCM and the filtrate layers were separated. The organic phase was passed through a hydrophobic frit and concentrated under vacuum to give a dark red oil that was purified by chromatography on silica gel, eluting with petrol and increasing amounts of ethyl acetate.

Yield: 3.25 g

MS (ESI) m/z: 345 (M+H)$^+$.

$^1$H NMR δ (ppm) (CHCl$_3$-d): 10.78 (1H, s), 8.09 (1H, s), 7.05 (1H, s), 6.89 (1H, s), 4.04-3.86 (12H, m), 2.83 (4H, s).

(f). 2-hydroxy-6,7,8-trimethoxy-9,10-dihydrophenanthrene-3-carboxylic acid

Sodium hydroxide (15 ml, 2N) was added to a solution of intermediate 1e (3.25 g) in ethanol (65 ml) and the mixture was heated to 85° C. for 1 hour. The solvents were removed under vacuum to give a dark oil that was partitioned between ethyl acetate and a aqueous 1N HCl solution. The organic phase was passed through a hydrophobic frit before concentrating under vacuum.

Yield: 3.27 g.

MS (ESI) m/z: 331 (M+H)$^+$.

$^1$H NMR δ (ppm) (CHCl$_3$-d): 10.47 (1H, s), 8.17 (1H, s), 7.08-7.04 (1H, m), 6.92-6.87 (1H, m), 4.05-3.82 (9H, m), 2.87-2.81 (4H, m), 2.16 (1H, s).

(g). (R)—N-(1-(tert-butyldimethylsilyloxy)-3-(1H-indol-3-yl)propan-2-yl)-2-hydroxy-6,7,8-trimethoxy-9,10-dihydrophenanthrene-3-carboxamide 1-Ethyl-3-(3-dimethylaminopropyl)carbodiimide hydrochloride (2.70 g) was added to a solution of intermediate 1f (3.10 g) and 2-hydroxypyridine-N-oxide (1.57) in DMF (60 ml). The mixture was stirred at room temperature for 2 hours before the addition of compound 1j (2.86 g) in one portion. The mixture was stirred for a further hour and then a solution of water and aqueous saturated sodium bicarbonate solution was added over 45 minutes. The mixture was stirred for a further 45 minutes before a solid was collected by filtration through a sinter. The collected solid was washed with water and dried in air overnight.

Yield: 1.40 g.
MS (ESI) m/z: 617 (M+H)$^+$.
$^1$H NMR δ (ppm) (CHCl$_3$-d): 12.62 (1H, s), 8.06 (1H, s), 7.85 (1H, d, J=7.86 Hz), 7.45 (1H, s), 7.40 (1H, d, J=8.05 Hz), 7.27-7.10 (3H, m), 6.89 (2H, d, J=6.41 Hz), 6.79 (1H, d, J=8.43 Hz), 4.59 (1H, d, J=7.87 Hz), 3.97-3.86 (9H, m), 3.78 (1H, dd, J=9.92, 2.83 Hz), 3.73-3.67 (1H, m), 3.28-3.11 (2H, m), 2.91-2.74 (4H, m), 1.05-0.89 (9H, m), 0.12 (6H, d, J=5.83 Hz).

(h). (R)-3-(1-(tert-butyldimethylsilyloxy)-3-(1H-indol-3-yl)propan-2-ylcarbamoyl)-6,7,8-trimethoxy-9,10-dihydrophenanthren-2-yl trifluoromethanesulfonate Triethylamine (0.41 g) was added to a 0° C. solution of intermediate 1 g (1.25 g) in DCM (65 ml). Trifluoromethanesulfonic anhydride (0.74 g) was added over 2 minutes at 0° C. and the orange solution was allowed to warm to room temperature over 30 minutes. Saturated aqueous sodium bicarbonate solution was added to the mixture and stirred at room temperature for 15 minutes. The organic phase was separated and dried by passing through a hydrophobic frit. The solvents were removed under vacuum to give an orange oil that was purified by chromatography on silica gel, eluting with petrol and increasing amounts of ethyl acetate.

Yield: 1.14 g.
MS (ESI) m/z: 749 (M+H)$^+$.
$^1$H NMR δ (ppm) (CHCl$_3$-d): 8.08 (1H, s), 8.02 (1H, s), 7.91 (1H, d, J=7.81 Hz), 7.38 (1H, d, J=8.00 Hz), 7.25-7.09 (5H, m), 6.71 (1H, d, J=8.04 Hz), 4.55 (1H, s), 3.95 (6H, d, J=1.43 Hz), 3.90 (3H, s), 3.75 (1H, dd, J=10.02, 2.52 Hz), 3.69-3.64 (1H, m), 3.26-3.22 (1H, m), 3.19-3.14 (1H, m), 2.88 (4H, s), 0.96 (9H, s), 0.09 (6H, d, J=8.77 Hz).

(i). (R)—N-(1-hydroxy-3-(1H-indol-3-yl)propan-2-yl)-6,7,8-trimethoxy-2-phenyl-9,10-dihydrophenanthrene-3-carboxamide Tetrakis(triphenylphosphine) palladium(0) (12.3 g) was added to a degassed solution of intermediate 1h (75 mg), potassium carbonate (26.6 mg) and phenylboronic acid (14.5 mg) in a 10:1 mixture of 1,2-dimethoxymethane:water (1.54 ml) under nitrogen. The reaction mixture was degassed with nitrogen gas for a further 15 minutes before sealing and heating to 90° C. for 18 hours. The dark reaction mixture was partitioned between ethyl acetate and water and filtered through celite. The filtrate layers were separated and the aqueous phase was re-extracted with ethyl acetate. The combined organics were dried over magnesium sulphate, filtered and concentrated to dryness under vacuum, yielding a dark brown oil. The crude oil was redissolved in THF (2 ml) before the addition of tetrabutylammonium fluoride (1N in THF, 0.3 ml, 0.30 mmol), stirring for 2 hours. The solvents were removed under vacuum and the residue was then partitioned between ethyl acetate and water. The aqueous phase was re-extracted with and the combined organics were dried by passing through a hydrophobic frit. The solvents were removed under vacuum to give a dark brown oil that was purified by chromatography on silica gel, eluting with petrol and increasing amounts of ethyl acetate.

Yield: 47 mg
MS (ESI) m/z: 563 (M+H)$^+$.
$^1$H NMR δ (ppm)(CHCl$_3$-d): 8.00 (1H, s), 7.99 (1H, s), 7.70-7.64 (1H, m), 7.57-7.51 (1H, m), 7.50-7.32 (6H, m), 7.21-7.15 (2H, m), 7.09 (1H, ddd, J=8.02, 6.95, 0.99 Hz), 6.83 (1H, d, J=2.31 Hz), 5.54 (1H, d, J=7.55 Hz), 4.30-4.21 (1H, m), 3.96 (3H, s), 3.94 (3H, s), 3.89 (3H, s), 3.44-3.37 (2H, m), 2.89-2.79 (4H, m), 2.71 (2H, d, J=7.02 Hz), 2.00 (1H, t, J=5.80 Hz).

(j). (R)-1-(tert-butyldimethylsilyloxy)-3-(1H-indol-3-yl)propan-2-amine

To a solution of D-Tryptophanol (1.024 g) and imidazole (403 mg) in DCM (40 ml) and THF (8 ml) was added a solution of tert-butyldimethylsilyl chloride (0.852 g) in DCM (5 ml) dropwise. The reaction was allowed to warm to room temperature overnight. The reaction mixture was quenched with a saturated aqueous NaHCO$_3$ solution and the reaction mixture was extracted with dichloromethane. The aqueous phase was washed with dichloromethane and the combined organic layers were washed with brine, dried (MgSO$_4$), filtered and concentrated in vacuo. The residue was purified by chromatography on silica gel eluting with heptane and increasing amounts of ethyl acetate.

Yield: 1.11 g.
MS (ESI) m/z: 305 (M+H)$^+$.

Example 2

2-(2-fluorophenyl)-N—((R)-1-hydroxy-3-(1H-indol-3-yl)propan-2-yl)-6,7,8-trimethoxy-9,10-dihydrophenanthrene-3-carboxamide Compound 2 was prepared in an analogous fashion as described for example 1.
MS (ESI) m/z: 581 (M+H)$^+$.
$^1$H NMR δ (ppm)(CHCl$_3$-d): 8.02 (2H, d, J=9.40 Hz), 7.69-7.62 (1H, m), 7.58-7.42 (2H, m), 7.36-7.26 (2H, m), 7.22-7.04 (5H, m), 6.91 (1H, d, J=2.33 Hz), 5.74 (1H, d, J=7.32 Hz), 4.31-4.24 (1H, m), 3.94 (6H, s), 3.88 (3H, s), 3.50-3.45 (2H, m), 2.86 (4H, s), 2.77 (2H, d, J=6.99 Hz), 2.29-2.23 (1H, m).

Example 3

2-(2,3-difluorophenyl)-N—((R)-1-hydroxy-3-(1H-indol-3-yl)propan-2-yl)-6,7,8-trimethoxy-9,10-dihydrophenanthrene-3-carboxamide Compound 3 was prepared in an analogous fashion as described for example 1.
MS (ESI) m/z: 599 (M+H)$^+$.
$^1$H NMR δ (ppm)(CHCl$_3$-d): 8.05 (1H, s), 7.95 (1H, s), 7.70-7.52 (2H, m), 7.35 (1H, d, J=8.13 Hz), 7.20 (2H, t, J=7.89 Hz), 7.12-6.98 (4H, m), 6.93 (1H, d, J=2.28 Hz), 5.81 (1H, d, J=7.19 Hz), 4.32-4.25 (1H, m), 3.94 (6H, d, J=3.25 Hz), 3.89 (3H, s), 3.54 (2H, t, J=4.84 Hz), 2.88-2.80 (6H, m), 2.41 (1H, t, J=5.43 Hz).

Example 4

(R)—N-(1-hydroxy-3-(1H-indol-3-yl)propan-2-yl)-6,7,8-trimethoxy-2-(thiophen-2-v)-9,10-dihydrophenanthrene-3-carboxamide Compound 4 was prepared in an analogous fashion as described for example 1.
MS (ESI) m/z: 569 (M+H)$^+$.

$^1$H NMR δ (ppm)(CHCl$_3$-d): 8.11 (1H, s), 7.88 (1H, s), 7.68-7.50 (3H, m), 7.45 (1H, td, J=7.60, 2.86 Hz), 7.21-7.05 (4H, m), 7.01 (1H, dd, J=5.13, 3.52 Hz), 6.87 (1H, d, J=2.30 Hz), 5.88 (1H, d, J=7.42 Hz), 4.37-4.28 (1H, m), 3.93 (6H, s), 3.88 (3H, s), 3.62-3.49 (2H, m), 2.87-2.80 (6H, m), 2.40 (1H, t, J=5.67 Hz).

Example 5

N—((R)-1-hydroxy-3-(1H-indol-3-yl)propan-2-yl)-6,7,8-trimethoxy-2-(3-methylthiophen-2-yl)-9,10-dihydrophenanthrene-3-carboxamide Compound 5 was prepared in an analogous fashion as described for example 1.
MS (ESI) m/z: 583 (M+H)$^+$.
$^1$H NMR δ (ppm)(CHCl$_3$-d): 8.16 (1H, s), 8.07 (1H, s), 7.61 (1H, d, J=7.90 Hz), 7.33 (1H, t, J=8.09 Hz), 7.27-7.23 (1H, m), 7.21-7.15 (3H, m), 7.10 (1H, t, J=7.50 Hz), 6.95 (1H, d, J=52.28 Hz), 6.90 (1H, d, J=5.12 Hz), 5.87 (1H, d, J=7.51 Hz), 4.36-4.28 (1H, m), 3.95 (3H, s), 3.94 (3H, s), 3.89 (3H, s), 3.55-3.41 (2H, m), 2.98-2.75 (4H, m), 2.76 (2H, d, J=7.18 Hz), 2.25 (1H, s), 2.08 (3H, s).

Example 6

N—((R)-1-hydroxy-3-(1H-indol-3-yl)propan-2-yl)-6,7,8-trimethoxy-2-(2-methoxypyrdin-3-v)-9,10-dihydrophenanthrene-3-carboxamide Compound 6 was prepared in an analogous fashion as described for example 1.
MS (ESI) m/z: 594 (M+H)$^+$.
$^1$H NMR δ (ppm)(CHCl$_3$-d): 8.15 (1H, dd, J=5.03, 1.89 Hz), 8.01 (2H, s), 7.60 (1H, d, J=7.92 Hz), 7.49 (1H, dd, J=7.19, 1.93 Hz), 7.34 (1H, t, J=8.13 Hz), 7.21-7.14 (2H, m), 7.12-7.07 (2H, m), 6.92-6.88 (2H, m), 5.96 (1H, d, J=7.33 Hz), 4.28-4.24 (1H, m), 3.96-3.87 (12H, m), 3.45 (2H, s), 2.85 (4H, s), 2.76 (2H, d, J=7.04 Hz), 2.32 (1H, s).

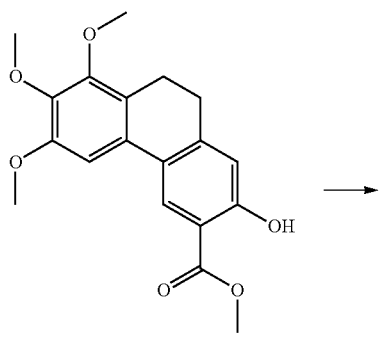

Example 7

(R)—N-(1-hydroxy-3-(1H-indol-3-yl)propan-2-yl)-2-isopropoxy-6,7,8-trimethoxy-9,10-dihydrophenanthrene-3-carboxamide (a). methyl 2-isopropoxy-6,7,8-trimethoxy-9,10-dihydrophenanthrene-3-carboxylate 2-Bromopropane (60 mg) was added to a solution of intermediate 1e (100 mg) and potassium carbonate (126 mg) in DMF (1 ml) and the mixture was then heated to 90° C. for 18 hours. The solvents were removed under vacuum and the residue was partitioned between ethyl acetate and water. The aqueous phase was re-extracted with ethyl acetate and the combined organics were washed with water, dried over Na$_2$SO$_4$, filtered and concentrated to dryness under vacuum.
Yield: 100 mg
$^1$H NMR δ (ppm) (CHCl$_3$-d): 8.06 (1H, s), 7.05 (1H, s), 6.92-6.82 (1H, m), 4.67-4.52 (1H, m), δ 3.96-3.85 (12H, m), 2.82 (4H, t, J=5.92 Hz), 1.42-1.36 (6H, m).

(b). 2-isopropoxy-6,7,8-trimethoxy-9,10-dihydrophenanthrene-3-carboxylic acid

Sodium hydroxide (0.5 ml, 2 N in water) was added to a solution of intermediate 7a (100 mg) in ethanol (2 ml) and the mixture was then heated to 80° C. for 18 hours. The solvents were removed under vacuum and the residue was partitioned between ethyl acetate and a aqueous 1N HCl solution. The aqueous phase was re-extracted with ethyl acetate and the

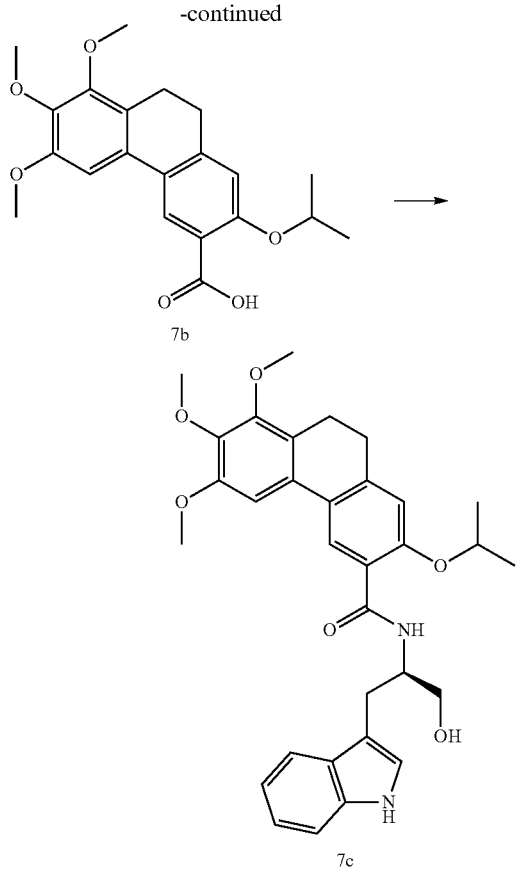

combined organics were washed with water, dried over Na₂SO₄, filtered and concentrated to dryness under vacuum.

Yield: 78 mg

¹H NMR δ (ppm) (CHCl₃-d): 8.46 (1H, s), 7.12 (1H, s), 6.96-6.90 (1H, m), 4.95-4.86 (1H, m), 3.98-3.83 (9H, m), 2.85 (4H, s), 1.52 (6H, d, J=6.11 Hz).

(c). (R)—N-(1-hydroxy-3-(1H-indol-3-yl)propan-2-yl)-2-isopropoxy-6,7,8-trimethoxy-9,10-dihydro-phenanthrene-3-carboxamide 1-Ethyl-3-(3-dimethylaminopropyl)carbodiimide hydrochloride (60 mg) was added to a solution of intermediate 7b (78 mg), 1-hydroxybenzotriazole (29 mg) and diisopropyl-ethylamine (67 mg) in DMF (2 ml). The reaction mixture was stirred for 30 minutes before the addition of D-tryptophanol-OTBDMS (70 mg). The reaction mixture was stirred for another 18 hours. The reaction mixture was partitioned between ethyl acetate and water and the aqueous phase was re-extracted with ethyl acetate. The combined organics were washed with water, dried over sodium sulphate, filtered and concentrated to dryness under. The crude oil was dissolved in THF (1 ml) before the addition of tetrabutylammonium fluoride (1N in THF, 0.5 ml) and stirred for 72 hours. The reaction mixture was partitioned between ethyl acetate and water. The aqueous phase was re-extracted with ethyl acetate and the combined organics were washed with water, dried over sodium sulphate, filtered and concentrated to dryness under vacuum. The crude residue was purified by chromatography on silica gel with petrol and increasing amounts of ethyl acetate.

Yield: 75 mg

MS (ESI) m/z: 545 (M+H)⁺.

¹H NMR δ (ppm) (CHCl₃-d): 8.63-8.53 (2H, m), 8.08 (1H, s), 7.72 (1H, d, J=7.86 Hz), 7.36 (1H, d, J=8.07 Hz), 7.22-7.07 (4H, m), 6.80 (1H, s), 4.73-4.64 (1H, m), 4.57 (1H, s), 3.94 (3H, s), 3.91 (3H, s), 3.87 (3H, s), 3.85-3.80 (1H, m), 3.80-3.72 (1H, m), 3.22-3.07 (2H, m), 2.90-2.73 (4H, m), 2.73 (1H, s), 1.29 (3H, d, J=6.04 Hz), 1.23 (3H, d, J=6.04 Hz).

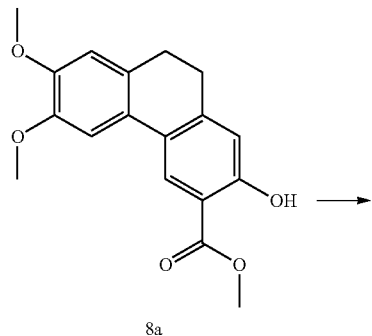

8a

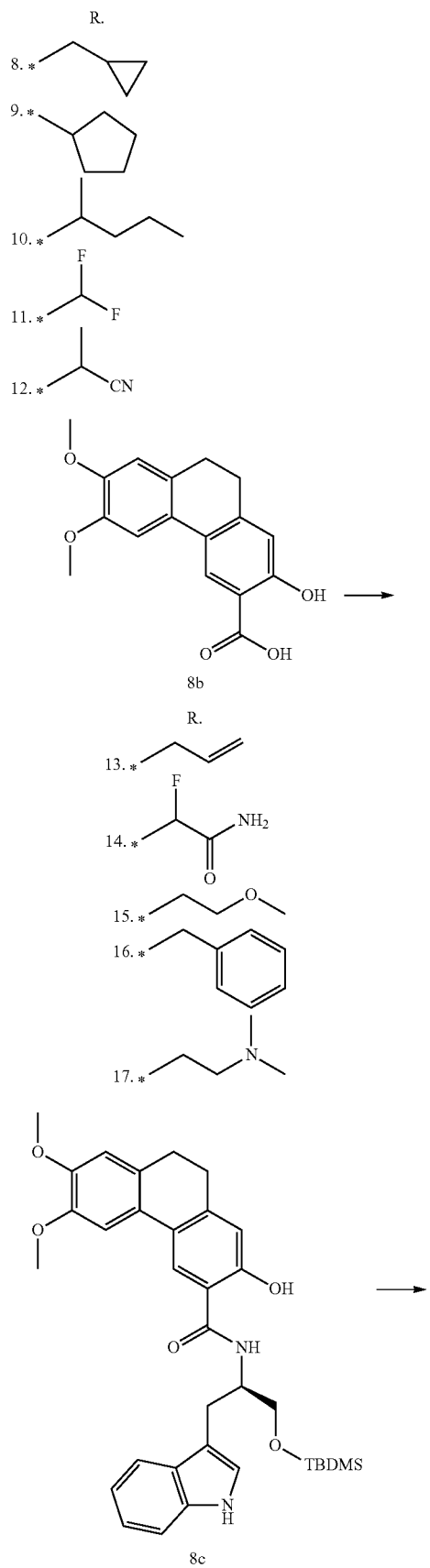

-continued

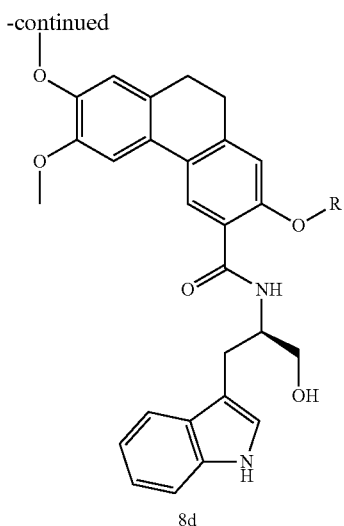

8d

Example 8

(R)-2-(cyclopropylmethoxy)-N-(1-hydroxy-3-(1H-indol-3-yl)propan-2-yl)-6,7-dimethoxy-9,10-dihydrophenanthrene-3-carboxamide

(a). methyl 2-hydroxy-6,7-dimethoxy-9,10-dihydrophenanthrene-3-carboxylate

Compound 8a was prepared in analogous fashion as described for compound 1e, but starting from 2-(3,4-dimethoxyphenyl)acetic acid.

(b). 2-hydroxy-6,7-dimethoxy-9,10-dihydrophenanthrene-3-carboxylic acid

To a solution of 8a (5.7 g) in THF (100 ml) at room temperature was added lithium hydroxide hydrate (7.0 g) in water (100 ml). The mixture was heated to 50° C. for 3 hours before being allowed to cool to room temperature. The pH was adjusted to pH 1 with a aqueous 1N HCl solution and the product was extracted into ethyl acetate. The aqueous phase was re-extracted with ethyl acetate and the combined organics were dried over Na$_2$SO$_4$, filtered and concentrated in vacuo. Trituration with ethyl acetate yielded a pale brown solid.

Yield: 5.07 g
$^1$H NMR δ (ppm)(CHCl$_3$-d): 10.39 (1H, s), 8.17 (1H, s), 7.25 (1H, s), 6.92 (1H, s), 6.77 (1H, s), 4.01 (3H, s), 3.94 (3H, s), 2.94-2.80 (4H, m).

(c). (R)—N-(1-(tert-butyldimethylsilyloxy)-3-(1H-indol-3-yl)propan-2-yl)-2-hydroxy-6,7-dimethoxy-9,10-dihydrophenanthrene-3-carboxamide 1-Ethyl-3-(3-dimethylaminopropyl)carbodiimide hydrochloride (4.23 g) was added to a solution of intermediate acid 8b (5.30 g,) and 2-hydroxypyridine-N-oxide (2.45 g) in DMF (55 ml). The reaction was stirred for 2.5 hours before the addition of compound 1j (5.36 g) in one portion. The mixture was stirred at room temperature for a further 1 hour, before the addition of a mixture of saturated sodium bicarbonate solution (20 ml) in water (150 ml) over 45 minutes. The mixture was stirred at room temperature for 45 minutes causing precipitation of a white solid that was removed by filtration, washed with water and dried under vacuum.

Yield: 10 g
$^1$H NMR δ (ppm)(CHCl$_3$-d): 12.59 (1H, s), 8.06 (1H, s), 7.85 (1H, d, J=7.85 Hz), 7.45-7.36 (2H, m), 7.26-7.10 (3H, m), 7.06 (1H, s), 6.89 (1H, s), 6.85-6.75 (2H, m), 4.61-4.55 (1H, m), 3.94 (6H, d, J=1.68 Hz), 3.78 (1H, dd, J=10.05, 2.74 Hz), 3.73-3.67 (1H, m), 3.28-3.11 (2H, m), 2.87-2.78 (4H, m), 0.99 (8H, s), 0.12 (6H, d, J=6.06 Hz).

(d). (R)-2-(cyclopropylmethoxy)-N-(1-hydroxy-3-(1H-indol-3-yl)propan-2-yl)-6,7-dimethoxy-9,10-dihydrophenanthrene-3-carboxamide Methylcyclopropyl bromide (14.4 mg) was added to a solution of intermediate 1c (50 mg) and potassium carbonate (11.8 mg) in DMF (1 ml). The reaction mixture was stirred at room temperature for 48 hours. The reaction mixture was partitioned between water and ethyl acetate. The organic phase was separated and washed with water, dried (MgSO$_4$), filtered and concentrated under vacuum to give a brown oil. The crude oil was dissolved in THF (0.8 ml) before the addition of a 1N solution of tetrabutylammonium fluoride in THF (150 μL) and stirred for 2 hours. The reaction mixture was partitioned between water and ethyl acetate and the organic phase was separated, passed through a hydrophobic frit and then concentrated in vacuo. The crude residue was purified by preparative HPLC, eluting with water and increasing amounts of acetonitrile.

Yield: 39 mg
MS (ESI) m/z: 527 (M+H)$^+$.
$^1$H NMR δ (ppm)(CHCl$_3$-d): 8.63 (1H, d, J=7.17 Hz), 8.54 (1H, s), 8.03 (1H, s), 7.69 (1H, d, J=7.88 Hz), 7.39-7.33 (2H, m), 7.22-7.16 (1H, m), 7.15-7.07 (2H, m), 6.73 (2H, d, J=2.80 Hz), 4.60 (1H, t, J=6.31 Hz), 3.97 (3H, s), 3.91 (3H, s), 3.89-3.74 (4H, m), 3.21-3.11 (2H, m), 2.86-2.77 (5H, m), 1.09-1.00 (1H, m), 0.56-0.50 (2H, m), 0.31-0.20 (2H, m).

Example 9

(R)-2-(cyclopentyloxy)-N-(1-hydroxy-3-(1H-indol-3-yl)propan-2-yl)-6,7-dimethoxy-9,10-dihydrophenanthrene-3-carboxamide Compound 9 was prepared in an analogous fashion as described for example 8.
MS (ESI) m/z: 541 (M+H)$^+$.
$^1$H NMR δ (ppm)(CHCl$_3$-d): 8.55 (1H, s), 8.50 (1H, d, J=7.38 Hz), 8.01 (1H, s), 7.72 (1H, d, J=7.88 Hz), 7.38-7.34 (2H, m), 7.22-7.17 (1H, m), 7.15-7.09 (2H, m), 6.79 (1H, s), 6.73 (1H, s), 4.92-4.87 (1H, m), 4.58 (1H, d, J=7.35 Hz), 3.97 (3H, s), 3.91 (3H, s), 3.86-3.81 (1H, m), 3.79-3.73 (1H, m), 3.18-3.12 (2H, m), 2.88-2.77 (4H, m), 2.67-2.63 (1H, m), 1.96-1.82 (3H, m), 1.75-1.55 (5H, m).

Example 10

N—((R)-1-hydroxy-3-(1H-indol-3-yl)propan-2-yl)-6,7-dimethoxy-2-(pentan-2-yloxy)-9,10-dihydrophenanthrene-3-carboxamide Compound 10 was prepared in an analogous fashion as described for example 8.
MS (ESI) m/z: 543 (M+H)$^+$.
$^1$H NMR δ (ppm)(CHCl$_3$-d): 8.62-8.53 (2H, m), 8.01 (1H, s), 7.72 (1H, d, J=7.87 Hz), 7.38-7.34 (2H, m), 7.22-7.17 (1H, m), 7.14 (1H, d, J=7.61 Hz), 7.11 (1H, s), 6.78 (1H, d, J=6.42 Hz), 6.73 (1H, s), 4.56 (2H, d, J=19.85 Hz), 3.97 (3H, s), 3.91

(3H, s), 3.87-3.82 (1H, m), 3.77 (1H, d, J=10.27 Hz), 3.18-3.12 (2H, m), 2.83 (4H, d, J=14.32 Hz), 2.72 (1H, d, J=5.54 Hz), 1.59-1.44 (4H, m), 1.28+1.17 (3H, 2×d, J=6.08 Hz), 0.94-0.82 (3H, m).

Example 11

(R)-2-(difluoromethoxy)-N-(1-hydroxy-3-(1H-indol-3-yl)propan-2-yl)-6,7-dimethoxy-9,10-dihydrophenanthrene-3-carboxamide Compound 11 was prepared in an analogous fashion as described for example 8.
MS (ESI) m/z: 523 (M+H)$^+$.
$^1$H NMR δ (ppm)(CHCl$_3$-d): 8.35 (1H, s), 8.07 (1H, s), 7.73 (1H, d, J=7.89 Hz), 7.38 (2H, d, J=7.82 Hz), 7.30 (1H, s), 7.24-7.17 (1H, m), 7.18-7.10 (2H, m), 6.96 (1H, s), 6.74 (1H, s), 6.28 (1H, t, J=72.98 Hz), 4.60-4.54 (1H, m), 3.96 (3H, s), 3.92 (3H, s), 3.90-3.82 (1H, m), 3.81-3.74 (1H, m), 3.16 (2H, d, J=7.04 Hz), 2.89-2.79 (4H, m), 2.67 (1H, t, J=5.37 Hz).

Example 12

2-(1-cyanoethoxy)-N—((R)-1-hydroxy-3-(1H-indol-3-yl)propan-2-yl)-6,7-dimethoxy-9,10-dihydrophenanthrene-3-carboxamide Compound 12 was prepared in an analogous fashion as described for example 8.
MS (ESI) m/z: 526 (M+H)$^+$.

Example 13

(R)-2-(allyloxy)-N-(1-hydroxy-3-(1H-indol-3-yl)propan-2-yl)-6,7-dimethoxy-9,10-dihydrophenanthrene-3-carboxamide Compound 13 was prepared in an analogous fashion as described for example 8.
MS (ESI) m/z: 513 (M+H)$^+$.

Example 14

2-(2-amino-1-fluoro-2-oxoethoxy)-N—((R)-1-hydroxy-3-(1H-indol-3-yl)propan-2-yl)-6,7-dimethoxy-9,10-dihydrophenanthrene-3-carboxamide Compound 14 was prepared in an analogous fashion as described for example 8.
MS (ESI) m/z: 548 (M+H)$^+$.

Example 15

(R)—N-(1-hydroxy-3-(1H-indol-3-yl)propan-2-yl)-6,7-dimethoxy-2-(2-methoxyethoxy)-9,10-dihydrophenanthrene-3-carboxamide Compound 15 was prepared in an analogous fashion as described for example 8.
MS (ESI) m/z: 531 (M+H)$^+$.

Example 16

(R)-2-(benzyloxy)-N-(1-hydroxy-3-(1H-indol-3-yl)propan-2-yl)-6,7-dimethoxy-9,10-dihydrophenanthrene-3-carboxamide Compound 16 was prepared in an analogous fashion as described for example 8.
MS (ESI) m/z: 563 (M+H)$^+$.

Example 17

(R)-2-(2-(dimethylamino)ethoxy)-N-(1-hydroxy-3-(1H-indol-3-yl)propan-2-yl)-6,7-dimethoxy-9,10-dihydrophenanthrene-3-carboxamide Compound 17 was prepared in an analogous fashion as described for example 8.
MS (ESI) m/z: 544 (M+H)$^+$.

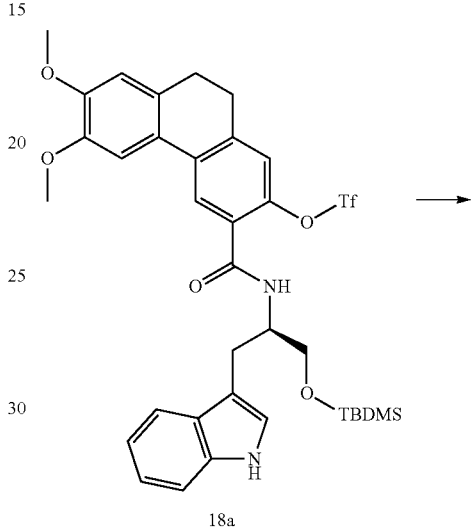

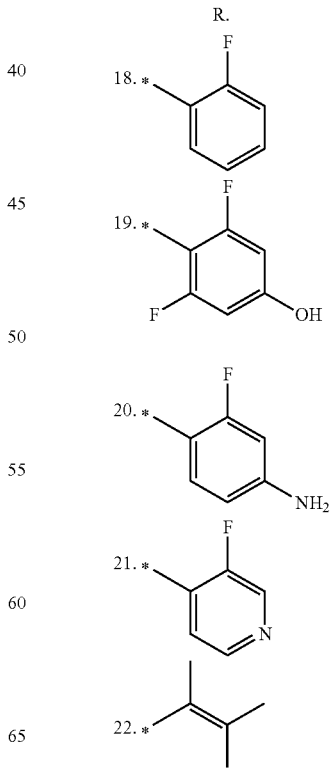

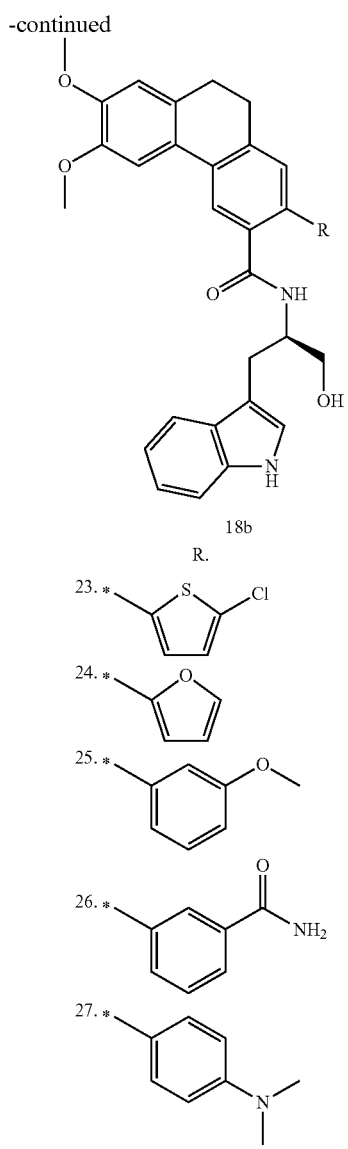

Example 18

2-(2-fluorophenyl)-N—((R)-1-hydroxy-3-(1H-indol-3-yl)propan-2-yl)-6,7-dimethoxy-9,10-dihydrophenanthrene-3-carboxamide (a). (R)-3-(1-(tert-butyldimethylsilyloxy)-3-(1H-indol-3-yl)propan-2-ylcarbamoyl)-6,7-dimethoxy-9,10-dihydrophenanthren-2-yl trifluoromethanesulfonate Compound 18a was prepared in analogous fashion as described for compound 1h, but starting from 2-(3,4-dimethoxyphenyl)acetic acid.

(b). 2-(2-fluorophenyl)-N—((R)-1-hydroxy-3-(1H-indol-3-yl)propan-2-yl)-6,7-dimethoxy-9,10-dihydrophenanthrene-3-carboxamide A solution of intermediate 18a (100 mg), 2-fluorophenylboronic acid (24 mg) and potassium carbonate (35 mg) in a 10:1 mixture of DME:water was degassed by bubbling through a gentle stream of nitrogen for 30 minutes. Tetrakis(triphenylphosphine)palladium(0) (16.2 mg) was added and the mixture was degassed for a further 15 minutes before sealing under nitrogen and heating to 90° C. for 16 hours. The solvents were removed under vacuum and the residue was redissolved in a solution of tetrabutylammonium fluoride (154 μl) in THF (1 ml). The mixture was stirred for 18 hours at ambient temperature and the solvents were then removed under vacuum. The residue was redissolved in DCM and washed with water. The organic phase was passed through a hydrophobic frit and concentrated under vacuum. The crude residue was purified by preparative HPLC, eluting with water and increasing amounts of acetonitrile.

Yield: 32 mg

MS (ESI) m/z: 551 (M+H)$^+$.

$^1$H NMR δ (ppm)(DMSO-$d_6$): 10.81 (1H, s), 8.01 (1H, d, J=8.2 Hz), 7.81 (1H, s), 7.63 (1H, d, J=7.9 Hz), 7.43 (1H, s), 7.40-7.29 (3H, m), 7.26 (1H, s), 7.23-7.10 (3H, m), 7.08 (1H, t, J=7.5 Hz), 7.02-6.94 (2H, m), 4.73 (1H, t, J=5.8 Hz), 4.08-4.01 (1H, m), 3.90 (3H, s), 3.85 (3H, s), 3.50-3.43 (1H, m), 3.36-3.34 (1H, m), 2.96 (1H, dd, J=14.6, 6.1 Hz), 2.90-2.78 (5H, m)

Example 19

(R)-2-(2,6-difluoro-4-hydroxyphenyl)-N-(1-hydroxy-3-(1H-indol-3-yl)propan-2-yl)-6,7-dimethoxy-9,10-dihydrophenanthrene-3-carboxamide Compound 19 was prepared in an analogous fashion as described for example 18.

MS (ESI) m/z: 585 (M+H)$^+$.

$^1$H NMR δ (ppm)(DMSO-$d_6$): 10.79 (1H, s), 7.97 (1H, d, J=8.19 Hz), 7.81 (1H, s), 7.61 (1H, d, J=7.85 Hz), 7.41 (1H, s), 7.31 (1H, d, J=8.06 Hz), 7.19-7.13 (2H, m), 7.04 (1H, t, J=7.55 Hz), 6.94 (2H, t, J=10.04 Hz), 6.45 (2H, t, J=9.29 Hz), 4.73 (1H, s), 4.07-3.99 (1H, m), 3.84 (6H, d, J=17.14 Hz), 3.46 (1H, dd, J=10.80, 4.96 Hz), 2.98 (1H, dd, J=14.51, 5.98 Hz), 2.86-2.75 (5H, m).

Example 20

2-(4-amino-2-fluorophenyl)-N—((R)-1-hydroxy-3-(1H-indol-3-yl)propan-2-yl)-6,7-dimethoxy-9,10-dihydrophenanthrene-3-carboxamide Compound 20 was prepared in an analogous fashion as described for example 18.

MS (ESI) m/z: 566 (M+H)$^+$.

$^1$H NMR δ (ppm)(CHCl$_3$-d): 8.05 (1H, s), 8.02 (1H, s), 7.58 (1H, d, J=7.9 Hz), 7.36 (1H, d, J=8.1 Hz), 7.31 (1H, s), 7.19 (1H, td, J=7.6, 1.1 Hz), 7.15-7.03 (3H, m), 6.92 (1H, d, J=2.3 Hz), 6.75 (1H, s), 6.40 (1H, dd, J=8.2, 2.3 Hz), 6.27 (1H, dd, J=11.7, 2.3 Hz), 5.78 (1H, d, J=7.4 Hz), 4.36-4.29 (1H, m), 3.96 (3H, s), 3.92 (3H, s), 3.74 (2H, s), 3.62-3.50 (2H, m), 2.89-2.76 (6H, m), 2.49 (1H, t, J=5.7 Hz).

Example 21

2-(3-fluoropyridin-4-yl)-N—((R)-1-hydroxy-3-(1H-indol-3-yl)propan-2-yl)-6,7-dimethoxy-9,10-dihydrophenanthrene-3-carboxamide Compound 21 was prepared in an analogous fashion as described for example 18.

MS (ESI) m/z: 552 (M+H)$^+$.

¹H NMR δ (ppm)(CHCl₃-d): 8.42 (1H, d, J=1.7 Hz), 8.37 (1H, d, J=4.9 Hz), 8.04 (1H, s), 7.86 (1H, s), 7.62 (1H, d, J=7.9 Hz), 7.37 (1H, d, J=8.1 Hz), 7.28-7.16 (4H, m), 7.12 (1H, dd, J=7.6, 1.0 Hz), 6.96 (1H, d, J=2.3 Hz), 6.77 (1H, s), 5.91 (1H, d, J=7.3 Hz), 4.37-4.31 (1H, m), 3.95 (3H, s), 3.94 (3H, s), 3.64-3.53 (2H, m), 2.99-2.81 (6H, m), 2.32 (1H, t, J=5.3 Hz).

Example 22

(R)—N-(1-hydroxy-3-(1H-indol-3-yl)propan-2-yl)-6,7-dimethoxy-2-(3-methylbut-2-en-2-yl)-9,10-dihydrophenanthrene-3-carboxamide Compound 22 was prepared in an analogous fashion as described for example 18.
MS (ESI) m/z: 525 (M+H)⁺.
¹H NMR δ (ppm) (DMSO-d₆): 10.84 (1H, s), 8.05-7.63 (1H, m), 7.71 (1H, d, J=7.9 Hz), 7.76-7.42 (1H, m), 7.38-7.33 (2H, m), 7.20 (1H, d, J=2.3 Hz), 7.09 (1H, t, J=7.5 Hz), 7.01 (1H, t, J=7.4 Hz), 6.95 (2H, d, J=2.4 Hz), 4.85 (1H, t, J=5.4 Hz), 4.24-4.16 (1H, m), 3.88 (3H, s), 3.83 (3H, s), 3.56-3.49 (1H, m), 3.45-3.34 (1H, m), 3.05-2.89 (2H, m), 2.79 (4H, s), 1.86 (3H, s), 1.71 (3H, s), 1.44 (3H, s).

Example 23

(R)-2-(5-chlorothiophen-2-yl)-N-(1-hydroxy-3-(1H-indol-3-yl)propan-2-yl)-6,7-dimethoxy-9,10-dihydrophenanthrene-3-carboxamide Compound 23 was prepared in an analogous fashion as described for example 18.
¹H NMR δ (ppm)(CHCl₃-d): 8.21 (1H, s), 7.78 (1H, s), 7.59 (1H, d, J=7.9 Hz), 7.33 (1H, d, J=8.1 Hz), 7.25-7.13 (3H, m), 7.09 (1H, t, J=3.8 Hz), 6.89 (1H, d, J=2.3 Hz), 6.79 (1H, d, J=3.8 Hz), 6.73 (1H, s), 6.70 (1H, d, J=3.8 Hz), 6.04 (1H, d, J=7.3 Hz), 4.41-4.31 (1H, m), 3.91-3.88 (6H, m), 3.62 (2H, d, J=4.5 Hz), 2.91 (2H, d, J=6.9 Hz), 2.87-2.75 (5H, m).

Example 24

(R)-2-(furan-2-yl)-N-(1-hydroxy-3-(1H-indol-3-yl)propan-2-yl)-6,7-dimethoxy-9,10-dihydrophenanthrene-3-carboxamide Compound 24 was prepared in an analogous fashion as described for example 18.
MS (ESI) m/z: 523 (M+H)⁺.

¹H NMR δ (ppm)(CHCl₃-d): 8.04 (1H, s), 7.69 (1H, s), 7.64 (1H, d, J=7.9 Hz), 7.45-7.42 (2H, m), 7.34 (1H, d, J=8.1 Hz), 7.23-7.15 (2H, m), 7.10 (1H, t, J=7.50 Hz), 6.98 (1H, d, J=2.3 Hz), 6.75 (1H, s), 6.60 (1H, d, J=3.4 Hz), 6.41 (1H, dd, J=3.4, 1.8 Hz), 5.98 (1H, d, J=7.3 Hz), 4.51-4.43 (1H, m), 3.93 (6H, d, J=8.0 Hz), 3.80-3.66 (2H, m), 3.08-2.96 (2H, m), 2.92-2.78 (4H, m), 2.65 (1H, t, J=5.5 Hz).

Example 25

(R)—N-(1-hydroxy-3-(1H-indol-3-v)propan-2-v)-6,7-dimethoxy-2-(3-methoxyphenyl)-9,10-dihydrophenanthrene-3-carboxamide Compound 25 was prepared in an analogous fashion as described for example 18.
MS (ESI) m/z: 563 (M+H)⁺.
¹H NMR δ (ppm)(CHCl₃-d): 7.99-7.94 (2H, m), 7.55 (1H, d, J=7.9 Hz), 7.35-7.27 (3H, m), 7.21-7.14 (2H, m), 7.09 (1H, t, J=7.5 Hz), 7.02-6.97 (2H, m), 6.90 (1H, dd, J=8.3, 2.5 Hz), 6.83 (1H, d, J=2.3 Hz), 6.76 (1H, s), 5.60 (1H, d, J=7.3 Hz), 4.28-4.23 (1H, m), 3.98 (3H, s), 3.93 (3H, s), 3.82 (3H, s), 3.51-3.41 (2H, m), 2.92-2.82 (4H, m), 2.73 (2H, d, J=7.03 Hz), 2.21 (1H, t, J=5.6 Hz)

Example 26

(R)-2-(3-carbamoylphenyl)-N-(1-hydroxy-3-(1H-indol-3-yl)propan-2-yl)-6,7-dimethoxy-9,10-dihydrophenanthrene-3-carboxamide Compound 26 was prepared in an analogous fashion as described for example 18.
MS (ESI) m/z: 576 (M+H)⁺.

Example 27

(R)-2-(4-(dimethylamino)phenyl)-N-(1-hydroxy-3-(1H-indol-3-yl)propan-2-yl)-6,7-dimethoxy-9,10-dihydrophenanthrene-3-carboxamide Compound 27 was prepared in an analogous fashion as described for example 18.
MS (ESI) m/z: 576 (M+H)⁺.

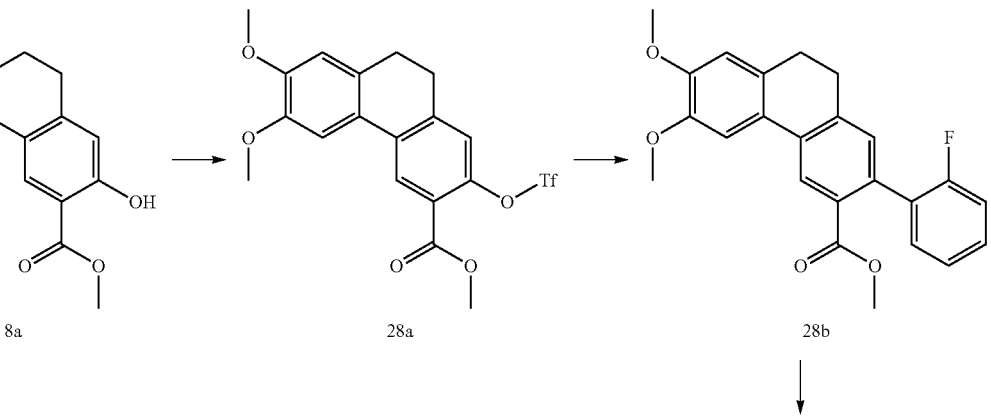

8a     28a     28b

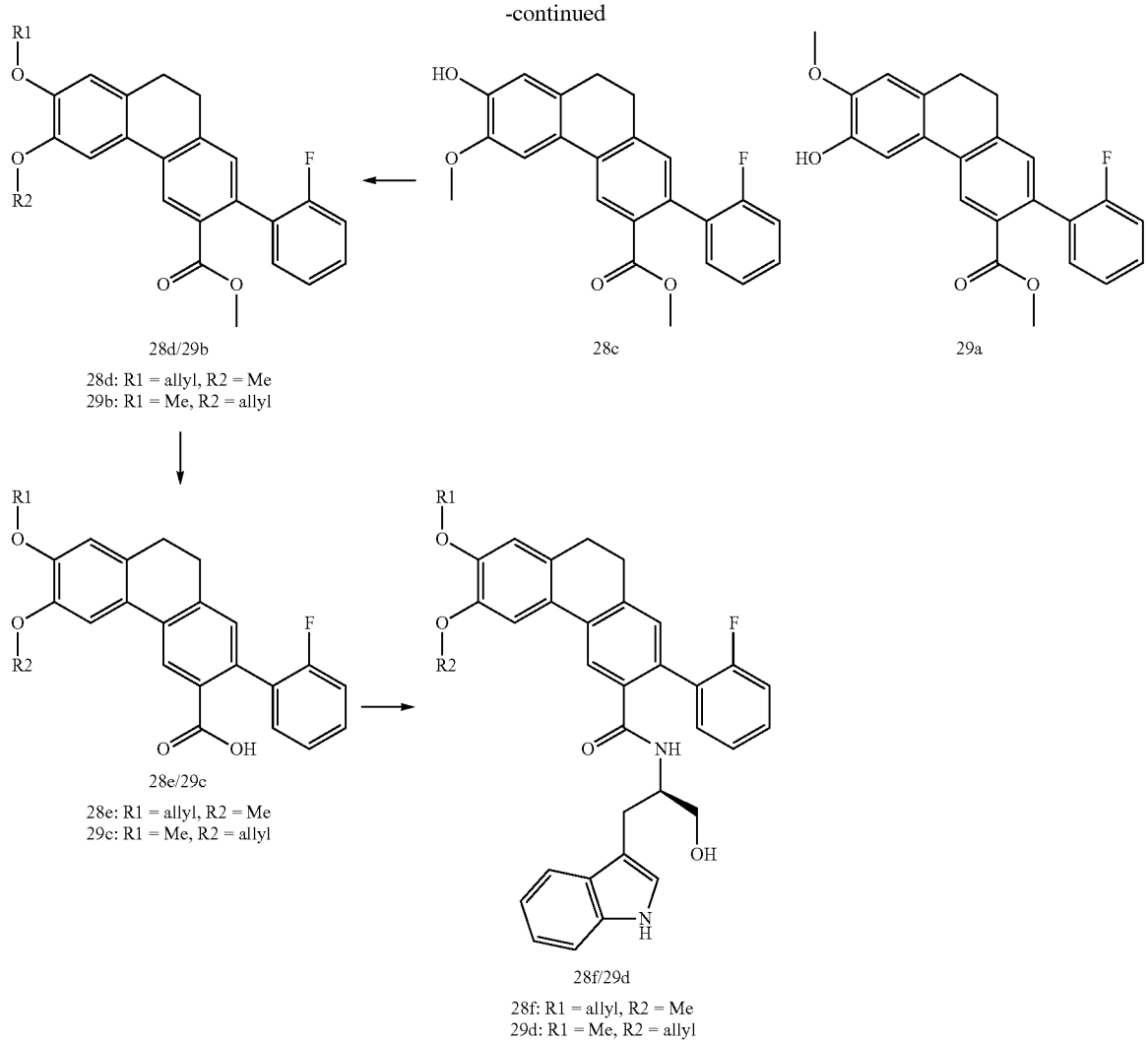

Example 28/29

7-(allyloxy)-2-(2-fluorophenyl)-N—((R)-1-hydroxy-3-(1H-indol-3-yl)propan-2-yl)-6-methoxy-9,10-dihydrophenanthrene-3-carboxamide/6-(allyloxy)-2-(2-fluorophenyl)-N—((R)-1-hydroxy-3-(1H-indol-3-yl)propan-2-yl)-7-methoxy-9,10-dihydrophenanthrene-3-carboxamide (a). methyl 6,7-dimethoxy-2-(trifluoromethylsulfonyloxy)-9,10-dihydrophenanthrene-3-carboxylate Trifluoromethanesulfonic acid anhydride (0.7 ml) was added dropwise to a 0° C. stirred solution of intermediate 8a (1 g) and triethylamine (0.89 ml) in DCM (10 ml). The reaction mixture was stirred for 1.5 hours. A saturated aqueous sodium bicarbonate solution was added and the mixture was thoroughly stirred. The phases were separated and the aqueous layer was re-extracted with DCM. The combined organics were washed with water and brine and dried by passing through a hydrophobic frit. The solvents were removed under vacuum to give a dark brown oil which was purified chromatography on silica gel, eluting with petrol and increasing amounts of ethyl acetate.

Yield: 1.4 g $^1$H NMR δ (ppm)(CHCl$_3$-d): 8.28 (1H, s), 7.3 (1 h, S), 7.13 (1H, s), 6.76 (1H, s), 3.99 (6H, 2s), 3.93 (3H, s), 2.95-2.81 (4H, m)

(b). methyl 2-(2-fluorophenyl)-6,7-dimethoxy-9,10-dihydrophenanthrene-3-carboxylate 2-Fluorophenyl boronic acid (94 mg) and potassium carbonate (112 mg) were added to a thoroughly de-oxygenated solution of intermediate 28a (200 mg) in dioxane (3 ml) and water (0.3 ml). After flushing with nitrogen, tetrakis(triphenylphosphine) palladium(0) (34 mg) was added and the reaction mixture was degassed for a further 60 seconds before sealing and heating to 80° C. for 18 hrs. The reaction mixture was partitioned between water and ethyl acetate. The aqueous phase was separated and re-extracted with ethyl acetate. The combined organics were washed with water and brine before drying by passing through a hydrophobic frit. The solvents were removed under vacuum to yield a crude oil which was purified by chromatography on silica gel, eluting with petrol and increasing amounts of ethyl acetate.

Yield: 164 mg

¹H NMR δ (ppm)(CHCl₃-d): 8.23 (1H, s), 7.38-7.3 (3H, m), 7.22-7.20 (2H, m), 7.16-7.05 (1H, m), 6.77 (1H, s), 4.00 (3H, s), 3.93 (3H, s), 3.73-3.69 (3H, m), 2.95-2.82 (4H, m), (28c/29a). methyl 2-(2-fluorophenyl)-7-hydroxy-6-methoxy-9,10-dihydrophenanthrene-3-carboxylate/ methyl 2-(2-fluorophenyl)-6-hydroxy-7-methoxy-9,10-dihydrophenanthrene-3-carboxylate Aluminium trichloride (100 mg) was added to a solution of intermediate 28b in dichloroethane (2 ml) and heated to 50° C. for 18 hours. The reaction mixture was concentrated in vacuo. The residue was purified by chromatography on silica gel with petrol and increasing amounts of ethyl acetate. The product consist of a mixture of regio-isomers.
Yield: 33 mg (mixture of regioisomers 29a/28c ratio: 2:8)

(28d/29b). methyl 7-(allyloxy)-2-(2-fluorophenyl)-6-methoxy-9,10-dihydrophenanthrene-3-carboxylate/ methyl 6-(allyloxy)-2-(2-fluorophenyl)-7-methoxy-9,10-dihydrophenanthrene-3-carboxylate Allyl chloride (35 μL) was added to a solution of intermediate 29a and 28c (54 mg) and potassium carbonate (30 mg) in DMF (2 ml). The reaction mixture was heated to 60° C. for 18 hours and then allowed to cool to ambient temperature. The mixture was partitioned between ethyl acetate and water and the aqueous phase was re-extracted with ethyl acetate. The combined organics were washed with water and brine before passing through a hydrophobic frit. The solvents were removed under vacuum to give a pale brown residue that was purified by chromatography on silica gel, eluting with petrol and increasing amounts of ethyl acetate.
Yield: 58 mg (mixture of regioisomers 29b/28d ratio: 2:8)

(28e/29c). 7-(allyloxy)-2-(2-fluorophenyl)-6-methoxy-9,10-dihydrophenanthrene-3-carboxylic acid/6-(allyloxy)-2-(2-fluorophenyl)-7-methoxy-9,10-dihydrophenanthrene-3-carboxylic acid Sodium hydroxide (0.75 ml, 2M, aqueous solution) was added to a solution containing a 2:8 to mixture of intermediates 29b and 28d (58 mg) in ethanol (3 ml). The reaction mixture was heated to 40° C. for 2 hours. The reaction mixture was cooled to 0° C. and then acidified to pH 1 with a aqueous 2M HCl solution before extracting into ethyl acetate. The organic layer was washed with water and then dried by passing through a hydrophobic frit. The solvents were removed under vacuum.
Yield: 56 mg (mixture of regioisomers 29c/28e ratio: 2:8)

(28f/29d). 7-(allyloxy)-2-(2-fluorophenyl)-N—((R)-1-hydroxy-3-(1H-indol-3-yl)propan-2-yl)-6-methoxy-9,10-dihydrophenanthrene-3-carboxamide 16-(allyloxy)-2-(2-fluorophenyl)-N—((R)-1-hydroxy-3-(1H-indol-3-yl)propan-2-yl)-7-methoxy-9,10-dihydrophenanthrene-3-carboxamide 1-Ethyl-3-(3-dimethylaminopropyl)carbodiimide hydrochloride (40.1 mg) was added to a solution containing a 2:8 mixture of phenol isomers 29c and 28e (56 mg), 1-hydroxy-benzotriazole (19.8 mg) and triethylamine (58 μL) in DMF (2 ml). The mixture was stirred for 5 minutes before the addition of D-tryptophanol (33.2 mg), and stirred for a further 18 hours. Ethyl acetate was added and the solution was washed with a aqueous 0.5M HCl solution and the aqueous layer was re-extracted with ethyl acetate. The combined organics were washed with saturated aqueous sodium bicarbonate solution, water and brine before drying by passing through a hydrophobic frit. The solvents were removed under vacuum to give a pale yellow oil that was purified by preparative HPLC, eluting with water and increasing amounts of acetonitrile.

28f: Yield: 38 mg
MS (ESI) m/z: 577 (M+H)⁺.
¹H NMR δ (ppm) (CHCl₃-d): 8.17 (1H, s), 7.97 (1H, s), 7.64-7.52 (1H, m), 7.21-7.01 (5H, m), 6.88 (1H, d, J=2.30 Hz), 6.76 (1H, s), 6.20-6.05 (1H, m), 5.78 (1H, d, J=7.36 Hz), 5.48-5.30 (2H, m), 4.67-4.62 (2H, m), 4.34-4.20 (1H, m), 3.92 (3H, s), 3.46 (2H, t, J=4.42 Hz), 2.92-2.74 (6H, m), 2.44 (1H, t, J=5.50 Hz), 1.68 (1H, s).

29d: Yield: 4.5 mg
MS (ESI) m/z: 577 (M+H)⁺.
¹H NMR δ (ppm) (CHCl₃-d): 8.09-7.99 (1H, m), 7.92 (1H, s), 7.57 (1H, d, J=7.98 Hz), 7.23-7.03 (5H, m), 6.93 (1H, dd, J=9.51, 2.31 Hz), 6.77 (1H, s), 6.19-6.08 (1H, m), 5.74 (1H, d, J=7.29 Hz), 5.46 (1H, dd, J=17.25, 1.72 Hz), 5.31 (1H, dd, J=10.48, 1.53 Hz), 4.68 (2H, d, J=5.51 Hz), 4.32-4.24 (1H, m), 3.92 (3H, s), 3.54-3.47 (2H, m), 2.92-2.73 (6H, m), 2.31 (1H, t, J=5.68 Hz).

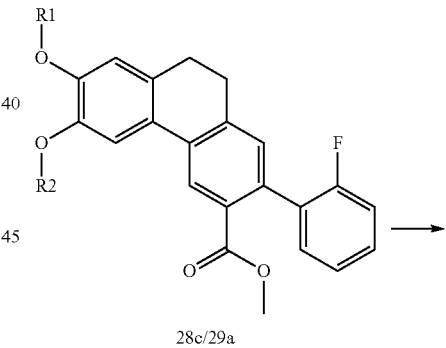

28c/29a
28c: R1 = H, R2 = Me
29a: R1 = Me, R2 = H

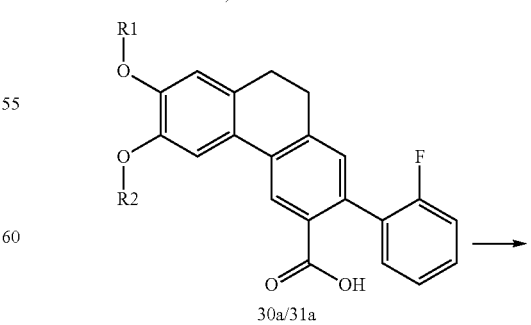

30a/31a
28e: R1 = H, R2 = Me
29c: R1 = Me, R2 = H

-continued

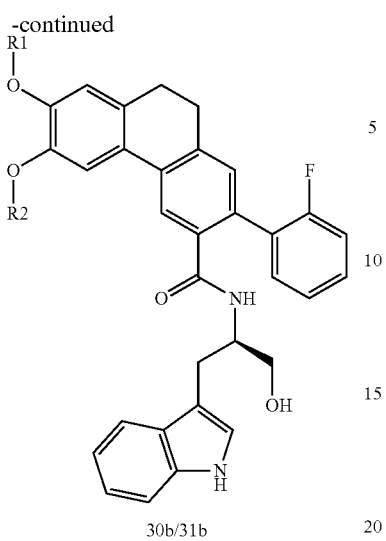

28f: R1 = H, R2 = Me
29d: R1 = Me, R2 = H

Example 30131

2-(2-fluorophenyl)-7-hydroxy-N—((R)-1-hydroxy-3-(1H-indol-3-yl)propan-2-yl)-6-methoxy-9,10-dihydrophenanthrene-3-carboxamide 12-(2-fluorophenyl)-6-hydroxy-N—((R)-1-hydroxy-3-(1H-indol-3-yl)propan-2-yl)-7-methoxy-9,10-dihydrophenanthrene-3-carboxamide (30a/31a). 2-(2-fluorophenyl)-7-hydroxy-6-methoxy-9,10-dihydrophenanthrene-3-carboxylic acid/2-(2-fluorophenyl)-6-hydroxy-7-methoxy-9,10-dihydrophenanthrene-3-carboxylic acid Sodium hydroxide (0.75 ml, 1.50 mmol, aqueous 2M solution) was added to a solution containing a 2:8 mixture of phenol isomers 28c and 29a (114 mg) in ethanol (2 ml). The mixture was heated to 50° C. for 18 hours and then cooled to 0° C. before acidifying with a aqueous 0.5M HCl solution. The aqueous phase was extracted with ethyl acetate twice and the combined organics were washed with water and brine before drying by passing through a hydrophobic frit. The solvents were removed under vacuum.

Yield: 110 mg (mixture of regioisomers 30a and 31a)

(30b/31b). 2-(2-fluorophenyl)-7-hydroxy-N—((R)-1-hydroxy-3-(1H-indol-3-yl)propan-2-yl)-6-methoxy-9,10-dihydrophenanthrene-3-carboxamide/2-(2-fluorphenyl)-6-hydroxy-N—((R)-1-hydroxy-3-(1H-indol-3-yl)propan-2-yl)-7-methoxy-9,10-dihydrophenanthrene-3-carboxamide 1-Ethyl-3-(3-dimethylaminopropyl)carbodiimide hydrochloride (87 mg) was added to a solution containing a 2:8 mixture of intermediates 30a and 31a (110 mg), 1-hydroxybenzotriazole (43 mg) and triethylamine (126 μL) in DMF (2 ml). The mixture was stirred for 5 minutes before the addition of D-tryptophanol (71.6 mg), stirring for a further 18 hours. Ethyl acetate was added and the solution was washed with a aqueous 0.5 M HCl solution. The aqueous layer was re-extracted with ethyl acetate. The combined organics were washed with saturated aqueous sodium bicarbonate solution, water and brine before drying by passing through a hydrophobic frit. The solvents were removed under vacuum to give a pale yellow oil that was purified by preparative HPLC, eluting with water and increasing amounts of acetonitrile 30b: Yield: 54 mg MS (ESI) m/z: 537 (M+H)$^+$.

$^1$H NMR δ (ppm) (CHCl$_3$-d): 8.19 (1H, s), 7.96 (1H, s), 7.60-7.52 (1H, m), 7.33-6.98 (9H, m), 6.88-6.82 (1H, m), 6.86-6.68 (1H, m), 5.9 (1H, bs), 5.80 (1H, d, J=7.40 Hz), 4.37-4.21 (1H, m), 3.87 (3H, s), 3.55-3.40 (2H, m), 2.8 (2H, m), 2.75-2.70 (4H, m).

31b: 16.4 mg

MS (ESI) m/z: 537 (M+H)$^+$.

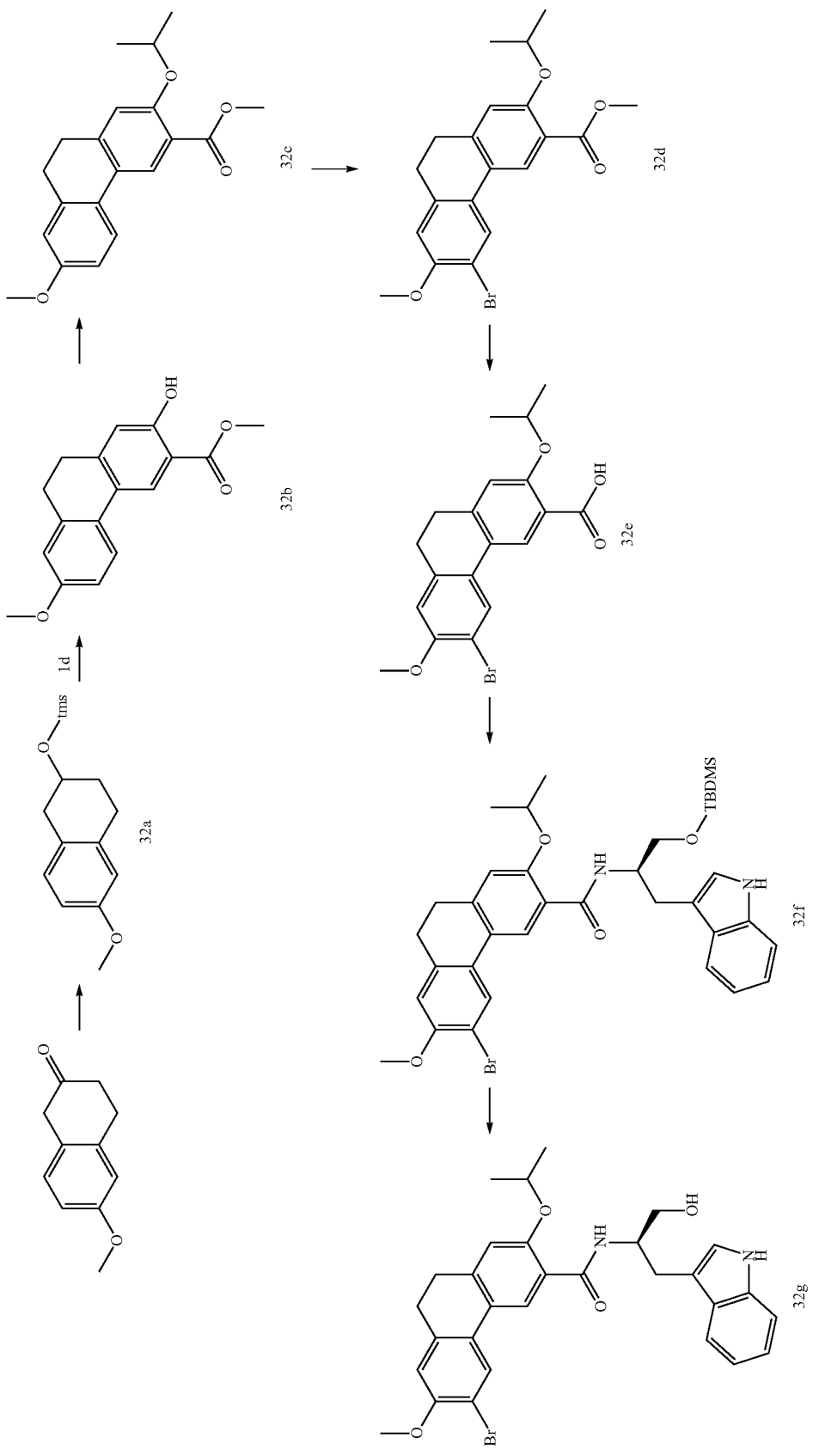

Example 32

(R)-6-bromo-N-(1-hydroxy-3-(1H-indol-3-yl)propan-2-yl)-2-isopropoxy-7-methoxy-9,10-dihydrophenanthrene-3-carboxamide

(a). (6-methoxy-1,2,3,4-tetrahydronaphthalen-2-yloxy)trimethylsilane

6-Methoxy-3,4-dihydronaphthalen-2(1H)-one (25 g) was treated with LDA (110 ml) in dry THF (500 ml) at −78° C. for 5 minutes. Then TMSCl (21.64 g) was added and after 30 minutes the cooling bath was removed. After 1 hour at room temperature the solvent was evaporated in vacuo and the residue was dissolved in heptane and filtered to eliminate the solid particulate. Finally the heptane was evaporated in vacuo.
Yield: 55 g (crude)

(b). methyl 2-hydroxy-7-methoxy-9,10-dihydrophenanthrene-3-carboxylate

Trimethylorthoformate (15.04 g) was dissolved DCM (1 L) and cooled to −78° C. TiCl$_4$ (26.9 g) was added followed by compound 1d (55 g, crude material, based on 100% conversion the amounts presents of the sylil enol ether of the tetralone is 35.2 g) in DCM (100 ml). The mixture was stirred two hours at −78° C. TiCl$_4$ (26.9 g) was added followed by compound 32a (80 g, crude material, based on 100% conversion the amounts of diene present is 51.7 g). The mixture was stirred at −78C for 40 minutes and then the cooling bath was removed and the reaction allowed to reach room temperature overnight. The mixture was poured into a saturated aqueous solution of NaHCO$_3$, filtered over a pad of celite and extracted with dichloromethane. The organic layers were collected, dried on Na$_2$SO$_4$, filtered and concentrated in vacuo. The residue was purified by chromatography on silica gel, eluting with heptane and increasing amounts of ethyl acetate.
Yield: 22.5 g
MS (ESI) m/z: 285 (M+H)$^+$.

(c). methyl 2-isopropoxy-7-methoxy-9,10-dihydrophenanthrene-3-carboxylate

Compound 32b (25.6 g) was dissolved in DMF (500 ml) and potassium carbonate (37.3 g) and 2-iodopropane (77 g) were added and the mixture was heated at 70° C. overnight. The reaction mixture was quenched by adding water and extracted 4 times with ethyl acetate. The organic layers were collected, dried over Na$_2$SO$_4$, filtered and evaporated in vacuo.
Yield: 29 g
MS (ESI) m/z: 327 (M+H)$^+$.

(d). methyl 6-bromo-2-isopropoxy-7-methoxy-9,10-dihydrophenanthrene-3-carboxylate Compound 32c (29 g) was dissolved in DCM (1 L) and treated with N-bromosuccinimide (17.4 g). The reaction turned dark-orange and was stirred overnight at room temperature. The reaction was quenched by adding a saturated aqueous solution of NaHCO$_3$, the phases were separated and the aqueous layers extracted twice with DCM. The organic layers were collected, dried over Na$_2$SO$_4$, filtered and concentrated in vacuo.
Yield: 35 g

(e). 6-bromo-2-isopropoxy-7-methoxy-9,10-dihydrophenanthrene-3-carboxylic acid Compound 32d (35 g) was dissolved in a mixture of H$_2$O/THF=1/1 (700 ml), Lithium hydroxide (34.5 g) was added and the reaction mixture was heated to 50° C. for 24 hours. The reaction was quenched by adding a aqueous 6N HCl solution and extracted three times with ethyl acetate. The organic layers were dried Na$_2$SO$_4$, filtered and concentrated in vacuo.
Yield: 24 g

(f). (R)-6-bromo-N-(1-(tert-butyldimethylsilyloxy)-3-(1H-indol-3-yl)propan-2-yl)-2-isopropoxy-7-methoxy-9,10-dihydrophenanthrene-3-carboxamide Compound 32e (22.5 g) and N-hydroxysuccinimide (7.28 g) were dissolved in THF (1 L) and N,N'-dicyclohexylcarbodiimide (13.05 g) in THF (250 ml) was added. The mixture was stirred for 2 hours before the compound 1j (17.5 g) was added. The mixture was stirred overnight and subsequently quenched with a saturated aqueous NaHCO$_3$ solution and extracted with ethyl acetate. The organic layer was washed subsequently with water and brine, dried over Na$_2$SO$_4$, filtered and concentrated in vacuo. The material was purified by chromatography on silica gel, eluting with heptane and increasing amounts of ethyl acetate.
Yield: 26 g

(g). (R)-6-bromo-N-(1-hydroxy-3-(1H-indol-3-yl)propan-2-yl)-2-isopropoxy-7-methoxy-9,10-dihydrophenanthrene-3-carboxamide Intermediate 32f (200 mg) was dissolved in THF (3 ml) before the addition of a 1.0; N solution of tetrabutylammonium fluoride in THF (300 μL) and stirred for 16 hours. The reaction mixture was partitioned between water and ethyl acetate and the organic phase was separated, passed through a hydrophobic frit and then concentrated to dryness. The crude residue was purified by chromatography on silica gel, eluting with isohexane and increasing amounts of ethyl acetate.
Yield: 117 mg
MS (ESI) m/z: 561, 563 (M+H)$^+$.

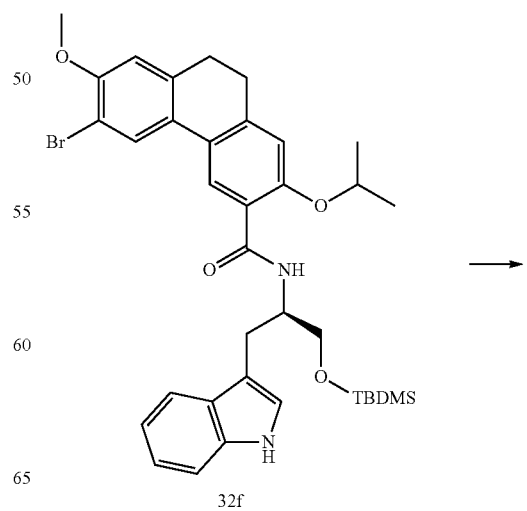

32f

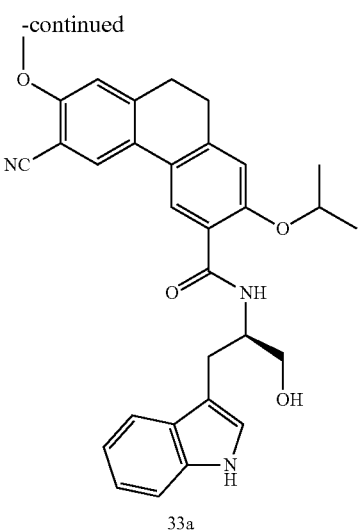

33a

Example 33

(R)-6-cyano-N-(1-hydroxy-3-(1H-indol-3-yl)propan-2-yl)-2-isopropoxy-7-methoxy-9,10-dihydrophenanthrene-3-carboxamide (a). (R)-6-cyano-N-(1-hydroxy-3-(1H-indol-3-yl)propan-2-yl)-2-isopropoxy-7-methoxy-9,10-dihydrophenanthrene-3-carboxamide To a solution of compound 32f (100 mg) were added zinc cyanide (174 mg) and Tetrakis(triphenylphosphine) palladium(0) (17.1 mg) in degassed DMF (1 ml). The reaction mixture was heated to 120° C. under a nitrogen atmosphere for 18 hrs. The reaction mixture was partitioned between ethyl acetate and water. The aqueous phase was extracted with ethyl acetate and the combined organics were washed with water and brine, dried (MgSO$_4$), filtered and concentrated in vacuo. The resulting oil was dissolved in THF (1 ml) and tetrabutylammonium fluoride (0.15 ml; 1M) was added. The reaction mixture was stirred for 18 hrs. The reaction mixture was partitioned between ethyl acetate and water. The organic layer was washed with brine, dried (MgSO$_4$) and concentrated in vacuo. The residue was purified by preparative HPLC, eluting with water and increasing amounts of acetonitrile.

Yield: 44.1 mg

MS (ESI) m/z: 510 (M+H)$^+$.

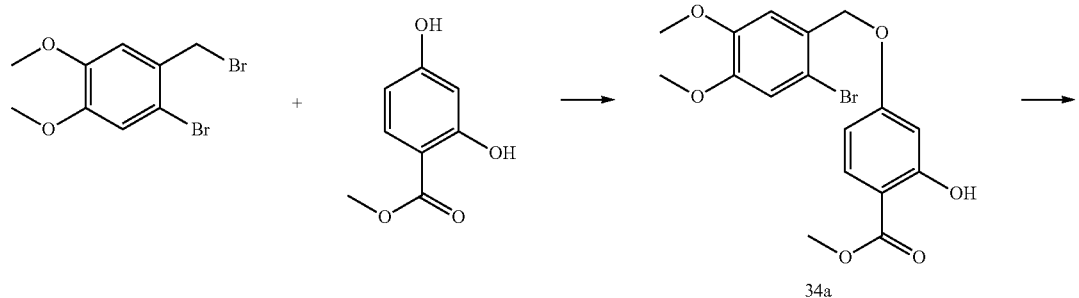

34a

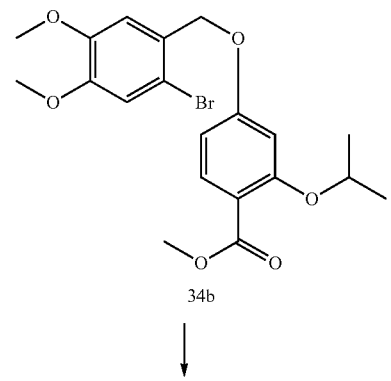

34b

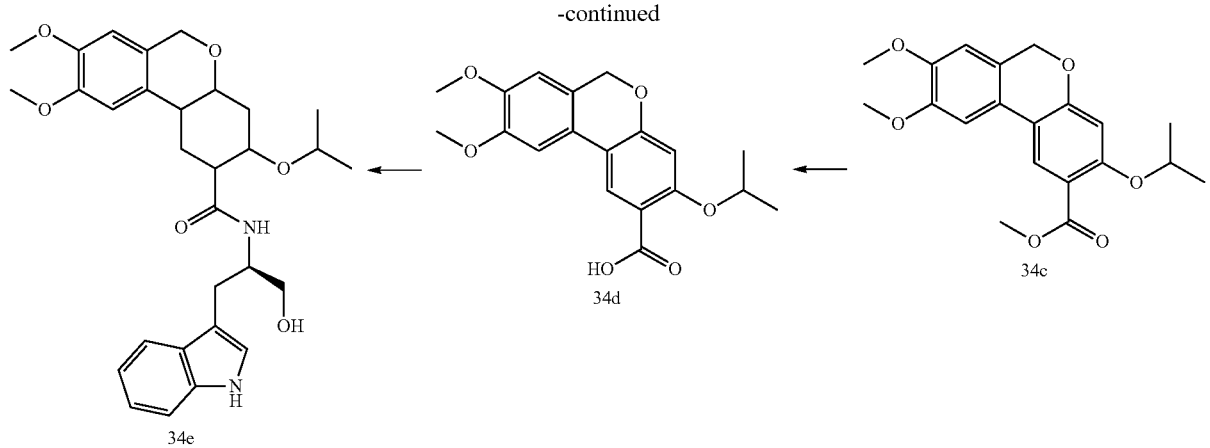

Example 34

(R)—N-(1-hydroxy-3-(1H-indol-3-yl)propan-2-yl)-3-isopropoxy-8,9-dimethoxy-6H-benzo[c]chromene-2-carboxamide (a). methyl 4-(2-bromo-4,5-dimethoxybenzyloxy)-2-hydroxybenzoate Potassium carbonate (1.12 g) was added to a solution of methyl 2,4-dihydroxybenzoate (454 mg) and 2-bromo-4,5-dimethoxybenzyl bromide (1.0 g) in dry acetone (80 ml). The reaction mixture was heated to reflux at 80° C. for 4 hours. The solvents were removed under vacuum and the residue was re-dissolved in DCM and washed with water (3×). The organic layer was passed through a hydrophobic frit and concentrated under vacuum. The crude residue was purified by chromatography on silica gel, eluting with petrol and increasing amounts of ethyl acetate.

Yield: 742 mg $^1$H NMR δ (ppm)(CHCl$_3$-d): 10.97 (1H, s), 7.76 (1H, d, J=8.8 Hz), 7.06 (1H, s), 7.00 (1H, s), 6.56-6.50 (2H, m), 5.08 (2H, s), 3.92 (3H, s), 3.89 (3H, s), 3.86 (3H, s).

(b). methyl 4-(2-bromo-4,5-dimethoxybenzyloxy)-2-isopropoxybenzoate

Potassium carbonate (166 mg) was added to a solution of intermediate 34a (238 mg) and 2-bromopropane (124 µl) in dry DMF (5 ml) before heating to 80° C. for 8 hours. Water was added and the crude product was extracted into ethyl acetate (3×). The combined organics were passed through a hydrophobic frit and concentrated under vacuum. The residue was purified by chromatography on silica gel, eluting with petrol and increasing amounts of ethyl acetate.

Yield: 230 mg $^1$H NMR δ (ppm)(CHCl$_3$-d): 7.82 (1H, d, J=8.4 Hz), 7.05 (1H, s), 7.00 (1H, s), 6.60-6.53 (2H, m), 5.10 (2H, s), 4.61-4.49 (1H, m), 3.88 (3H, s), 3.85 (6H, d, J=3.8 Hz), 1.37 (6H, d, J=6.1 Hz).

(c). methyl 3-isopropoxy-8,9-dimethoxy-6H-benzo[c]chromene-2-carboxylate

Two identical solutions of intermediate 34b (114 mg) and potassium acetate (77 mg) in dimethylacetamide (3 ml) were degassed by bubbling through a gentle stream of nitrogen for 30 minutes. Dichlorobis(triphenylphosphine)-palladium(II) (18 mg) was added to both reactions, degassing for a further 15 minutes. The reaction tubes were sealed and then heated to 130° C. for 75 minutes under microwave irradiation. Both reaction mixtures were combined and water was added. The mixture was extracted with ethyl acetate (3×). The combined organics were passed through a hydrophobic frit and concentrated under vacuum. The crude residue was purified by chromatography on silica gel, eluting with petrol and increasing amounts of ethyl acetate.

Yield: 140 mg $^1$H NMR δ (ppm)(CHCl$_3$-d): 8.12 (1H, s), 7.15 (1H, s), 6.63 (1H, s), 6.57 (1H, s), 5.11 (2H, s), 4.61-4.50 (1H, m), 3.97 (3H, s), 3.90 (6H, s), 1.40 (6H, d, J=6.0 Hz).

(d). 3-isopropoxy-8,9-dimethoxy-6H-benzo[c]chromene-2-carboxylic acid

Sodium hydroxide (46 mg) in water (0.5 ml) was added to a solution of intermediate 34c (136 mg) in ethanol (5 ml). The mixture was heated to 80° C. for 1 hour. The solvents were removed under vacuum and the residue obtained was redissolved in water and washed with diethyl ether (3×). The aqueous phase was acidified to ~pH 4 with a aqueous 4M HCl solution and the aqueous phase was extracted with DCM (3×). The combined organics were passed through a hydrophobic frit and concentrated under vacuum.

Yield: 110 mg $^1$H NMR δ (ppm)(CHCl$_3$-d): 10.80 (1H, s), 8.44 (1H, s), 7.20 (1H, s), 6.61 (2H, d, J=3.6 Hz), 5.15 (2H, s), 4.88-4.74 (1H, m), 3.98 (3H, s), 3.90 (3H, s), 1.51 (6H, d, J=6.1 Hz).

(e). (R)—N-(1-hydroxy-3-(1H-indol-3-yl)propan-2-yl)-3-isopropoxy-8,9-dimethoxy-6H-benzo[c]chromene-2-carboxamide 1-Ethyl-3-(3-dimethylaminopropyl)carbodiimide hydrochloride (92 mg) was added to a solution of intermediate 34d (110 mg), diisopropylethylamine (167 µl), 1-hydroxybenzotriazole (65 mg) and D-tryptophanol (73 mg) in dry DMF (2 ml). The mixture was stirred at room temperature for 60 hours. Water was added and the product was extracted into ethyl acetate (3×). The combined organics were passed through a hydrophobic frit and concentrated under vacuum. The crude residue was purified by chromatography on silica gel, eluting with DCM containing increasing amounts of methanol.

Yield: 58 mg

MS (ESI) m/z: 517 (M+H)+.

$^1$H NMR δ (ppm) (DMSO-d$_6$): 10.84 (1H, s), 8.42 (1H, d, J=8.0 Hz), 8.38 (1H, s), 7.77 (1H, d, J=7.9 Hz), 7.37 (1H, d, J=8.1 Hz), 7.27 (1H, s), 7.18 (1H, d, J=2.3 Hz), 7.10 (1H, td, J=7.6, 1.1 Hz), 7.01 (1H, td, J=7.4, 1.0 Hz), 6.94 (1H, s), 6.78 (1H, s), 5.15 (2H, s), 4.98 (1H, t, J=5.1 Hz), 4.83-4.79 (1H, m), 4.31-4.27 (1H, m), 3.91 (3H, s), 3.82 (3H, s), 3.55-3.44 (2H, m), 3.01 (2H, d, J=6.7 Hz), 1.30 (6H, dd, J=7.5, 6.0 Hz).

Example 35

(R)—N-(1-hydroxy-3-(1H-indol-3-yl)propan-2-yl)-3-isopropoxy-8,9-(1',3'-dioxolo)-6H-benzo[c]chromene-2-carboxamide Compound 35 was prepared in an analogous fashion as described for example 34, starting from 5-bromo-6-(bromomethyl)benzo[d][1,3]dioxole MS (ESI) m/z: 501 (M+H)+.

$^1$H NMR δ (ppm) (DMSO-d$_6$): 10.83 (1H, s), 8.37 (1H, d, J=8.0 Hz), 8.28 (1H, s), 7.74 (1H, d, J=7.9 Hz), 7.34 (1H, d, J=8.1 Hz), 7.30 (1H, s), 7.15 (1H, d, J=2.3 Hz), 7.06 (1H, dd, J=7.7, 1.1 Hz), 6.98 (1H, t, J=7.4 Hz), 6.89 (1H, s), 6.76 (1H, s), 6.06 (2H, s), 5.08 (2H, s), 4.96 (1H, t, J=5.1 Hz), 4.81-4.74 (1H, m), 4.26 (1H, s), 3.54-3.39 (2H, m), 2.98 (2H, d, J=6.7 Hz), 1.25 (6H, t, J=6.4 Hz).

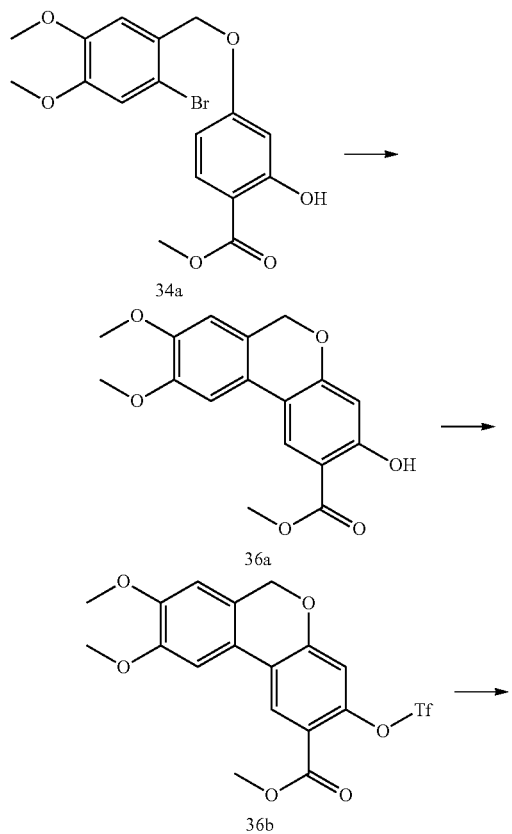

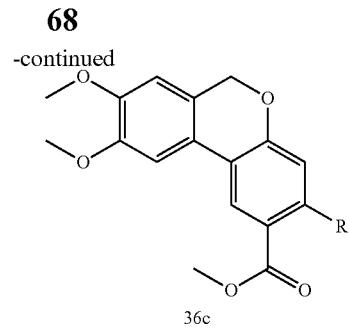

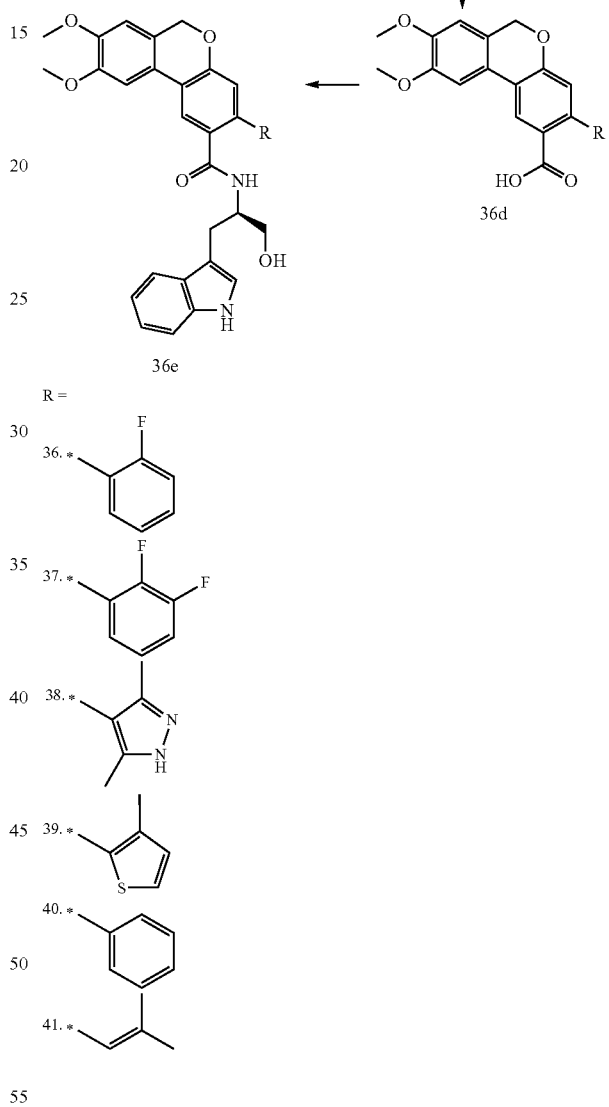

Example 36

3-(2-fluorophenyl)-N—((R)-1-hydroxy-3-(1H-indol-3-yl)propan-2-yl)-8,9-dimethoxy-6H-benzo[c]chromene-2-carboxamide (a). methyl 3-hydroxy-8,9-dimethoxy-6H-benzo[c]chromene-2-carboxylate Dichlorobis(triphenylphosphine)-palladium(II) (88 mg) was added to a thoroughly degassed solution of intermediate 34a (500 mg) and potassium acetate (368 mg) in dimethylacetamide (18 ml). The reaction mixture was degassed for a further 15 minutes then sealed and heated at 130° C. for 40 minutes by microwave irradiation. LC-MS indicated that the reaction was incomplete, hence a further aliquot of dichlorobis(triphenylphosphine)-palladium(II) (44 mg) was added and the mixture degassed with nitrogen for 15 minutes before sealing and heating to 130° C. for 40 minutes by microwave irradiation. LC-MS indicated improved conversion to the desired product, hence water was added and the aqueous phase was extracted with ethyl acetate (3×). The combined organics were washed with water (3×) and then passed through a hydrophobic frit and concentrated to dryness under vacuum. The residue obtained was purified by chromatography on silica gel, eluting with petrol and increasing amounts of ethyl acetate.

Yield: 48 mg $^1$H NMR δ (ppm)(CHCl$_3$-d): 10.90 (1H, s), 8.06 (1H, s), 7.13 (1H, s), 6.63 (1H, s), 6.55 (1H, s), 5.11 (2H, s), 3.99 (3H, s), 3.98 (3H, s), 3.89 (3H, s).

(b). methyl 8,9-dimethoxy-3-(trifluoromethylsulfonyloxy)-6H-benzo[c]chromene-2-carboxylate Trifluoromethanesulfonic anhydride (33 µl) was added to a 0° C. solution of intermediate 36a (47 mg) and triethylamine (42 µl) in DCM (1 ml). The mixture was allowed to warm to room temperature over 2 hours. Water was added and the aqueous phase was extracted into DCM (3×). The combined organics were passed through a hydrophobic frit and concentrated to dryness under vacuum.

Yield: 57 mg $^1$H NMR δ (ppm)(CHCl$_3$-d): 8.32 (1H, s), 7.19 (1H, s), 6.85 (1H, s), 6.64 (1H, s), 5.20 (2H, s), 4.00-3.98 (6H, m), 3.92 (3H, s).

(c). methyl 3-(2-fluorophenyl)-8,9-dimethoxy-6H-benzo[c]chromene-2-carboxylate

Palladium tetrakis(triphenylphosphine) (15 mg) was added to a degassed solution of intermediate 36b (56 mg), 2-fluorobenzeneboronic acid (28 mg) and potassium carbonate (31 mg) in a 10:1 mixture of DME:water (2 ml). The reaction mixture was degassed for a further 15 minutes before sealing and heating to 130° C. for 1 hour by microwave irradiation. Water was added and the mixture was extracted with ethyl acetate (3×). The combined organics were passed through a hydrophobic frit and concentrated to dryness under vacuum. The crude residue was purified by chromatography, eluting with petrol containing increasing amounts of ethyl acetate.

Yield: 38 mg

MS (ESI) m/z: 395 (M+H)$^+$.

$^1$H NMR δ (ppm)(CHCl$_3$-d): 8.28 (1H, s), 7.37-7.28 (2H, m), 7.25 (1H, s), 7.21 (1H, t, J=7.5 Hz), 7.09 (1H, t, J=9.2 Hz), 6.92 (1H, s), 6.66 (1H, s), 5.17 (2H, s), 4.00 (3H, s), 3.93 (3H, s), 3.70 (3H, s).

(d). 3-(2-fluorophenyl)-8,9-dimethoxy-6H-benzo[c]chromene-2-carboxylic acid

Sodium hydroxide (11.4 mg) in water (0.2 ml) was added to a solution of intermediate 36c (38 mg) in ethanol (2 ml) and the reaction mixture was heated to 80° C. for 3 hours. The solvents were removed under vacuum. The residue was redissolved in water and washed with diethyl ether (2×). The aqueous phase was acidified to ~pH 3 with a aqueous 4M HCl solution and extracted with ethyl acetate (3×). The combined organics were passed through a hydrophobic frit and concentrated to dryness under vacuum.

Yield: 35 mg $^1$H NMR δ (ppm) (CH$_3$OH-d$_4$): 7.05 (1H, s), 6.10-6.00 (3H, m), 5.92 (1H, td, J=7.5, 1.0 Hz), 5.80 (1H, t, J=4.7 Hz), 5.57 (2H, d, J=8.1 Hz), (e). 3-(2-fluorophenyl)-N—((R)-1-hydroxy-3-(1H-indol-3-yl)propan-2-yl)-8,9-dimethoxy-6H-benzo[c]chromene-2-carboxamide 1-Ethyl-3-(3-dimethylaminopropyl)carbodiimide hydrochloride (26 mg), was added to a solution of intermediate 36d (34 mg), diisopropylethylamine (47 µl), 1-hydroxybenzotriazole (18 mg) and D-tryptophanol (21 mg) in dry DMF (1 ml). The mixture was stirred at room temperature for 18 hours. The crude reaction mixture was filtered and then purified by preparative HPLC, eluting with water and increasing amounts of acetonitrile.

Yield: 43 mg

MS (ESI) m/z: 553 (M+H)$^+$.

$^1$H NMR δ (ppm) (DMSO-d$_6$): 10.82 (1H, s), 7.94-7.87 (2H, m), 7.63 (1H, d, J=7.9 Hz), 7.42 (1H, s), 7.40-7.27 (3H, m), 7.23-7.05 (4H, m), 7.02-6.95 (2H, m), 6.91 (1H, s), 5.17 (2H, s), 4.72 (1H, t, J=5.7 Hz), 4.07-4.00 (1H, m), 3.93 (3H, s), 3.85 (3H, s), 3.49-3.42 (1H, m), 3.36-3.28 (1H, m), 2.94 (1H, dd, J=14.5, 6.1 Hz), 2.82 (1H, dd, J=14.4, 7.4 Hz).

Example 37

3-(2,3-difluorophenyl)-N—((R)-1-hydroxy-3-(1H-indol-3-yl)propan-2-yl)-8,9-dimethoxy-6H-benzo[c]chromene-2-carboxamide Compound 37 was prepared in an analogous fashion as described for example 36.

MS (ESI) m/z: 571 (M+H)$^+$.

Example 38

3-(3,5-dimethyl-1H-pyrazol-4-yl)-N—((R)-1-hydroxy-3-(1H-indol-3-yl)propan-2-yl)-8,9-dimethoxy-6H-benzo[c]chromene-2-carboxamide Compound 38 was prepared in an analogous fashion as described for example 36.

MS (ESI) m/z: 553 (M+H)$^+$.

Example 39

N—((R)-1-hydroxy-3-(1H-indol-3-yl)propan-2-yl)-8,9-dimethoxy-3-(3-methylthiophen-2-yl)-6H-benzo[c]chromene-2-carboxamide Compound 39 was prepared in an analogous fashion as described for example 36.

MS (ESI) m/z: 555 (M+H)$^+$.

Example 40

(R)—N-(1-hydroxy-3-(1H-indol-3-yl)propan-2-yl)-8,9-dimethoxy-3-phenyl-6H-benzo[c]chromene-2-carboxamide Compound 40 was prepared in an analogous fashion as described for example 36.

MS (ESI) m/z: 535 (M+H)$^+$.

Example 41

(R)—N-(1-hydroxy-3-(1H-indol-3-yl)propan-2-yl)-8,9-dimethoxy-3(2-methylprop-1-enyl)-6H-benzo[c]chromene-2-carboxamide Compound 41 was prepared in an analogous fashion as described for example 36.

MS (ESI) m/z: 513 (M+H)$^+$.

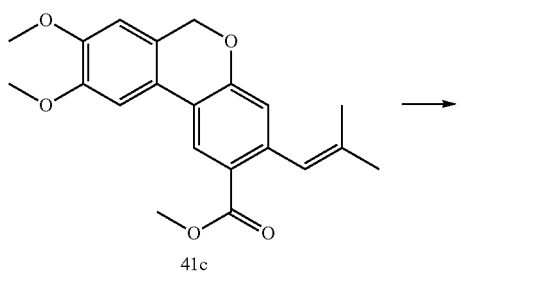

41c

Example 42

(R)—N-(1-hydroxy-3-(1H-indol-3-yl)propan-2-yl)-3-isobutyl-8,9-dimethoxy-6H-benzo[c]chromene-2-carboxamide (a). methyl 3-isobutyl-8,9-dimethoxy-6H-benzo[c]chromene-2-carboxylate 10% Pd/C (40 mg) was added to a degassed solution of compound 41c (42 mg) in methanol (5 ml) under a nitrogen atmosphere. The reaction mixture was subjected to a hydrogen atmosphere for 18 hrs. Na$_2$SO$_4$ and ethyl acetate were added and the reaction mixture was filtered through celite and concentrated in vacuo.

Yield: 40 mg

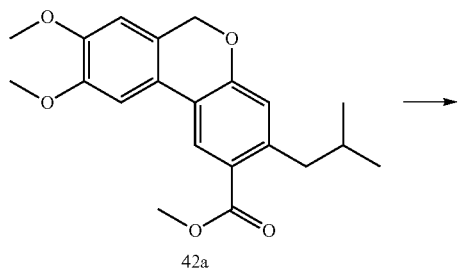

42a (b). 3-isobutyl-8,9-dimethoxy-6H-benzo[c]chromene-2-carboxylic acid

A aqueous solution of 2N sodium hydroxide solution (0.75 ml) was added to a solution of intermediate 42a (40 mg) in ethanol (4 ml) and the mixture was heated to 80° C. for 3 hours. The solvents were removed under vacuum. The residue was re-dissolved in water and washed with diethyl ether (2×). The aqueous phase was acidified to ~pH 3 with a aqueous 4M HCl solution and extracted with ethyl acetate (3×). The combined organics were passed through a hydrophobic frit and concentrated to dryness under vacuum.

Yield: 33 mg

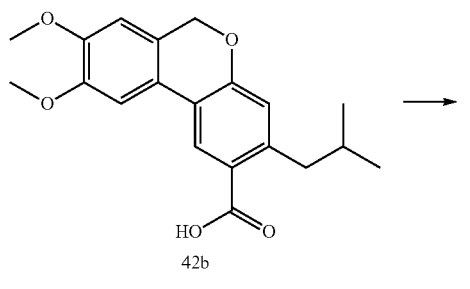

42b (c). (R)—N-(1-hydroxy-3-(1H-indol-3-yl)propan-2-yl)-3-isobutyl-8,9-dimethoxy-6H-benzo[c]chromene-2-carboxamide 1-Ethyl-3-(3-dimethylaminopropyl)carbodiimide hydrochloride (28 mg), was added to a solution of intermediate 42b (33 mg), triethylamine (40 µl), 1-hydroxybenzotriazole (13 mg) and D-tryptophanol (22 mg) in dry DMF (1 ml). The mixture was stirred at room temperature for 18 hours. Ethyl acetate was added and the solution was washed with a aqueous 0.5 M HCl solution. The aqueous layer was re-extracted with ethyl acetate. The combined organics were washed with saturated aqueous sodium bicarbonate solution, water and brine before drying by passing through a hydrophobic frit. The solvents were removed under vacuum. The residue was purified by chromatography on silica gel, eluting with DCM and increasing amounts of methanol.

Yield: 43 mg

MS (ESI) m/z: 515 (M+H)$^+$.

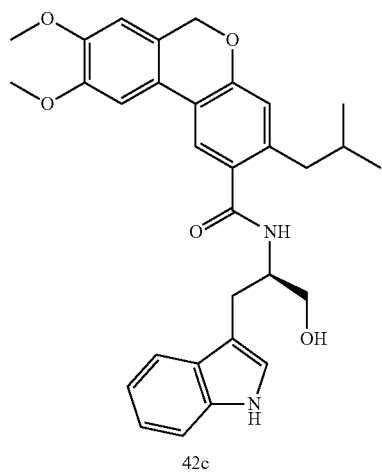

42c

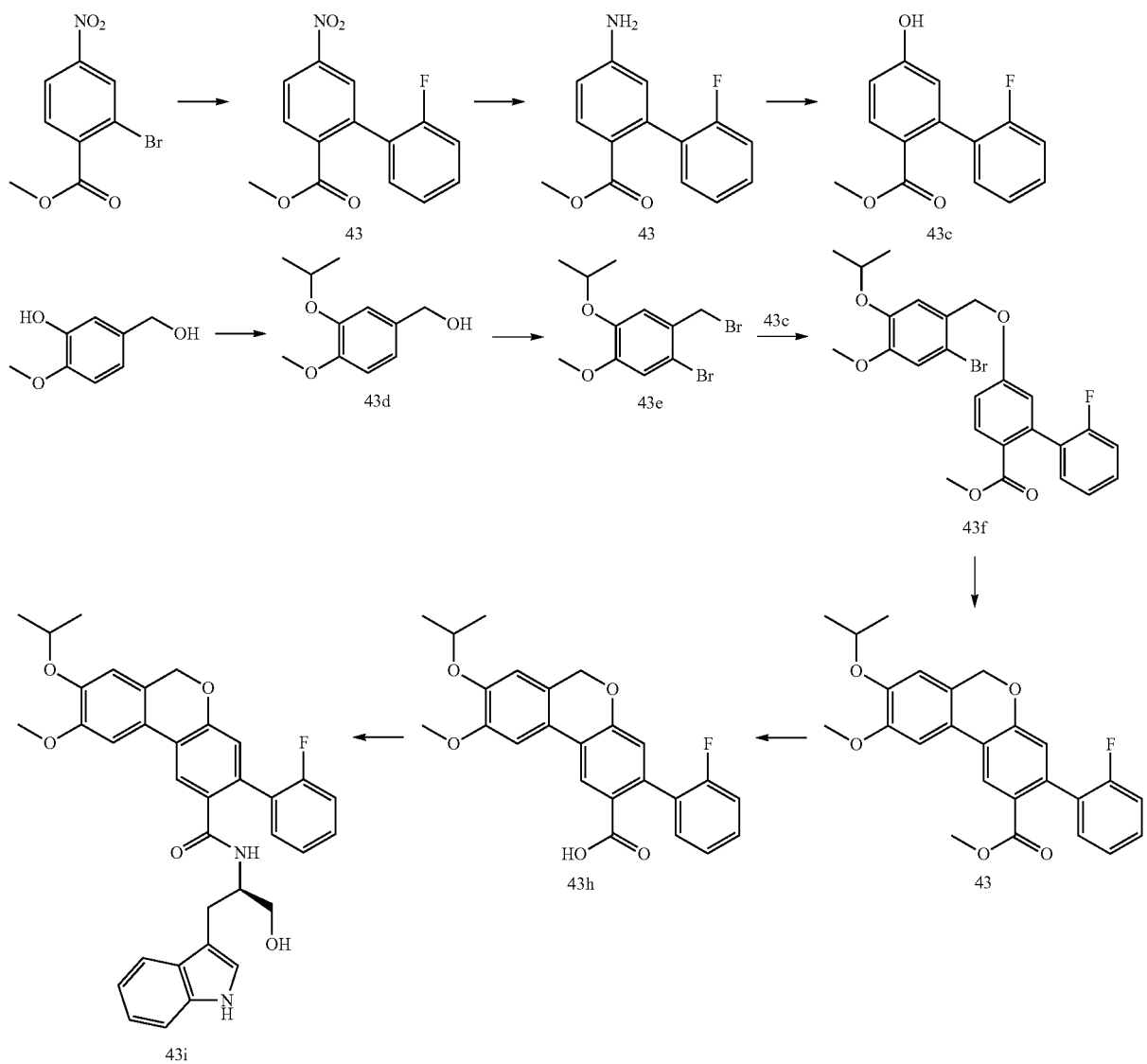

Example 43

3-(2-fluorophenyl)-N—((R)-1-hydroxy-3-(1H-indol-3-yl)propan-2-yl)-8-isopropoxy-9-methoxy-6H-benzo[c]chromene-2-carboxamide (a). methyl 2'-fluoro-5-nitrobiphenyl-2-carboxylate A solution of methyl 2-bromo-4-nitrobenzoate (5.20 g), 2-fluorophenylboronic acid (3.92 g) and potassium carbonate (4.98 g) in a 10:1 mixture of DME:water (120 ml) was degassed by gently bubbling though nitrogen for 30 minutes. Tetrakis(triphenylphosphine) palladium(0) (2.32 g) was then added and the mixture was degassed for a further 10 minutes before being sealed under nitrogen. The reaction mixture was heated to 100° C. for 14 hours. The solvents were removed under vacuum. The residue obtained was redissolved in DCM and washed with water (2×). The organic phase was passed through a hydrophobic frit and then concentrated to dryness under vacuum. The crude residue was purified by chromatography on silica gel, eluting with petrol containing increasing amounts of ethyl acetate.

Yield: 4.85 g $^1$H NMR δ (ppm)(DMSO-d$_6$): 8.41 (1H, dd, J=8.6, 2.4 Hz), 8.23 (1H, d, J=2.4 Hz), 8.16 (1H, d, J=8.6 Hz), 7.57-7.50 (2H, m), 7.41-7.31 (2H, m), 3.72 (3H, s).

(b). methyl 5-amino-2'-fluorobiphenyl-2-carboxylate

Iron powder (5.72 g) in glacial acetic acid (70 ml) was stirred with high agitation via an overhead stirrer at 85° C. for 45 minutes. A solution of intermediate 43a (5.64 g) in glacial acetic acid (70 ml) was then added portion-wise over 10 minutes and the mixture was heated for a further 2 hours at 85° C. The reaction mixture was filtered through a pad of celite (wet with hot acetic acid) which was washed through with further hot acetic acid followed by ethyl acetate. The solvents were removed under vacuum and the residue was basified at 0° C. with a saturated aqueous sodium bicarbonate solution. The aqueous phase was extracted with ethyl acetate (3×) and the combined organics were passed through a hydrophobic frit before concentrating to dryness under vacuum.

Yield: 5.0 g $^1$H NMR δ (ppm)(DMSO-d$_6$): 7.72 (1H, d, J=8.6 Hz), 7.41-7.35 (1H, m), 7.24 (2H, td, J=3.6, 1.6 Hz), 7.18 (1H, dd, J=10.4, 8.2 Hz), 6.63 (1H, dd, J=8.6, 2.3 Hz), 6.45 (1H, d, J=2.3 Hz), 6.02 (2H, s), 3.54 (3H, s).

(c). methyl 2'-fluoro-5-hydroxybiphenyl-2-carboxylate

A mixture of intermediate 43b (5.0 g) in aqueous 5% sulfuric acid (100 ml) was cooled in an ice-bath. A solution of sodium nitrite (1.54 g) in water (16 ml) was then added dropwise and the resulting mixture was stirred at 0° C. for 1 hour and then heated to 60° C. for 18 hours. The mixture was cooled and diluted with ethyl acetate. The organic phase was separated, passed through a hydrophobic frit and then concentrated to dryness under vacuum. The crude residue was purified by chromatography on silica gel, eluting with petrol containing increasing amounts of ethyl acetate.

Yield: 3.64 g $^1$H NMR δ (ppm) (DMSO-d$_6$): 10.45 (1H, s), 7.84 (1H, d, J=8.6 Hz), 7.45-7.38 (1H, m), 7.37-7.20 (3H, m), 6.92 (1H, dd, J=8.6, 2.5 Hz), 6.72 (1H, d, J=2.5 Hz), 3.59 (3H, s).

(d). (3-isopropoxy-4-methoxyphenyl)methanol

Potassium carbonate (13.5 g) was added to a solution of 3-hydroxy-4-methoxybenzyl alcohol (10.0 g) and 2-bromopropane (9.15 ml) in dry DMF (100 ml) and the mixture was heated to reflux for 72 hours. The solvent was removed under vacuum. The residue obtained was partitioned between water and ethyl acetate. The aqueous phase was re-extracted with ethyl acetate (2×) and the combined organics were passed through a hydrophobic frit. The solvents were removed under vacuum.

Yield: 12.22 g $^1$H NMR δ (ppm)(DMSO-d$_6$): 6.96-6.88 (2H, m), 6.89-6.83 (1H, m), 5.08-5.01 (1H, m), 4.57-4.47 (1H, m), 4.43 (2H, d, J=4.4 Hz), 3.75 (3H, s), 1.28 (6H, d, J=6.05 Hz).

(e). 1-bromo-2-(bromomethyl)-4-isopropoxy-5-methoxybenzene

Bromine (4.78 ml) was added dropwise over 30 minutes to a solution of intermediate 43d (12.2 g) in acetic acid (40 ml) and the reaction mixture was then stirred for a further 16 hours. The solvent was removed under vacuum. The condensed bromine residue was destroyed with 20% aqueous sodium hydroxide solution. The crude residue was basified with saturated aqueous sodium bicarbonate solution and then extracted with DCM (3×). The combined organics were passed through a hydrophobic frit and then concentrated to dryness under vacuum.

Yield: 20.5 g $^1$H NMR δ (ppm) (DMSO-d$_6$): 7.29 (1H, s), 7.20 (1H, s), 4.72 (2H, s), 4.61-4.53 (1H, m), 3.81 (3H, s), 1.28 (6H, d, J=6.1 Hz).

(f). methyl 5-(2-bromo-5-isopropoxy-4-methoxybenzyloxy)-2'-fluorobiphenyl-2-carboxylate Potassium carbonate (6.10 g) was added to a solution of intermediate 43c (3.62 g) and intermediate 43e (5.71 g) in dry acetone (250 ml) and the mixture was then heated to reflux for 4 hours. The solvent was removed under vacuum. The residue obtained was redissolved in DCM and washed with water (3×). The organic phase was passed through a hydrophobic frit and concentrated to dryness under vacuum. The crude residue was purified by chromatography on silica gel, with petrol containing increasing amounts of ethyl acetate.

Yield: 6.0 g.

$^1$H NMR δ (ppm) (DMSO-d$_6$): 7.94 (1H, d, J=8.7 Hz), 7.47-7.41 (1H, m), 7.40 (1H, td, J=3.9, 1.9 Hz), 7.34-7.18 (5H, m), 7.03 (1H, d, J=2.6 Hz), 5.18 (2H, s), 4.58-4.51 (1H, m), 3.82 (3H, s), 3.62 (3H, s), 1.25 (6H, d, J=6.0 Hz).

(g). methyl 3-(2-fluorophenyl)-8-isopropoxy-9-methoxy-6H-benzo[c]chromene-2-carboxylate Two separate solutions of intermediate 43f (2.77 g) and potassium acetate (1.62 g) in dimethylacetamide (100 ml) were degassed by gently bubbling through nitrogen gas for 30 minutes. Dichlorobis(triphenylphosphine)-palladium(II) (193 mg) was added to each reaction, degassing with nitrogen for a further 15 minutes. The reaction mixtures were sealed and heated to 100° C. for 40 hours. The reaction mixtures were combined and the solvent was removed under vacuum. Water was added and the aqueous phase was extracted with ethyl acetate (3×). The combined organics were passed through a hydrophobic frit and then concentrated to dryness under vacuum. The crude residue purified by chromatography on silica gel, eluting with petrol containing increasing amounts of diethyl ether.

Yield: 2.83 g.

$^1$H NMR δ (ppm)(CHCl$_3$-d): 8.28 (1H, s), 7.38-7.27 (2H, m), 7.27 (1H, s), 7.20 (1H, td, J=7.4, 1.2 Hz), 7.09 (1H, t, J=9.2 Hz), 6.92 (1H, s), 6.69 (1H, s), 5.15 (2H, s), 4.61-4.52 (1H, m), 3.97 (3H, s), 3.70 (3H, s), 1.41 (6H, d, J=6.1 Hz).

(h). 3-(2-fluorophenyl)-8-isopropoxy-9-methoxy-6H-benzo[c]chromene-2-carboxylic acid Sodium hydroxide (26 mg) in water (0.2 ml) was added to a solution of intermediate 43 g (93 mg) in ethanol (2 ml) and the mixture was heated to 70° C. for 3 hours. HPLC analysis indicated the absence of starting material, hence the solvents were removed under vacuum. The crude residue was redissolved in water, washed with diethyl ether. The aqueous phase was acidified to pH 3 with a aqueous 2M HCl solution and then extracted with ethyl acetate (3×). The combined organics were passed through a hydrophobic frit and concentrated to dryness under vacuum.

Yield: 85 mg.

$^1$H NMR δ (ppm)(CHCl$_3$-d): 11.00 (1H, s), 8.37 (1H, s), 7.38-7.28 (2H, m), 7.26-7.25 (1H, m), 7.19 (1H, t, J=7.5 Hz), 7.07 (1H, t, J=9.0 Hz), 6.90 (1H, s), 6.68 (1H, s), 5.15 (2H, s), 4.63-4.51 (1H, m), 3.97 (3H, s), 1.40 (6H, d, J=6.1 Hz).

(i). 3-(2-fluorophenyl)-N—((R)-1-hydroxy-3-(1H-indol-3-yl)propan-2-yl)-8-isopropoxy-9-methoxy-6H-benzo[c]chromene-2-carboxamide A solution of intermediate 43h (82 mg), diisopropylethylamine (105 µl), 1-ethyl-3-(3-dimethylaminopropyl)carbodiimide hydrochloride (58 mg), 1-hydroxybenzotriazole (41 mg) and D-tryptophanol (46 mg) in DMF (1 ml) was stirred at room temperature for 60 hours. Water and ethyl acetate were added. The aqueous phase was re-extracted with ethyl acetate (2×) before the combined organics were passed through a hydrophobic frit. The solvents were removed under vacuum and the crude residue was then purified preparative HPLC, eluting with water and increasing amounts of acetonitrile.

Yield: 70 mg

MS (ESI) m/z: 581 (M+H)$^+$.

¹H NMR δ (ppm) (CHCl₃-d): 8.04 (1H, s), 8.00 (1H, s), 7.57 (1H, d, J=7.9 Hz), 7.35 (1H, d, J=8.1 Hz), 7.32-7.27 (2H, m), 7.24 (1H, s), 7.20-7.13 (2H, m), 7.11 (1H, t, J=3.8 Hz), 7.05 (1H, t, J=9.0 Hz), 6.92-6.89 (2H, m), 6.68 (1H, s), 5.67 (1H, d, J=7.3 Hz), 5.12 (2H, s), 4.60-4.53 (1H, m), 4.31-4.24 (1H, m), 3.93 (3H, s), 3.51-3.44 (2H, m), 2.76 (2H, d, J=7.0 Hz), 2.30 (1H, t, J=5.7 Hz), 1.40 (6H, d, J=6.1 Hz).

Example 44

3-(2-fluorophenyl)-8-hydroxy-N—((R)-1-hydroxy-3-(1H-indol-3-yl)propan-2-yl)-9-methoxy-6H-benzo[c]chromene-2-carboxamide (a). methyl 3-(2-fluorophenyl)-8-hydroxy-9-methoxy-6H-benzo[c]chromene-2-carboxylate A solution of intermediate 43g (2.0 g) in DCM (60 ml) was slowly added to a 0° C. stirred suspension of anhydrous aluminum chloride (692 mg) in DCM (40 ml) and stirred for 1 hour. LC-MS analysis indicated the reaction to be incomplete, hence a further aliquot of anhydrous aluminum chloride (692 mg) was added and the mixture was stirred for a further 1 hour at 0° C. LC-MS analysis indicated the reaction to be complete, hence the mixture was quenched by the slow addition of ice water with vigorous stirring. The organic phase passed through a hydrophobic frit and concentrated to dryness under vacuum.

Yield: 1.79 g

¹H NMR δ (ppm)(CHCl₃-d): 8.26 (1H, s), 7.34-7.28 (2H, m), 7.25 (1H, s), 7.20 (1H, t, J=7.4 Hz), 7.09 (1H, t, J=9.2 Hz), 6.92 (1H, s), 6.73 (1H, s), 5.76 (1H, s), 5.13 (2H, s), 4.02 (3H, s), 3.69 (3H, s).

(b). 3-(2-fluorophenyl)-8-hydroxy-9-methoxy-6H-benzo[c]chromene-2-carboxylic acid Sodium hydroxide (46 mg) in water (0.2 ml) was added to a solution of intermediate 44a (145 mg) in ethanol (2 ml) and the mixture was then heated to 70° C. for 3 hours. The solvents were removed under vacuum. The residue obtained was redissolved in water and washed with diethyl ether (5 ml). The aqueous phase was acidified to ~pH 3 with a aqueous 2 M HCl solution and extracted with ethyl acetate (3×). The combined organics were passed through a hydrophobic frit and then concentrated to dryness under vacuum.

Yield: 135 mg

MS (ESI) m/z: 567 (M+H)⁺.

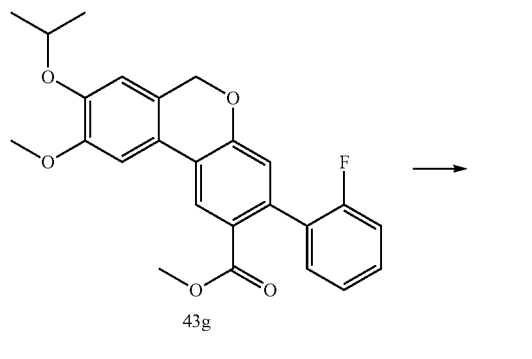

43g

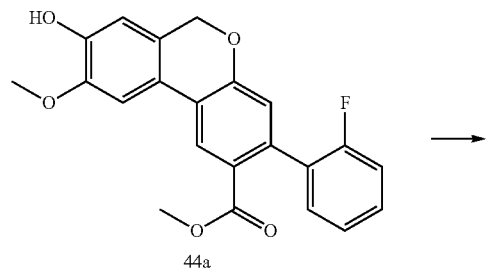

44a

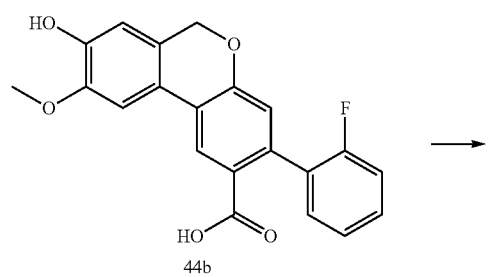

44b (c). 3-(2-fluorophenyl)-8-hydroxy-N—((R)-1-hydroxy-3-(1H-indol-3-yl)propan-2-yl)-9-methoxy-6H-benzo[c]chromene-2-carboxamide A solution of intermediate 44b (132 mg), diisopropylethylamine (188 µl), 1-ethyl-3-(3-dimethylaminopropyl)carbodiimide hydrochloride (104 mg), 1-hydroxybenzotriazole (73 mg) and D-tryptophanol (82 mg) in DMF (1 ml) was stirred at room temperature for 60 hours. Water was added and the mixture was extracted with ethyl acetate (3×). The combined organics were passed through a hydrophobic frit and then concentrated to dryness under vacuum. The crude residue was purified by preparative HPLC, eluting with water and increasing amounts of acetonitrile Yield: 52 mg MS (ESI) m/z: 539 (M+H)⁺.

¹H NMR δ (ppm) (DMSO-d₆): 10.82 (1H, s), 9.46 (1H, s), 7.90 (1H, d, J=8.1 Hz), 7.86 (1H, s), 7.63 (1H, d, J=7.9 Hz), 7.41-7.27 (4H, m), 7.22-7.05 (4H, m), 6.99 (1H, t, J=7.5 Hz), 6.88 (1H, s), 6.76 (1H, s), 5.08 (2H, s), 4.72 (1H, t, J=5.72 Hz), 4.07-4.00 (1H, m), 3.94 (3H, s), 3.50-3.43 (1H, m), 3.35 (1H, m), 2.93 (2H, ddd, J=8.6, 6.1, 4.9 Hz).

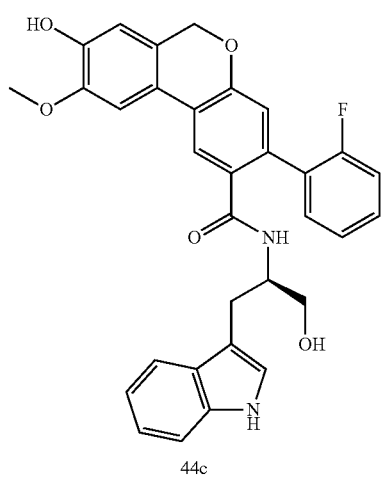

44c

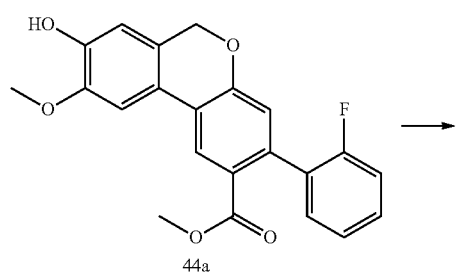

44a

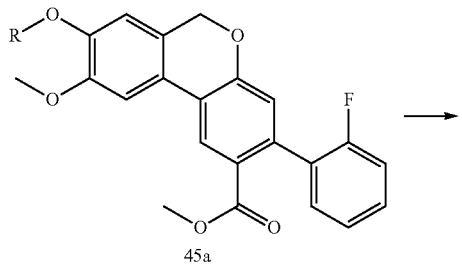

45a

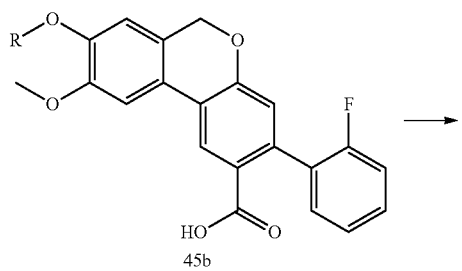

45b

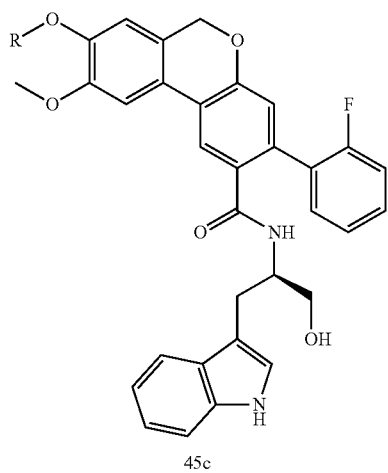

45c

R =

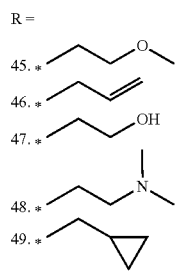

45. *
46. *
47. *
48. *
49. *

Example 45

3-(2-fluorophenyl)-N—((R)-1-hydroxy-3-(1H-indol-3-yl)propan-2-yl)-9-methoxy-8-(2-methoxyethoxy)-6H-benzo[c]chromene-2-carboxamide (a). methyl 3-(2-fluorophenyl)-9-methoxy-8-(2-methoxyethoxy)-6H-benzo[c]chromene-2-carboxylate 2-Bromoethyl methyl ether (37 µl) was added to a solution of intermediate 44a (100 mg) and potassium carbonate (72 mg) in DMF (2 ml) and the mixture was then heated to 60° C. for 16 hours. Water was added and the mixture was extracted with ethyl acetate (3×). The combined organics were passed through a hydrophobic frit and then concentrated to dryness under vacuum.
Yield: 114 mg
MS (ESI) m/z: 439 (M+H)+.

(b). 3-(2-fluorophenyl)-9-methoxy-8-(2-methoxyethoxy)-6H-benzo[c]chromene-2-carboxylic acid Sodium hydroxide (31.2 mg) in water (0.2 ml) was added to a solution of intermediate 45a (114 mg) in ethanol (1.8 ml) and the mixture was then heated to 60° C. for 3 hours. The solvents were removed under vacuum. The residue obtained was redissolved in water and washed with diethyl ether (2 ml). The aqueous phase was acidified to pH 3 with a aqueous 2M HCl solution and then extracted with ethyl acetate (3×). The combined organics were passed through a hydrophobic frit and then concentrated to dryness under vacuum.
Yield: 110 mg
MS (ESI) m/z: 425 (M+H)+.

(c). 3-(2-fluorophenyl)-N—((R)-1-hydroxy-3-(1H-indol-3-yl)propan-2-yl)-9-methoxy-8-(2-methoxyethoxy)-6H-benzo[c]chromene-2-carboxamide A solution of intermediate 45b (110 mg), diisopropylethylamine (136 µl), 1-ethyl-3-(3-dimethylaminopropyl)carbodiimide hydrochloride (75 mg), 1-hydroxybenzotriazole (53 mg) and D-tryptophanol (59 mg) in DMF (2 ml) was stirred at room temperature for 16 hours. Water was added and the mixture was extracted with ethyl acetate (3×). The combined organics were passed through a hydrophobic frit and then concentrated to dryness under vacuum. The crude residue was purified by preparative HPLC, eluting with water and increasing amounts acetonitrile
Yield: 69 mg
MS (ESI) m/z: 597 (M+H)+.
$^1$H NMR δ (ppm) (DMSO-$d_6$): 10.82 (1H, s), 7.92 (1H, d, J=8.2 Hz), 7.90 (1H, s), 7.63 (1H, d, J=7.9 Hz), 7.43 (1H, s), 7.40-7.33 (2H, m), 7.30 (1H, td, J=7.7, 1.8 Hz), 7.21-7.04 (4H, m), 7.03-6.94 (2H, m), 6.91 (1H, s), 5.16 (2H, d, J=2.4 Hz), 4.73 (1H, t, J=5.8 Hz), 4.17 (2H, t, J=4.5 Hz), 4.08-4.00 (1H, m), 3.94 (3H, s), 3.73 (2H, dd, J=5.6, 3.6 Hz), 3.48-3.42 (1H, m), 3.42-3.35 (4H, m), 2.94 (1H, dd, J=14.5, 6.2 Hz), 2.82 (1H, dd, J=14.5, 7.5 Hz).

Example 46

8-(allyloxy)-3-(2-fluorophenyl)-N—((R)-1-hydroxy-3-(1H-indol-3-yl)propan-2-yl)-9-methoxy-6H-benzo[c]chromene-2-carboxamide Compound 46 was prepared in an analogous fashion as described for example 45.
MS (ESI) m/z: 593 (M+H)+.

¹H NMR δ (ppm)(DMSO-d₆): 10.82 (1H, s), 7.94-7.87 (2H, m), 7.63 (1H, d, J=7.9 Hz), 7.44 (1H, s), 7.40-7.31 (2H, m), 7.30 (1H, td, J=7.7, 1.8 Hz), 7.23-7.04 (4H, m), 7.03-6.95 (2H, m), 6.91 (1H, s), 6.17-6.07 (1H, m), 5.47 (1H, dd, J=17.3, 1.9 Hz), 5.33 (1H, dd, J=10.5, 1.7 Hz), 5.15 (2H, d, J=2.3 Hz), 4.73 (1H, t, J=5.8 Hz), 4.64 (2H, d, J=5.4 Hz), 4.08-4.00 (1H, m), 3.94 (3H, s), 3.49-3.40 (1H, m), 3.37-3.30 (1H, m), 2.94 (1H, dd, J=14.5, 6.2 Hz), 2.82 (1H, dd, J=14.5, 7.5 Hz).

Example 47

3-(2-fluorophenyl)-N—((R)-1-hydroxy-3-(1H-indol-3-yl)propan-2-yl)-8-(2-hydroxyethoxy)-9-methoxy-6H-benzo[c]chromene-2-carboxamide Compound 47 was prepared in an analogous fashion as described for example 45.
MS (ESI) m/z: 583 (M+H)⁺.
¹H NMR δ (ppm)(DMSO-d₆): 10.81 (1H, s), 7.92 (1H, d, J=8.2 Hz), 7.87 (1H, s), 7.60 (1H, d, J=7.9 Hz), 7.40 (1H, s), 7.37-7.28 (2H, m), 7.27 (1H, td, J=7.7, 1.8 Hz), 7.18-7.01 (4H, m), 6.99-6.93 (2H, m), 6.88 (1H, s), 5.13 (2H, d, J=2.8 Hz), 4.92 (1H, t, J=5.4 Hz), 4.72 (1H, t, J=5.8 Hz), 4.07-3.99 (3H, m), 3.91 (3H, s), 3.76 (2H, q, J=5.1 Hz), 3.50-3.32 (2H, m), 2.92 (1H, dd, J=14.5, 6.1 Hz), 2.79 (1H, dd, J=14.5, 7.6 Hz).

Example 48

8-(2-(dimethylamino)ethoxy)-3-(2-fluorophenyl)-N—((R)-1-hydroxy-3-(1H-indol-3-yl)propan-2-yl)-9-methoxy-6H-benzo[c]chromene-2-carboxamide Compound 48 was prepared in an analogous fashion as described for example 45.
MS (ESI) m/z: 610 (M+H)⁺.
¹H NMR δ (ppm) (DMSO-d₆): 10.81 (1H, s), 7.92 (1H, d, J=8.1 Hz), 7.86 (1H, s), 7.60 (1H, d, J=7.9 Hz), 7.39 (1H, s), 7.36-7.29 (2H, m), 7.27 (1H, td, J=7.7, 1.8 Hz), 7.20-6.99 (4H, m), 7.00 (1H, s), 6.96 (1H, t, J=7.5 Hz), 6.88 (1H, s), 5.13 (2H, d, J=2.8 Hz), 4.72 (1H, t, J=5.7 Hz), 4.09 (2H, t, J=5.9 Hz), 4.05-3.97 (1H, m), 3.90 (3H, s), 3.49-3.42 (1H, m), 3.38-3.32 (1H, m), 2.91 (1H, dd, J=14.5, 6.2 Hz), 2.79 (1H, dd, J=14.5, 7.6 Hz), 2.67 (2H, t, J=5.9 Hz), 2.24 (6H, s).

Example 49

8-(cyclopropylmethoxy)-3-(2-fluorophenyl)-N—((R)-1-hydroxy-3-(1H-indol-3-yl)propan-2-yl)-9-s methoxy-6H-benzo[c]chromene-2-carboxamide Compound 49 was prepared in an analogous fashion as described for example 45.
MS (ESI) m/z: 593 (M+H)⁺.
¹H NMR δ (ppm)(DMSO-d₆): 10.82 (1H, s), 7.92 (1H, d, J=8.2 Hz), 7.89 (1H, s), 7.63 (1H, d, J=7.9 Hz), 7.42 (1H, s), 7.40-7.33 (2H, m), 7.30 (1H, td, J=7.7, 1.8 Hz), 7.23-7.05 (4H, m), 7.01-6.95 (2H, m), 6.90 (1H, s), 5.14 (2H, d, J=2.5 Hz), 4.73 (1H, t, J=5.8 Hz), 4.07-4.00 (1H, m), 3.94 (3H, s), 3.89 (2H, d, J=7.0 Hz), 3.49-3.41 (1H, m), 3.38-3.30 (1H, m), 2.94 (1H, dd, J=14.5, 6.2 Hz), 2.82 (1H, dd, J=14.5, 7.5 Hz), 1.34-1.25 (1H, m), 0.63 (2H, d, J=7.8 Hz), 0.37 (2H, d, J=5.0 Hz).

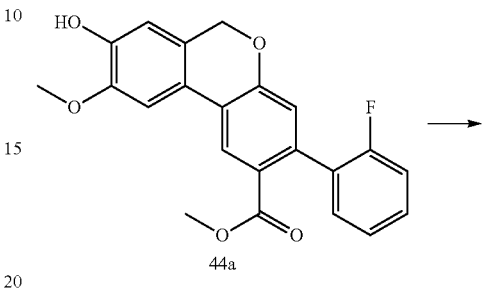

44a

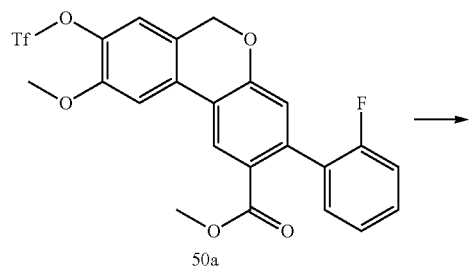

50a

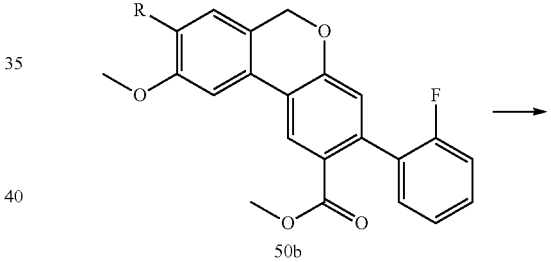

50b

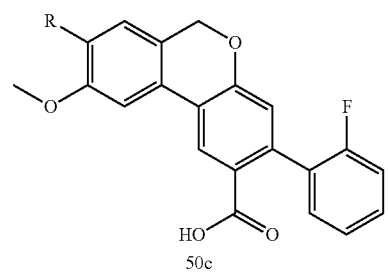

50c

R =

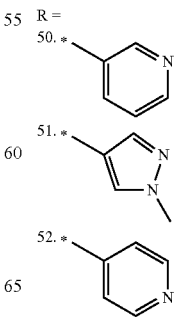

50.*

51.*

52.*

-continued

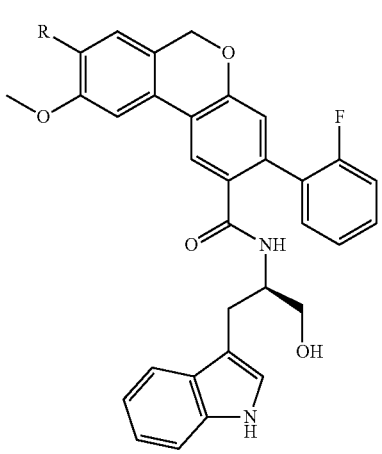

Example 50

3-(2-fluorophenyl)-N—((R)-1-hydroxy-3-(1H-indol-3-yl)propan-2-yl)-9-methoxy-8-(pyridin-3-v)-6H-benzo[c]chromene-2-carboxamide (a). methyl 3-(2-fluorophenyl)-9-methoxy-8-(trifluoromethylsulfonyloxy)-6H-benzo[c]chromene-2-carboxylate Triflic anhydride (575 µl) was slowly added to a 0° C. solution of intermediate 44a (1.0 g) and triethylamine (733 µl) in DCM (30 ml). The mixture was stirred at 0° C. for 45 minutes before being quenched with saturated aqueous sodium bicarbonate (30 ml). The product was extracted into DCM (3×) and the combined organics were passed through a hydrophobic frit and then concentrated to dryness under vacuum. The crude residue was purified chromatography on silica gel, eluting with petrol containing increasing amounts of diethyl ether.

Yield: 1.23 g $^1$H NMR δ (ppm)(CHCl$_3$-d): 8.34 (1H, s), 7.39 (1H, s), 7.38-7.32 (1H, m), 7.30 (1H, dd, J=7.5, 1.9 Hz), 7.23 (1H, td, J=3.7, 1.2 Hz), 7.10 (1H, ddd, J=10.2, 8.2, 1.16 Hz), 7.06 (1H, s), 1 to 6.97 (1H, s), 5.15 (2H, s), 4.04 (3H, s), 3.74-3.66 (3H, m).

(b). Methyl-3-(2-fluorophenyl)-9-methoxy-8-(pyridin-3-yl)-6H-benzo[c]chromene-2-carboxylate A solution of intermediate 50a (103 mg), 3-pyridineboronic acid (39 mg) and potassium carbonate (50 mg) in a 10:1 mixture of DME:water (2 ml) was degassed by gently bubbling through nitrogen for 20 minutes. Tetrakis(triphenylphosphine) palladium(0) (23 mg) was added and the mixture was degassed for a further 10 minutes before being sealed and heated to 90° C. for 16 hours. Water was added and the mixture was extracted into ethyl acetate (3×). The combined organics were passed through a hydrophobic frit and the solvents were removed under vacuum.

Yield: 88 mg

MS (ESI) m/z: 442 (M+H)$^+$.

(c). 3-(2-fluorophenyl-9-methoxy-8-(pyridin-3-v)-6H-benzo[c]chromene-2-carboxylic acid Sodium hydroxide (24 mg) in water (0.2 ml) was added to a solution of intermediate 50b (88 mg) in ethanol (1.8 ml) and the mixture was heated to 60° C. for 3 hours. The solvents were removed under vacuum. The crude residue was redissolved in water and washed with diethyl ether. The aqueous phase was acidified to pH 5 with a aqueous 2M HCl solution and was then extracted with ethyl acetate (3×). The combined organics were passed through a hydrophobic frit and the solvents were removed under vacuum.

Yield: 85 mg 10 cm_ESCI_Formic_MeCN; tR: 3.22 min; M+1: 428; 87.5%

(d). 3-(2-fluorophenyl)-N—((R)-1-hydroxy-3-(1H-indol-3-yl)propan-2-yl)-9-methoxy-8-(pyridin-3-yl)-6H-benzo[c]chromene-2-carboxamide A solution of intermediate 50c (111 mg), diisopropylethylamine (136 µl), 1-ethyl-3-(3-dimethylaminopropyl)carbodiimide hydrochloride (75 mg), 1-hydroxybenzotriazole (53 mg) and D-tryptophanol (59 mg) in DMF (2 ml) was stirred at room temperature for 16 hours. Water was added and the mixture was extracted with ethyl acetate (3×). The combined organics were passed through a hydrophobic frit and then concentrated to dryness under vacuum. The crude residue was purified by preparative HPLC, eluting with water and increasing amounts of acetonitrile.

Yield: 11 mg

MS (ESI) m/z: 600 (M+H)$^+$.

$^1$H NMR δ (ppm)(CHCl$_3$-d): 8.82 (1H, s), 8.60 (1H, d, J=4.8 Hz), 8.22 (1H, s), 8.04 (1H, s), 7.94 (1H, d, J=8.0 Hz), 7.60 (1H, d, J=7.9 Hz), 7.42-7.30 (5H, m), 7.26-7.05 (5H, m), 6.98 (1H, s), 6.94 (1H, d, J=2.3 Hz), 5.73 (1H, d, J=7.3 Hz), 5.22 (2H, s), 4.35-4.28 (1H, m), 3.94 (3H, s), 3.51 (2H, s), 2.79 (2H, d, J=7.0 Hz), 2.28 (1H, s).

Example 51

3-(2-fluorophenyl)-N—((R)-1-hydroxy-3-(1H-indol-3-yl)propan-2-yl)-9-methoxy-8-(1-methyl-1H-pyrazol-4-yl)-6H-benzo[c]chromene-2-carboxamide Compound 51 was prepared in an analogous fashion as described for example 50.

MS (ESI) m/z: 603 (M+H)$^+$.

$^1$H NMR δ (ppm)(DMSO-d$_6$): 10.82 (1H, s), 8.19 (1H, s), 8.00-7.96 (3H, m), 7.64-7.57 (2H, m), 7.48 (1H, s), 7.38-7.26 (3H, m), 7.20-7.15 (2H, m), 7.12 (1H, t, J=7.5 Hz), 7.05 (1H, t, J=3.9 Hz), 6.97 (1H, t, J=3.7 Hz), 6.92 (1H, s), 5.18 (2H, d, J=3.4 Hz), 4.73 (1H, t, J=5.7 Hz), 4.08-3.95 (4H, m), 3.90 (3H, s), 3.48-3.41 (1H, m), 3.39-3.33 (1H, m), 2.92 (1H, dd, J=14.5, 6.2 Hz), 2.80 (1H, dd, J=14.4, 7.6 Hz).

Example 52

3-(2-fluorophenyl)-N—((R)-1-hydroxy-3-(1H-indol-3-yl)propan-2-yl)-9-methoxy-8-(pyridin-4)-6H-benzo[c]chromene-2-carboxamide Compound 52 was prepared in an analogous fashion as described for example 50.

MS (ESI) m/z: 600 (M+H)$^+$.

$^1$H NMR δ (ppm)(DMSO-d$_6$): 10.83 (1H, s), 8.66 (2H, d, J=4.6 Hz), 8.08 (1H, s), 7.97 (1H, d, J=8.1 Hz), 7.65-7.60 (4H, m), 7.46 (1H, s), 7.42-7.32 (3H, m), 7.24-7.13 (3H, m), 7.08 (1H, t, J=7.6 Hz), 7.03-6.95 (2H, m), 5.25 (2H, d, J=5.0 Hz), 4.74 (1H, t, J=5.7 Hz), 4.10-4.02 (1H, m), 4.00 (3H, s), 3.48-3.42 (1H, m), 3.38-3.32 (1H, m), 2.94 (1H, dd, J=14.5, 6.3 Hz), 2.83 (1H, dd, J=14.5, 7.5 Hz).

85  86
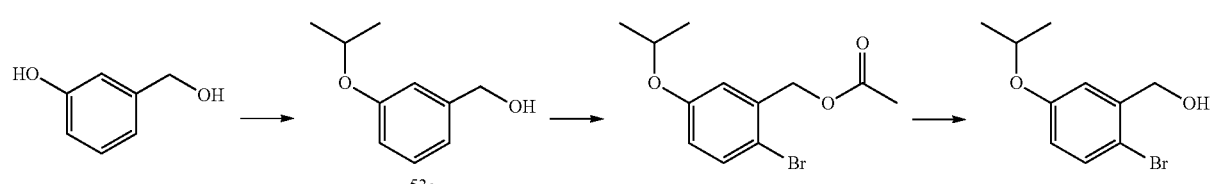
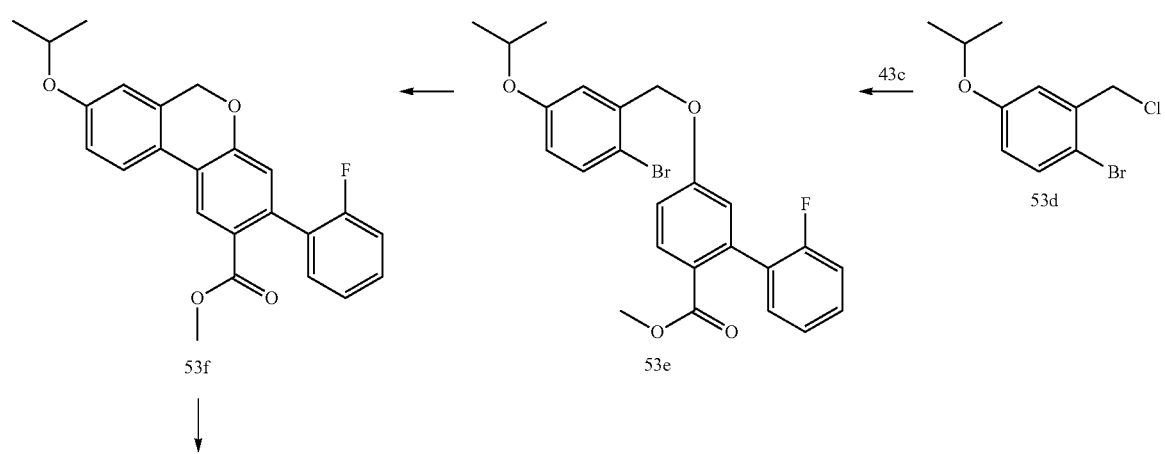
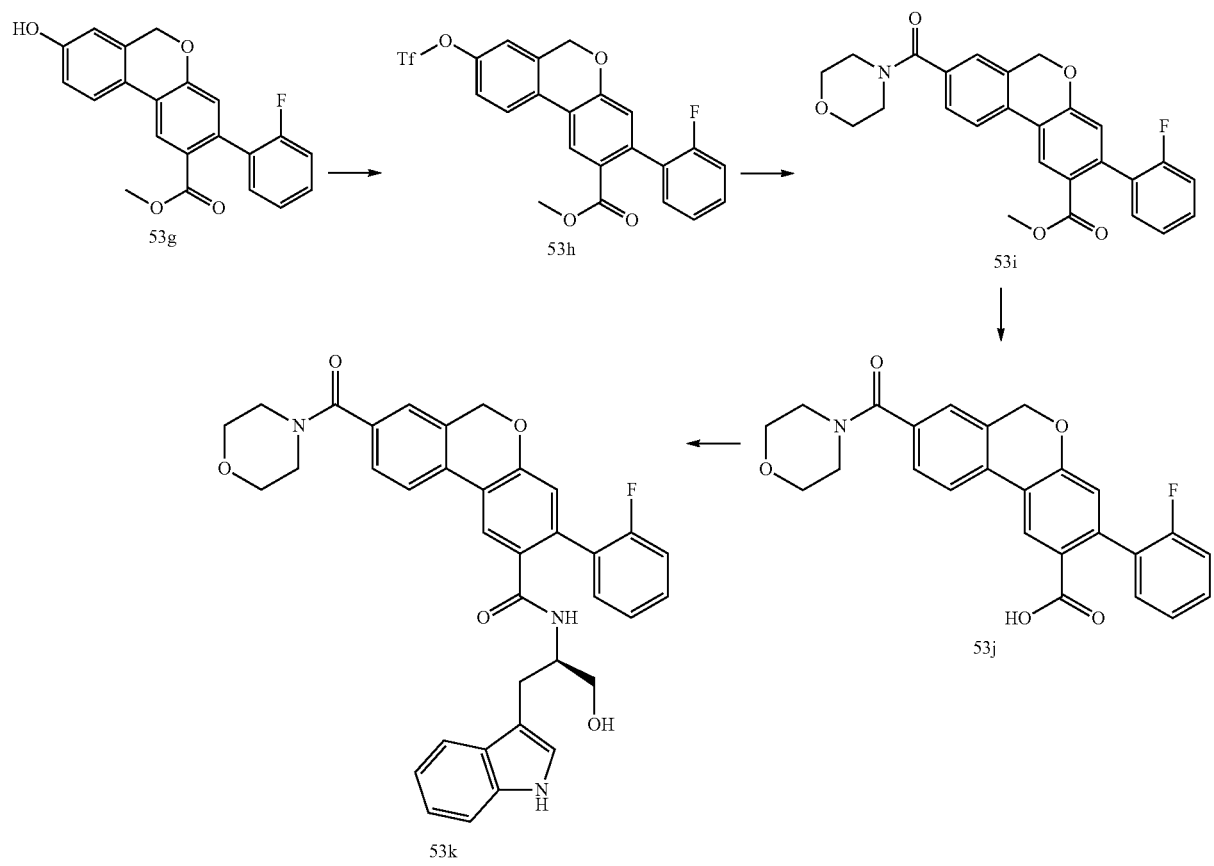

Example 53

3-(2-fluorophenyl)-N—((R)-1-hydroxy-3-(1H-indol-3-yl)propan-2-yl)-8-(morpholine-4-carbonyl)-6H-benzo[c]chromene-2-carboxamide

(a). (3-isopropoxyphenyl)methanol

To a mixture of 3-(hydroxymethyl)phenol (10 g) and potassium carbonate (27.2 g) in DMF (100 ml) was added 2-bromo-propane (14.8 g), the reaction was heated to 90° C. overnight. The reaction mixture was filtered and the filtrate was concentrated and purified by chromatography on silica gel, eluting with petrol:ethyl acetate=5:1.

Yield: 5 g $^1$H NMR δ (ppm)(DMSO-d$_6$): 7.161 (t, 1H, J=7.6 Hz), 6.803 (d, 2H, J=8.0 Hz), 6.720 (d, 1H, J=8.0 Hz), 5.109 (t, 1H, J=6.0 Hz), 4.515-4.575 (m, 1H), 4.413 (d, 2H, J=6.0 Hz), 1.217 (d, 6H, J=6.0 Hz).

(b). 2-bromo-5-isopropoxybenzyl acetate

To a solution of compound 53a (5 g) in acetic acid (50 ml) was added bromine (6.4 g) in acetic acid (10 ml) dropwise at 10° C., the reaction mixture was stirred at room temperature for 2 hours. The solution was adjusted to pH=8 with a saturated aqueous NaHCO$_3$ solution, the aqueous layer was extracted with ethyl acetate twice. The combined organic layers were dried (MgSO$_4$), filtered and concentrated in vacuo. The residue was purified by chromatography on silica gel, eluting with petrol: ethyl acetate 10:1.

Yield: 6 g $^1$H NMR δ (ppm)(CHCl$_3$-d): 7.357 (d, 1H, J=8.8 Hz), 6.872 (d, 1H, J=2.8 Hz), 6.652 (dd, 1H, J=3.2 Hz, J=8.8 Hz), 5.063 (s, 2H), 4.415-4.476 (m, 1H), 2.072 (s, 3H), 1.256 (d, 6H, J=6.0 Hz).

(c). methyl (2-bromo-5-isopropoxyphenyl)methanol

To a solution of compound 53b (6 g) in THF (30 ml) was added a aqueous 2N sodium hydroxide solution (30 ml), the reaction was stirred at room temperature overnight. The reaction mixture was diluted with ethyl acetate and washed with water. The aqueous layer was extracted again with ethyl acetate. The combined organic layers were dried (MgSO$_4$), filtered and concentrated in vacuo.

Yield: 4.8 g $^1$H NMR δ (ppm)(DMSO-d$_6$): 7.373 (d, 1H, J=8.8 Hz), 7.030 (d, 1H, J=2.8 Hz), 6.724 (dd, 1H, J=2.8 Hz, J=8.8 Hz), 5.400 (t, 1H, J=5.6 Hz), 4.519-4.579 (m, 1H), 4.410 (d, 2H, J=5.6 Hz), 1.222 (d, 6H, J=5.6 Hz).

(d). 1-bromo-2-(chloromethyl)-4-isopropoxybenzene

To a solution of compound 53c (4.8 g,) in DMF (40 ml) was added thionylchloride (5 ml) dropwise at 0° C., the reaction was heated to 50° C. for 2 hours. The mixture was allowed to cool to room temperature and the solution was poured into icewater. The mixture was extracted with ethyl acetate twice. The organic layer was dried (MgSO$_4$), filtered and concentrated in vacuo.

Yield: 5 g $^1$H NMR δ (ppm)(CHCl$_3$-d): 7.409 (d, 1H, J=8.8 Hz), 6.961 (d, 1H, J=3.2 Hz), 6.693 (dd, 1H, J=3.2 Hz, J=8.8 Hz), 4.468-4.524 (m, 3H), 1.313 (d, 6H, J=6.0 Hz).

(e). methyl 5-(2-bromo-5-isopropoxybenzyloxy)-2'-fluorobiphenyl-2-carboxylate To a solution of compound 43c (2.5 g) in DMF (30 ml) was added NaH (0.8 g) at 0° C. under a nitrogen atmosphere, the reaction was stirred for 30 minutes, compound 53d (3 g) was added and the reaction mixture was stirred at room temperature for 1 hour. The solution was poured into icewater and extracted with ethyl acetate (3×). The combined organic layers were dried (MgSO$_4$), filtered and concentrated in vacuo. The residue was purified by chromatography on silica gel, eluting with petrol: ethyl acetate 5:1.

Yield: 2.5 g $^1$H NMR δ (ppm)(DMSO-d$_6$): 7.881 (d, 1H, J=8.8 Hz), 7.501 (d, 1H, J=8.8 Hz), 7.314-7.415 (m, 2H), 7.131-7.253 (m, 4H), 6.986 (d, 1H, J=2.4 Hz), 6.861 (dd, 1H, J=3.2 Hz, J=8.8 Hz), 5.147 (s, 2H), 4.545-4.605 (m, 1H), 3.555 (s, 3H), 1.201 (d, 6H, J=6.0 Hz).

(f). methyl 3-(2-fluorophenyl)-8-isopropoxy-6H-benzo[c]chromene-2-carboxylate Under a nitrogen atmosphere, to a mixture of compound 53e (2.5 g), Tricyclohexylphosphine fluoroboric acid (0.2 g) and potassium carbonate (1.38 g,) in dimethylacetamide potassium carbonate (50 ml) was added palladium(II) acetate (0.2 g), the reaction mixture was heated to 100° C. overnight. The mixture was poured into water and extracted with ethyl acetate (3×). The combined organic layers were dried (MgSO$_4$), filtered and concentrated in vacuo. The residue was purified by chromatography on silica gel, eluting with petrol: ethyl acetate 5:1.

Yield: 1.5 g $^1$H NMR δ (ppm)(CHCl$_3$-d): 8.311 (s, 1H), 7.705 (d, 1H, J=8.4 Hz), 7.272-7.351 (m, 2H), 7.164-7.204 (m, 1H), 6.896-6.927 (m, 2H), 6.661 (d, 1H, J=2.4 Hz), 5.152 (s, 2H), 4.553-4.614 (m, 1H), 3.691 (s, 3H), 1.353 (d, 6H, J=6.0 Hz).

(g). methyl 3-(2-fluorophenyl)-8-hydroxy-6H-benzo[c]chromene-2-carboxylate

To a solution of compound 53f (1.4 g,) in DCM (50 ml) was added aluminium chloride (1.4 g) under a nitrogen atmosphere, the reaction was stirred at 0° C. for 1 hour, the reaction mixture was quenched with water. The organic layer was separated, dried (MgSO$_4$), filtered and concentrated in vacuo.

Yield: 1 g

MS (ESI) m/z: 351 (M+H)$^+$.

(h). methyl 3-(2-fluorophenyl)-8-(trifluoromethylsulfonyloxy)-6H-benzo[c]chromene-2-carboxylate To a solution of compound 53 g (1 g) and triethylamine (1.5 g) in DCM (30 ml) was added trifluoromethanesulfonic anhydride (2.82 g) dropwise at 0° C., the reaction mixture was stirred at room temperature for 1 hour. The solvent was evaporated and the residue was purified by chromatography on silica gel, eluting with petrol: ethyl acetate 5:1.

Yield: 0.4 g $^1$H NMR δ (ppm)(CHCl$_3$-d): 8.372 (s, 1H), 7.860 (d, 1H, J=8.8 Hz), 7.270-7.358 (m, 3H), 7.180-7.220 (m, 1H), 7.064-7.114 (m, 2H), 6.959 (s, 1H), 5.211 (s, 2H), 3.699 (s, 3H).

(i). methyl 3-(2-fluorophenyl)-8-(morpholine-4-carbonyl)-6H-benzo[c]chromene-2-carboxylate To a solution of compound 53h (100 mg), morpholine (43 mg), triethylamine (50 mg) and 1,3-bis(diphenylphosphino)propane (16 mg) in DMF (3 ml) was added palladium(II) acetate (8 mg. The suspension was degassed under vacuum and purged with carbonmonoxide several times, the mixture was stirred under carbonmonoxide atmosphere at 80° C. for 2 hours and filtered. The solvent was evaporated and the residue was purified by preparative TLC, eluting with ethyl acetate.
Yield: 60 mg
MS (ESI) m/z: 448 (M+H)$^+$.

(j). 3-(2-fluorophenyl)-8-(morpholine-4-carbonyl)-6H-benzo[c]chromene-2-carboxylic acid To a solution of compound 53i (60 mg) in methanol (2 ml) was added a aqueous 2N sodium hydroxide solution (1 ml), the reaction was heated to 60° C. for 2 hours. The reaction mixture was poured into water and the pH was adjusted to pH 7 with a aqueous 2N HCl solution. This mixture was extracted with ethyl acetate (5×). The combined organic layers were dried (MgSO$_4$), filtered and concentrated in vacuo.
Yield 40 mg
MS (ESI) m/z: 434 (M+H)$^+$.

(k). 3-(2-fluorophenyl)-N—((R)-1-hydroxy-3-(1H-indol-3-yl)propan-2-yl)-8-(morpholine-4-carbonyl)-6H-benzo[c]chromene-2-carboxamide To a solution of compound 53j (40 mg), D-tryptophanol (20 mg) and triethylamine (30 mg) in DMF (2 ml) was added HATU (38 mg), the reaction was stirred at room temperature for 1 hour. The crude product was concentrated and purified by preparative HPLC, eluting with water and increasing amounts of acetonitrile.
Yield: 10 mg
MS (ESI) m/z: 606 (M+H)$^+$.
$^1$H NMR δ (ppm)(CHCl$_3$-d): 7.980 (s, 1H), 7.902 (s, 1H), 7.575 (d, 1H, J=8.0 Hz), 7.524 (d, 1H, J=6.8 Hz), 7.302-7.358 (m, 2H), 7.238 (t, 2H, J=7.2 Hz), 6.970-7.151 (m, 5H), 6.878 (s, 2H), 5.695 (d, 1H, J=6.8 Hz), 5.116 (s, 2H), 4.195-4.241 (m, 1H), 3.468-3.706 (m, 11H), 2.757 (d, 2H, J=5.6 Hz).

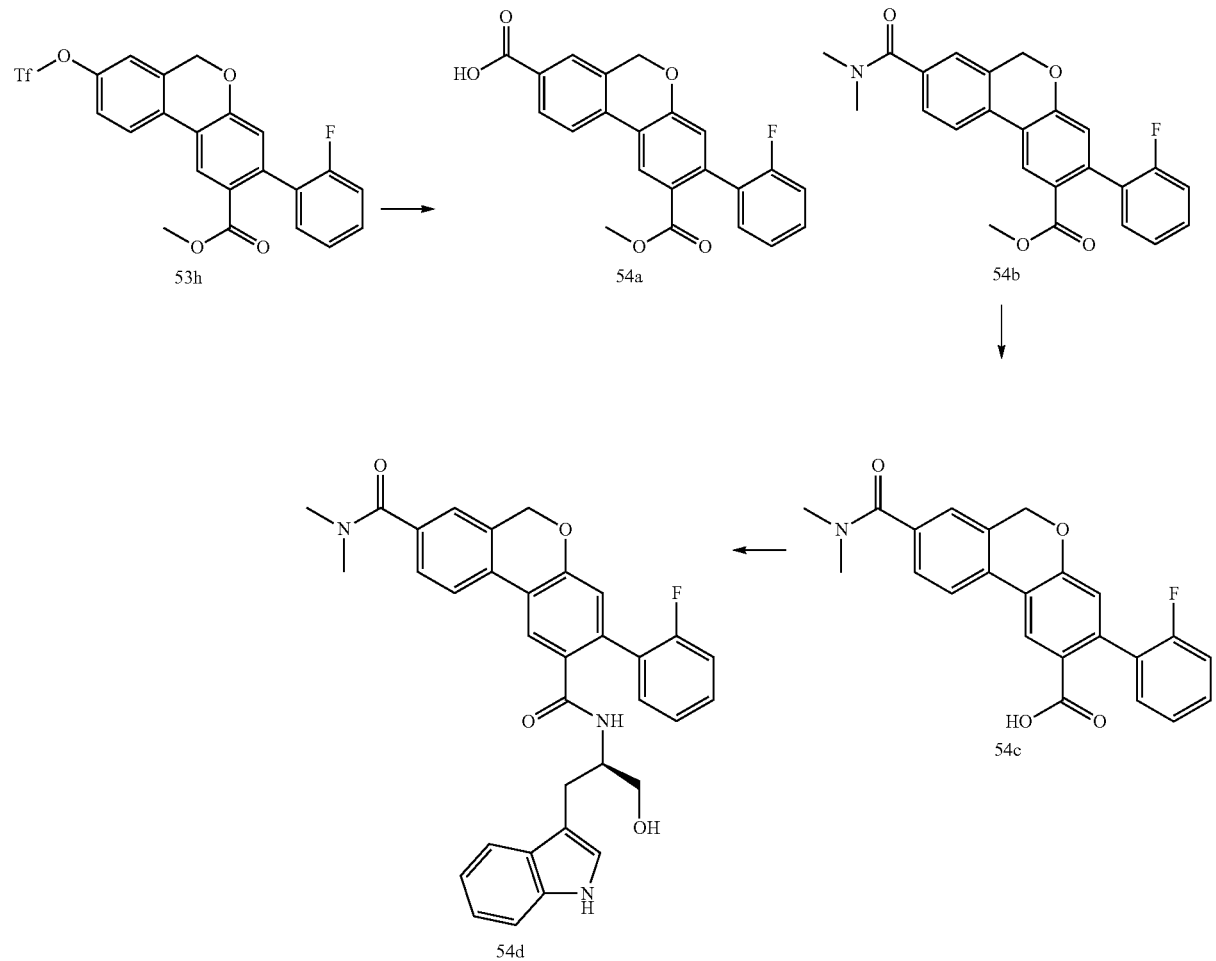

Example 54

3-(2-fluorophenyl)-N2-((R)-1-hydroxy-3-(1H-indol-3-yl)propan-2-yl)-N8,N8-dimethyl-6H-benzo[c]chromene-2,8-dicarboxamide (a). 3-(2-fluorophenyl)-2-(methoxycarbonyl)-6H-benzo[c]chromene-8-carboxylic acid To a solution of compound 53h (50 mg), triethylamine (30 mg) and 1,3-bis(diphenylphosphino)propane (16 mg) in DMF (2 ml) and water (1 ml) was added palladium(II) acetate (8 mg), the suspension was degassed under vacuum and purged with carbonmonoxide several times, the reaction mixture was stirred under carbonmonoxide atmosphere at 80° C. overnight. The reaction mixture was filtered and the filtrate was poured into water and extracted with ethyl acetate (3×). The combined organic layers were dried (MgSO$_4$), filtered and concentrated in vacuo.

Yield: 50 mg
MS (ESI) m/z: 379 (M+H)$^+$.

(b). methyl 8-(dimethylcarbamoyl)-3-(2-fluorophenyl)-6H-benzo[c]chromene-2-carboxylate To a solution of compound 54a (50 mg), dimethylamine hydrochloride (16 mg) and triethylamine (30 mg) in DMF (2 ml) was added HATU (57 mg), the reaction was heated to 50° C. for 20 minutes. The reaction mixture was poured and extracted with ethyl acetate (3×). The combined organic layers were dried (MgSO$_4$), filtered and concentrated in vacuo.

Yield 40 mg
MS (ESI) m/z: 406 (M+H)$^+$.

(c). 8-(dimethylcarbamoyl)-3-(2-fluorophenyl)-6H-benzo[c]chromene-2-carboxylic acid To a solution of compound 54b (40 mg,) in methanol (2 ml) was added a aqueous 2N sodium hydroxide solution (1 ml), the reaction mixture was heated to 60° C. for 2 hours. The reaction mixture was poured into water, adjusted to pH4 with a aqueous 2N HCl solution and extracted with ethyl acetate (3×). The combined organic layers were dried (MgSO$_4$), filtered and concentrated in vacuo.

Yield: 25 mg
MS (ESI) m/z: 392 (M+H)$^+$.

(d). 3-(2-fluorophenyl)-N2-((R)-1-hydroxy-3-(1H-indol-3-yl)propan-2-yl)-N8,N8-dimethyl-6H-benzo[c]chromene-2,8-dicarboxamide To a solution of compound 54c (25 mg), D-tryptophanol (20 mg) and triethylamine (30 mg) in DMF (2 ml) was added HATU (30 mg), the reaction was heated to 50° C. for 10 minutes. The reaction mixture was concentrated in vacuo and purified by preparative HPLC, eluting with water and increasing amounts of acetonitrile.

Yield: 18 mg
MS (ESI) m/z: 564 (M+H)$^+$.
$^1$H NMR δ (ppm)(CHCl$_3$-d): 8.154 (s, 1H), 7.936 (s, 1H), 7.625 (d, 1H, J=2.0 Hz), 7.605 (d, 1H, J=2.4 Hz), 7.398-7.458 (m, 2H), 7.309-7.360 (m, 2H), 7.060-7.265 (m, 5H), 6.964-6.981 (m, 2H), 5.909 (d, 1H, J=6.8 Hz), 5.194 (s, 2H), 4.320-4.338 (m, 1H), 3.578-3.589 (m, 2H), 3.180 (s, 3H), 3.085 (s, 3H), 2.855-2.883 (m, 2H).

Example 55

3-(2-fluorophenyl)-N—((R)-1-hydroxy-3-(1H-indol-3-yl)propan-2-yl)-8,9-(1',3'-dioxolo)-6H-benzo[c]chromene-2-carboxamide Compound 55 was prepared in an analogous fashion as described for example 36, but starting from 5-bromo-6-bromomethyl-1,3-benzodioxole.

MS (ESI) m/z: 537 (M+H)$^+$.
$^1$H NMR δ (ppm) (DMSO-d$_6$): 10.81 (1H, s), 7.99 (1H, d, J=8.3 Hz), 7.77 (1H, s), 7.63 (1H, d, J=7.9 Hz), 7.42 (1H, s), 7.36-7.32 (2H, m), 7.24 (1H, t, J=1.8 Hz), 7.13-7.04 (4H, m), 6.99-6.94 (2H, m), 6.88 (1H, s), 6.12 (2H, s), 5.10 (2H, s), 4.73 (1H, t, J=0.8 Hz), 4.08-3.99 (1H, m), 3.45-3.43 (1H, m), 3.34-3.32 (1H, m), 2.98-2.75 (2H, m).

Example 56

N—((R)-1-hydroxy-3-(1H-indol-3-yl)propan-2-yl)-8,9-(1',3'-dioxolo)-3-(3-methylthiophen-2-yl)-6H-benzo[c]chromene-2-carboxamide Compound 55 was prepared in an analogous fashion as described for example 39, but starting from 5-bromo-6-bromomethyl-1,3-benzodioxole.

MS (ESI) m/z: 539 (M+H)$^+$.
$^1$H NMR δ (ppm) (DMSO-d$_6$): 10.80 (1H, s), 7.73-7.69 (2H, m), 7.62 (1H, d, J=7.9 Hz), 7.39-7.32 (3H, m), 7.10 (1H, d, J=2.3 Hz), 7.07 (1H, t, J=7.6 Hz), 6.97 (1H, t, J=7.5 Hz), 6.94 (1H, s), 6.87 (1H, d, J=5.1 Hz), 6.84 (1H, s), 6.11 (2H, s), 5.09 (2H, s), 4.68 (1H, t, J=5.7 Hz), 4.04-4.01 (1H, m), 3.42-3.38 (1H, m), 3.33-3.32 (1H, m), 2.90-2.76 (2H, m), 2.03 (3H, S).

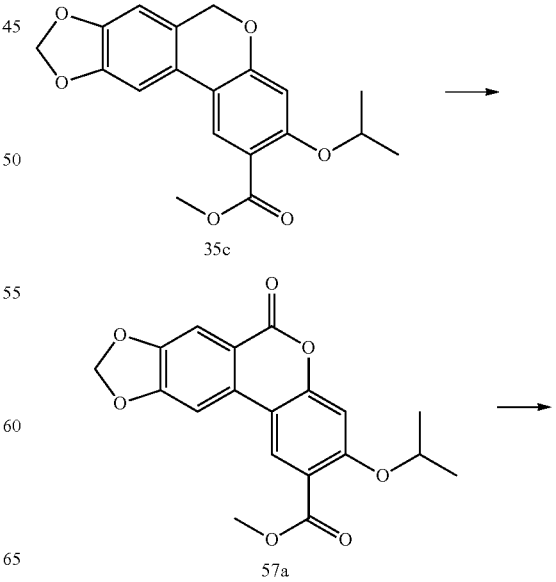

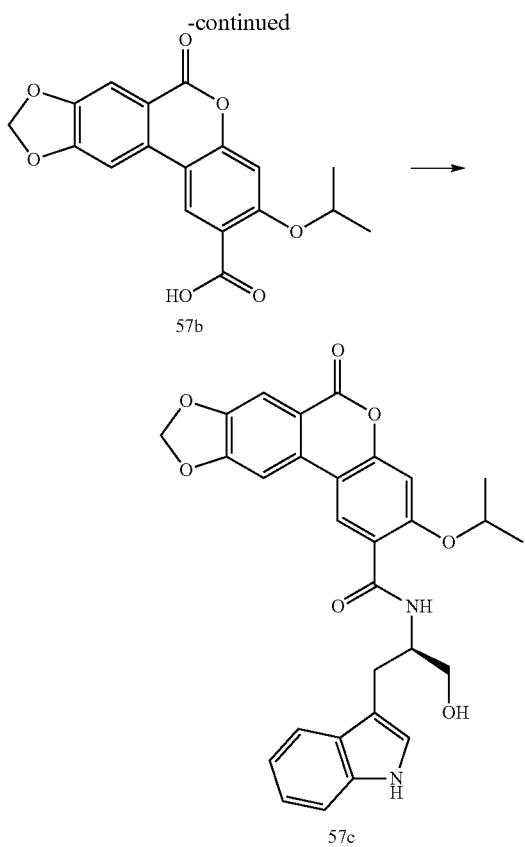

57b

57c

Example 57

N—((R)-1-hydroxy-3-(1H-indol-3-yl)propan-2-y)-8,9-(1',3'-dioxolo)-3-(3-isopropoxy)-6-oxo-6H-benzo[c]chromene-2-carboxamide (a). methyl 8,9-(1',3'-dioxolo)-3-isopropoxy-6-oxo-6H-benzo[c]chromene-2-carboxylate To a solution of compound 35c in a mixture of acetonitrile and water (9:1) (5.5 ml) under a nitrogen atmosphere was added 4-acetamido-2,2,6,6-tetramethyl-1-oxopiperidinium tetrafluoroborate. The reaction mixture was stirred at room temperature for 4 hrs. The reaction was quenched with a aqueous 10% $Na_2CO_3$ solution and extracted with ethyl acetate. The water layer was washed with ethyl acetate and the combined organic layers were washed with brine, dried ($Na_2SO_4$), filtered and concentrated in vacuo. The residue was purified by chromatography on silica gel with heptane and increasing amounts of ethyl acetate.
Yield: 43.7 mg
MS (ESI) m/z: 357 (M+H)$^+$.

(b). 8,9-(1',3'-dioxolo)-3-isopropoxy-6-oxo-6H-benzo[c]chromene-2-carboxylic acid Compound 57a (22 mg) was suspended in ethanol (4 ml) under an N2 atmosphere. A aqueous 2M sodium hydroxide solution (0.309 ml) was added and the reaction mixture was held at 60° C. for 5 hours. The reaction mixture was allowed to cool to ambient temperature and was quenched with water and ethyl acetate and neutralised with a aqueous 2N HCl solution. The reaction mixture was extracted and the water-layer was washed with ethyl acetate. The combined organic layers were washed with brine, dried ($Na_2SO_4$), filtered and concentrated under reduced pressure.
Yield 22 mg (c). N—((R)-1-hydroxy-3-(1H-indol-3-yl)propan-2-yl)-8,9-(1',3'-dioxolo)-3-(3-isopropoxy)-6-oxo-6H-benzo[c]chromene-2-carboxamide Compound 57b (22 mg) was suspended in DMF (p.a) (2 ml) under an N2 atmosphere. Dipea (0.022 ml), 1-ethyl-3-(3-dimethylaminopropyl) carbodiimide (13 mg) and hydroxybenzotriazole (9.12 mg) were added and the reaction mixture was held at ambient temperature for 10 minutes. D-tryptophanol (17 mg) was added and the reaction was held at ambient temperature for 7 hours. The reaction was quenched with water and the reaction mixture was extracted with ethyl acetate. The water layer was washed with ethyl acetate and the combined organic layers were washed with water (2×), brine, dried (MgSO4), filtered and concentrated under reduced pressure. The crude product was purified by chromatography on silica gel, eluting with heptane and increasing amounts ethyl acetate.
Yield: 9.9 mg
MS (ESI) m/z: 515 (M+H)$^+$.

Example 58

(R)-2-isopropoxy-N-(1-hydroxy-3-(1H-indol-3-yl)propan-2-yl)-6,7-dimethoxy-9,10-dihydrophenanthrene-3-carboxamide Compound 58 was prepared in an analogous fashion as described for compound 8.

Example 59

Antagonistic Activity of Compounds at the Human FSH Receptor Expressed in CHO Cells Antagonistic activity of the compounds at the human FSH receptor was determined in Chinese Hamster Ovary (CHO) cells stably transfected with the human FSH receptor and cotransfected to with a cAMP responsive element (CRE)/promoter directing the expression of a firefly luciferase reporter gene. Binding of the compounds to the Gs protein-coupled FSH receptor will result in an increase of cAMP, which in turn will induce an increased transactivation of the luciferase reporter. The cells (7,500 cells/well of a 384 well plate) were incubated in Dulbecco' minimal essential F12 modified medium (Invitrogen), supplemented with 1 µg/ml bovine insulin, 5 µg/ml human apo-transferrin, 100 U/ml penicillin G and 100 µg/ml streptomycin with the test compounds (concentration between 0.316 nM and 10.0 µM) in duplicate together with 49 µM recFSH (which, at this concentration in the absence of test compound, induces 80% of the maximal luciferase stimulation) in a humidified atmosphere (95%) at 5-7% CO2 and 37° C. The final concentration of DMSO was 1%. After 4 hours of incubation, plates were allowed to adjust to room temperature for 1 hour. Then, SteadyLite (PerkinElmer) solution was added to the wells and cells were allowed to lyse for at least 1 hour at room temperature. Subsequently, luciferase activity was measured in a luminescence counter. The signal is expressed as counts per second (cps). The IC50 (concentration of test compound causing half-maximal (50%) inhibition of the maximally attainable inhibition of the luciferase stimulation by the compound) and efficacy of the compounds were determined using the software program MathIQ (version 2.3, ID Business Solutions Limited).

The compounds of all examples have an IC50 of $10^{-5}$ M or lower. The compounds of examples 12-15, 26, 31, 33, 35 and 57 have an IC50 of less than $10^{-6}$ M and more than $10^{-7}$ M. The compounds of examples 1-11, 18-25, 28-30, 34, 36-56 and 58 have an IC50 of less than $10^{-7}$ M.

Example 60

Functional Assay for Assessing hFSHR Antagonistic Activity of Compound of Example 58 in Human Granulosa Cell Cultures Human granulosa cells were obtained in the course of follicular aspiration for retrieval of matured oocytes during routine IVF procedures approximately 36 hours after hCG administration to the patient. Follicular fluid was collected as one batch per patient and after oocyte removal centrifuged for 5 minutes at 350 g at room temperature (RT). The pellet was resuspended in 5 ml collagenase (0.1%) containing isolation medium, layered on 5 ml of Histopaque-1077 and centrifuged (450 g for 20 minutes, RT) to separate the granulosa cells from the erythrocytes. The granulosa cells and other mononuclear cells (e.g. lymphocytes) were obtained from the interface and washed once with isolation medium (450 g, 20 minutes). After aspiration of the supernatant, the pellet was resuspended in isolation medium and transported from the hospital to the laboratory. The granulosa cells are pelleted by centrifugation (350 g, 5 minutes) and resuspended in a small volume of culture medium with 10% fetal calf serum (FCS). To facilitate cell dispersal the suspension was subjected to gentle mechanical dissociation.

Cell viability was determined by Trypan Blue exclusion and the granulosa cells were plated at a density of 25,000 viable cells/200 µl/well in culture medium with 10% FCS in collagen coated 96-wells plates, and cultured at 37° C. under a humidified atmosphere supplemented with 5% $CO_2$. Every 72 hours the cells are washed once with pre-warmed culture medium to remove dead cells, debris and non-adherent cells. Seven days after the start of the culture, the cells are washed again with culture medium. Medium was aspirated and 250 µL isolation medium with isobutylmethylxanthine (IBMX) with human recombinant FSH (hrecFSH: 0 and 250 mU/mL) or with hrecFSH (250 mU/mL) in combination with the compound of example 58 was incubated for an additional 48 hours at 37° C., 5% $CO_2$. All test conditions were performed in triplicate. Subsequently, supernatant was collected in 96 well plates. Finally 25 µL supernatant was transferred to a new 96 deep-well plate and used for the determination of cAMP levels with the cAMP EIA kit (Amersham Life Sciences, cat. no RPN 225). Immediately after aspiration of the supernatant of the granulosa cells, 150 µL culture medium supplemented with 10 µM testosterone, was added to the wells. After 2 hours of incubation at 37° C., 5% $CO_2$, the supernatant was collected and used for the determination of estradiol levels with an estradiol-ELISA (DRG instruments, art. no. EIA-2693). Supernatants were diluted 1:300 in Dulbecco's phosphate buffered saline (DPBS, Hyclone Cat. No. SH30028.03) and a self-made calibration curve of estradiol in DPBS was used for the determination of estradiol levels in the supernatants.

The invention claimed is:
1. A compound according to Formula I

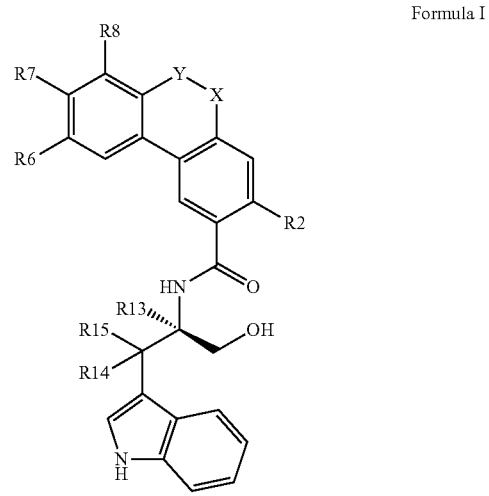

Formula I or a pharmaceutically acceptable salt thereof, wherein
Y—X is $CH_2$—$CH_2$, —C(O)O— or —$CH_2$O—
R2 is phenyl, (1-6C)alkyl, (2-8C)-heteroaryl, benzoyl, (2-8C)heteroarylcarbonyl, (1-8C)alkoxy, (3-6C)cycloalkyl, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or
R2 is (2-6C)alkenyl, (2-6C)alkynyl, (1-6C)alkylcarbonyl, (2-6C)alkenylcarbonyl, (2-6C)alkynylcarbonyl, (3-6C)cycloalkylcarbonyl, (3-6C)alkenoxy, (3-6C)cycloalkyl(1-4C)alkoxy, phenyl(1-4C)alkoxy or (2-8C)heteroaryl(1-4C)alkoxy;
R6 is hydroxy or H, or
R6 is (1-6C)alkyl, (2-6C)alkenyl, (2-6C)alkynyl, (1-4C)alkoxy, (3-6C)alkenoxy, (3-6C)cycloalkyl(1-4C)alkoxy, (3-6C)cycloalkoxy, (3-6C)heterocycloalkyl(1-4C)alkoxy, halogen, cyano, the alkyl or alkoxy moieties of which may optionally be substituted with one or more substituents selected from R10, or
R6 together with R7 is —O—$(CH_2)_n$-O— in which n is 1-3 and in which the $CH_2$ moiety may optionally be substituted by one or more (1-3C)alkyl substituents, or
R6 and R7 may be joined in a (3-6C)cycloalkyl ring;
R7 is hydroxy, H, or
R7 is (1-6C)alkyl, (2-6C)alkenyl, (2-6C)alkynyl, (1-4C)alkoxy, (3-6C)alkenoxy, (3-6C)cycloalkyl, (3-6C)cycloalkyl(1-4C)alkoxy, (3-6C)cycloalkoxy, (3-6C)heterocycloalkyl(1-4C)alkoxy, (3-6C)heterocycloalkoxy, (2-6C)heterocycloalkylcarbonyl, (di)[1-4C]alkylaminocarbonyl or (2-6C)heterocycloalkyl, the alkyl, alkoxy or (hetero)cycloalkyl moieties of which may optionally be substituted with one or more substituents selected from R11, or
R7 is (2-8C)heteroaryl, phenyl, phenyl(1-4C)alkoxy, (2-8C)heteroaryl(1-4C)alkoxy, the phenyl or heteroaryl moieties of which may optionally be substituted with one or more substituents selected from R11, or
R7 together with R6 is —O—$(CH_2)_n$-O— in which n is 1-3 and in which the $CH_2$ moiety may optionally be substituted by one or more (1-3C)alkyl substituents or R7 and R6 may be joined in a (3-6C)cycloalkyl ring;
R8 is H or (1-4C)alkoxy;
R10 is hydroxy, amino, halogen, cyano, nitro, trifluoromethyl, (1-4C)alkoxy, (1-4C)alkyl, aminocarbonyl or (di)[1-4C]alkylamino;
R11 is hydroxy, amino, halogen, cyano, nitro, trifluoromethyl, (1-4C)alkoxy, (di)[1-4C]alkyl]amino or (1-4C)alkyl;
R12 is hydroxy, amino, halogen, cyano, nitro, trifluoromethyl, (1-4C)alkoxy, (1-4C)alkyl, aminocarbonyl or (di)[1-4C]alkylamino;
R13 is H or (1-3C)alkyl;
R14 and R15 are independently H or (1-3C)alkyl, or
R14 and R15 may be joined in a (3-6C)cycloalkyl ring.

2. The compound according to claim 1 wherein
R2 is phenyl, (1-6C)alkyl, (2-8C)-heteroaryl, (1-8C)alkoxy, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or
R2 is (2-6C)alkenyl, (3-6C)alkenoxy, (3-6C)cycloalkyl(1-4C)alkoxy, phenyl(1-4C)alkoxy or (2-8C)heteroaryl(1-4C)alkoxy.

3. The compound according to claim 2 wherein R13, R14 and R15 is H.

4. The compound according to claim 3 wherein n, if R6 is combined with R7 is 1.

5. The compound according to claim 4 wherein R2 is phenyl, (1-6C)alkyl, (2-8C)-heteroaryl, (1-8C)alkoxy, (3-6C)cycloalkoxy, all alkyl or alkoxy moieties of which may optionally be substituted with one or more substituents selected from R10 and the phenyl or heteroaryl moieties of which may optionally be substituted with one or more substituents selected from R12, or
R2 is (2-6C)alkenyl, (3-6C)alkenoxy, (3-6C)cycloalkyl(1-4C)alkoxy or phenyl(1-4C)alkoxy.

6. The compound according to claim 3 wherein
R6 is hydroxy, halogen, cyano or H, or
R6 is (1-4C)alkyl, (3-6C)alkenoxy, the alkyl or alkoxy moieties of which may optionally be substituted with one or more substituents selected from R10, or
R6 together with R7 is —O—(CH$_2$)—O— in which the CH$_2$ moiety may optionally be substituted by one or more (1-3C)alkyl substituents;
R7 is hydroxy, or
R7 is (1-4C)alkyl, (3-6C)alkenoxy, (3-6C)cycloalkyl(1-4C)alkoxy, (2-6C)heterocycloalkylcarbonyl, (di)[1-4C]alkylaminocarbonyl or (2-6C)heterocycloalkyl, the alkyl, alkoxy or (hetero)cycloalkyl moieties of which may optionally be substituted with one or more substituents selected from R11, or
R7 is (2-8C)heteroaryl, or
R7 together with R6 is —O—(CH$_2$)—O— in which the CH$_2$ moiety may optionally be substituted by one or more (1-3C)alkyl substituents.

7. The compound according to claim 4 wherein
R6 and R7 are independently (1-4C)alkoxy or (3-6C)alkenoxy, or
R6 together with R7 is —O—CH$_2$—O—.

8. The compound according to claim 1 selected from the group of
(R)—N-(1-hydroxy-3-(1H-indol-3-yl)propan-2-yl)-6,7,8-trimethoxy-2-phenyl-9,10-dihydrophenanthrene-3-carboxamide;
2-(2-fluorophenyl)-N—((R)-1-hydroxy-3-(1H-indol-3-yl)propan-2-yl)-6,7,8-trimethoxy-9,10-dihydrophenanthrene-3-carboxamide;
2-(2,3-difluorophenyl)-N—((R)-1-hydroxy-3-(1H-indol-3-yl)propan-2-yl)-6,7,8-trimethoxy-9,10-dihydrophenanthrene-3-carboxamide;
(R)—N-(1-hydroxy-3-(1H-indol-3-yl)propan-2-yl)-6,7,8-trimethoxy-2-(thiophen-2-yl)-9,10-dihydrophenanthrene-3-carboxamide;
N—((R)-1-hydroxy-3-(1H-indol-3-yl)propan-2-yl)-6,7,8-trimethoxy-2-(3-methylthiophen-2-yl)-9,10-dihydrophenanthrene-3-carboxamide;
N—((R)-1-hydroxy-3-(1H-indol-3-yl)propan-2-yl)-6,7,8-trimethoxy-2-(2-methoxypyridin-3-yl)-9,10-dihydrophenanthrene-3-carboxamide;
(R)—N-(1-hydroxy-3-(1H-indol-3-yl)propan-2-yl)-2-isopropoxy-6,7,8-trimethoxy-9,10-dihydrophenanthrene-3-carboxamide;
(R)-2-(cyclopropylmethoxy)-N-(1-hydroxy-3-(1H-indol-3-yl)propan-2-yl)-6,7-dimethoxy-9,10-dihydrophenanthrene-3-carboxamide;
(R)-2-(cyclopentyloxy)-N-(1-hydroxy-3-(1H-indol-3-yl)propan-2-yl)-6,7-dimethoxy-9,10-dihydrophenanthrene-3-carboxamide;
N—((R)-1-hydroxy-3-(1H-indol-3-yl)propan-2-yl)-6,7-dimethoxy-2-(pentan-2-yloxy)-9,10-dihydrophenanthrene-3-carboxamide;
(R)-2-(difluoromethoxy)-N-(1-hydroxy-3-(1H-indol-3-yl)propan-2-yl)-6,7-dimethoxy-9,10-dihydrophenanthrene-3-carboxamide;
2-(1-cyanoethoxy)-N—((R)-1-hydroxy-3-(1H-indol-3-yl)propan-2-yl)-6,7-dimethoxy-9,10-dihydrophenanthrene-3-carboxamide;
(R)-2-(allyloxy)-N-(1-hydroxy-3-(1H-indol-3-yl)propan-2-yl)-6,7-dimethoxy-9,10-dihydrophenanthrene-3-carboxamide;
2-(2-amino-1-fluoro-2-oxoethoxy)-N—((R)-1-hydroxy-3-(1H-indol-3-yl)propan-2-yl)-6,7-dimethoxy-9,10-dihydrophenanthrene-3-carboxamide;
(R)—N-(1-hydroxy-3-(1H-indol-3-yl)propan-2-yl)-6,7-dimethoxy-2-(2-methoxyethoxy)-9,10-dihydrophenanthrene-3-carboxamide;
(R)-2-(benzyloxy)-N-(1-hydroxy-3-(1H-indol-3-yl)propan-2-yl)-6,7-dimethoxy-9,10-dihydrophenanthrene-3-carboxamide;
(R)-2-(2-(dimethylamino)ethoxy)-N-(1-hydroxy-3-(1H-indol-3-yl)propan-2-yl)-6,7-dimethoxy-9,10-dihydrophenanthrene-3-carboxamide;
2-(2-fluorophenyl)-N—((R)-1-hydroxy-3-(1H-indol-3-yl)propan-2-yl)-6,7-dimethoxy-9,10-dihydrophenanthrene-3-carboxamide;
(R)-2-(2,6-difluoro-4-hydroxyphenyl)-N-(1-hydroxy-3-(1H-indol-3-yl)propan-2-yl)-6,7-dimethoxy-9,10-dihydrophenanthrene-3-carboxamide;
2-(4-amino-2-fluorophenyl)-N—((R)-1-hydroxy-3-(1H-indol-3-yl)propan-2-yl)-6,7-dimethoxy-9,10-dihydrophenanthrene-3-carboxamide;
2-(3-fluoropyridin-4-yl)-N—((R)-1-hydroxy-3-(1H-indol-3-yl)propan-2-yl)-6,7-dimethoxy-9,10-dihydrophenanthrene-3-carboxamide;
(R)—N-(1-hydroxy-3-(1H-indol-3-yl)propan-2-yl)-6,7-dimethoxy-2-(3-methylbut-2-en-2-yl)-9,10-dihydrophenanthrene-3-carboxamide;
(R)-2-(5-chlorothiophen-2-yl)-N-(1-hydroxy-3-(1H-indol-3-yl)propan-2-yl)-6,7-dimethoxy-9,10-dihydrophenanthrene-3-carboxamide;

(R)-2-(furan-2-yl)-N-(1-hydroxy-3-(1H-indol-3-yl)propan-2-yl)-6,7-dimethoxy-9,10-dihydrophenanthrene-3-carboxamide;

(R)—N-(1-hydroxy-3-(1H-indol-3-yl)propan-2-yl)-6,7-dimethoxy-2-(3-methoxyphenyl)-9,10-dihydrophenanthrene-3-carboxamide;

(R)-2-(3-carbamoylphenyl)-N-(1-hydroxy-3-(1H-indol-3-yl)propan-2-yl)-6,7-dimethoxy-9,10-dihydrophenanthrene-3-carboxamide;

(R)-2-(4-(dimethylamino)phenyl)-N-(1-hydroxy-3-(1H-indol-3-yl)propan-2-yl)-6,7-dimethoxy-9,10-dihydrophenanthrene-3-carboxamide;

7-(allyloxy)-2-(2-fluorophenyl)-N—((R)-1-hydroxy-3-(1H-indol-3-yl)propan-2-yl)-6-methoxy-9,10-dihydrophenanthrene-3-carboxamide;

6-(allyloxy)-2-(2-fluorophenyl)-N—((R)-1-hydroxy-3-(1H-indol-3-yl)propan-2-yl)-7-methoxy-9,10-dihydrophenanthrene-3-carboxamide;

2-(2-fluorophenyl)-7-hydroxy-N—((R)-1-hydroxy-3-(1H-indol-3-yl)propan-2-yl)-6-methoxy-9,10-dihydrophenanthrene-3-carboxamide;

2-(2-fluorophenyl)-6-hydroxy-N—((R)-1-hydroxy-3-(1H-indol-3-yl)propan-2-yl)-7-methoxy-9,10-dihydrophenanthrene-3-carboxamide;

(R)-6-bromo-N-(1-hydroxy-3-(1H-indol-3-yl)propan-2-yl)-2-isopropoxy-7-methoxy-9,10-dihydrophenanthrene-3-carboxamide;

(R)-6-cyano-N-(1-hydroxy-3-(1H-indol-3-yl)propan-2-yl)-2-isopropoxy-7-methoxy-9,10-dihydrophenanthrene-3-carboxamide;

(R)—N-(1-hydroxy-3-(1H-indol-3-yl)propan-2-yl)-3-isopropoxy-8,9-dimethoxy-6H-benzo[c]chromene-2-carboxamide;

(R)—N-(1-hydroxy-3-(1H-indol-3-yl)propan-2-yl)-3-isopropoxy-8,9-(1',3'-dioxolo)-6H-benzo[c]chromene-2-carboxamide;

3-(2-fluorophenyl)-N—((R)-1-hydroxy-3-(1H-indol-3-yl)propan-2-yl)-8,9-dimethoxy-6H-benzo[c]chromene-2-carboxamide;

3-(2,3-difluorophenyl)-N—((R)-1-hydroxy-3-(1H-indol-3-yl)propan-2-yl)-8,9-dimethoxy-6H-benzo[c]chromene-2-carboxamide;

3-(3,5-dimethyl-1H-pyrazol-4-yl)-N—((R)-1-hydroxy-3-(1H-indol-3-yl)propan-2-yl)-8,9-dimethoxy-6H-benzo[c]chromene-2-carboxamide;

N—((R)-1-hydroxy-3-(1H-indol-3-yl)propan-2-yl)-8,9-dimethoxy-3-(3-methylthiophen-2-yl)-6H-benzo[c]chromene-2-carboxamide;

(R)—N-(1-hydroxy-3-(1H-indol-3-yl)propan-2-yl)-8,9-dimethoxy-3-phenyl-6H-benzo[c]chromene-2-carboxamide;

(R)—N-(1-hydroxy-3-(1H-indol-3-yl)propan-2-yl)-8,9-dimethoxy-3-(2-methylprop-1-enyl)-6H-benzo[c]chromene-2-carboxamide;

(R)—N-(1-hydroxy-3-(1H-indol-3-yl)propan-2-yl)-3-isobutyl-8,9-dimethoxy-6H-benzo[c]chromene-2-carboxamide;

3-(2-fluorophenyl)-N—((R)-1-hydroxy-3-(1H-indol-3-yl)propan-2-yl)-8-isopropoxy-9-methoxy-6H-benzo[c]chromene-2-carboxamide;

3-(2-fluorophenyl)-8-hydroxy-N—((R)-1-hydroxy-3-(1H-indol-3-yl)propan-2-yl)-9-methoxy-6H-benzo[c]chromene-2-carboxamide;

3-(2-fluorophenyl)-N—((R)-1-hydroxy-3-(1H-indol-3-yl)propan-2-yl)-9-methoxy-8-(2-methoxyethoxy)-6H-benzo[c]chromene-2-carboxamide;

8-(allyloxy)-3-(2-fluorophenyl)-N—((R)-1-hydroxy-3-(1H-indol-3-yl)propan-2-yl)-9-methoxy-6H-benzo[c]chromene-2-carboxamide;

3-(2-fluorophenyl)-N—((R)-1-hydroxy-3-(1H-indol-3-yl)propan-2-yl)-8-(2-hydroxyethoxy)-9-methoxy-6H-benzo[c]chromene-2-carboxamide;

8-(2-(dimethylamino)ethoxy)-3-(2-fluorophenyl)-N—((R)-1-hydroxy-3-(1H-indol-3-yl)propan-2-yl)-9-methoxy-6H-benzo[c]chromene-2-carboxamide;

8-(cyclopropylmethoxy)-3-(2-fluorophenyl)-N—((R)-1-hydroxy-3-(1H-indol-3-yl)propan-2-yl)-9-methoxy-6H-benzo[c]chromene-2-carboxamide;

3-(2-fluorophenyl)-N—((R)-1-hydroxy-3-(1H-indol-3-yl)propan-2-yl)-9-methoxy-8-(pyridin-3-yl)-6H-benzo[c]chromene-2-carboxamide;

3-(2-fluorophenyl)-N—((R)-1-hydroxy-3-(1H-indol-3-yl)propan-2-yl)-9-methoxy-8-(1-methyl-1H-pyrazol-4-yl)-6H-benzo[c]chromene-2-carboxamide;

3-(2-fluorophenyl)-N—((R)-1-hydroxy-3-(1H-indol-3-yl)propan-2-yl)-9-methoxy-8-(pyridin-4-yl)-6H-benzo[c]chromene-2-carboxamide;

3-(2-fluorophenyl)-N—((R)-1-hydroxy-3-(1H-indol-3-yl)propan-2-yl)-8-(morpholine-4-carbonyl)-6H-benzo[c]chromene-2-carboxamide;

3-(2-fluorophenyl)-N2-((R)-1-hydroxy-3-(1H-indol-3-yl)propan-2-yl)-N8,N8-dimethyl-6H-benzo[c]chromene-2,8-dicarboxamide;

3-(2-fluorophenyl)-N—((R)-1-hydroxy-3-(1H-indol-3-yl)propan-2-yl)-8,9-(1',3'-dioxolo)-6H-benzo[c]chromene-2-carboxamide;

N—((R)-1-hydroxy-3-(1H-indol-3-yl)propan-2-yl)-8,9-(1',3'-dioxolo)-3-(3-methylthiophen-2-yl)-6H-benzo[c]chromene-2-carboxamide; and N—((R)-1-hydroxy-3-(1H-indol-3-yl)propan-2-yl)-8,9-(1',3'-dioxolo)-3-(3-isopropoxy)-6-oxo-6H-benzo[c]chromene-2-carboxamide.

9. A pharmaceutical composition which comprises a compound of formula I according to claim 1 or a pharmaceutically acceptable salt thereof and one or more pharmaceutically acceptable excipients.

10. A pharmaceutical composition according to claim 9, which further comprises at least one additional therapeutically active agent.

11. A method of treating endometriosis, pre-menopausal and peri-menopausal hormone-dependent breast cancer, uterine fibroids, or other menstrual-related disorders, comprising administering a compound according to claim 1.

12. A method of contraception comprising administering a compound according to claim 1.

* * * * *